(12) United States Patent
Brown et al.

(10) Patent No.: US 11,026,914 B2
(45) Date of Patent: Jun. 8, 2021

(54) USE OF DIANHYDROGALACTITOL AND ANALOGS AND DERIVATIVES THEREOF TO TREAT RECURRENT MALIGNANT GLIOMA OR PROGRESSIVE SECONDARY BRAIN TUMOR

(71) Applicant: DelMar Pharmaceuticals, Inc., Vancouver (CA)

(72) Inventors: Dennis M. Brown, Menlo Park, CA (US); Kent C. Shih, Nashville, TN (US); Anne Steino, Vancouver (CA); Richard Schwartz, Burlingame, CA (US); Sarath Kanekal, San Diego, CA (US); Howard A. Burris, III, Nashville, TN (US); Jeffrey A. Bacha, Vancouver (CA); William J. Garner, San Francisco, CA (US); Shaun Fouse, Menlo Park, CA (US)

(73) Assignee: DEL MAR PHARMACEUTICALS (BC) LTD., Vancouver (CA)

( * ) Notice: Subject to any disclaimer, the term of this patent is extended or adjusted under 35 U.S.C. 154(b) by 0 days.

(21) Appl. No.: 14/682,226

(22) Filed: Apr. 9, 2015

(65) Prior Publication Data
US 2016/0158186 A1    Jun. 9, 2016

Related U.S. Application Data

(63) Continuation-in-part of application No. PCT/US2014/040461, filed on Jun. 2, 2014.

(60) Provisional application No. 61/829,739, filed on May 31, 2013.

(51) Int. Cl.
*A61K 31/336*    (2006.01)
*A61K 45/06*    (2006.01)

(52) U.S. Cl.
CPC ............ *A61K 31/336* (2013.01); *A61K 45/06* (2013.01)

(58) Field of Classification Search
CPC ....... A61K 31/336; A61K 45/06; A61P 25/00; A61P 35/00; A61P 43/00
See application file for complete search history.

(56) References Cited

U.S. PATENT DOCUMENTS

| 5,294,430 A | 3/1994 | Borch et al. |
| 2014/0221442 A1 | 8/2014 | Bacha et al. |

FOREIGN PATENT DOCUMENTS

| JP | H0150091 A | 3/1989 |
| WO | 1988/000834 A1 | 2/1988 |
| WO | WO 2012024367 A2 * | 2/2012 | ............ A61K 31/44 |
| WO | WO-2013110058 A2 * | 7/2013 | ............ C12Q 1/6886 |
| WO | 2013/169600 A1 | 11/2013 | |

OTHER PUBLICATIONS

Ujifuku et. al., Cancer Letters, 2010, Elsevier, vol. 296, pp. 241-248.*
Uckun et. al., Bioorganic and Medicinal Chemistry Letters, 2001, Pergamon, vol. 11, pp. 1181-1183.*
Peyton et. al., Journal of Clinical Oncology, May 20, 2013, American Soc Clin Oncology, vol. 31(15), suppl. 1, abstract 2093 (Year: 2013).*
Karim et. al., Anticancer Research, 2005, The International Institute of Anticancer Research, vol. 25, pp. 2969-2972 (Year: 2005).*
Jiang et. al., Biochem & Biophys Res. Commun., 2011, Elsevier, vol. 406, pp. 311-314 (Year: 2011).*
Iwamoto et. al., Neurology, 2009, AAN Enterprises Inc., vol. 73, pp. 1200-1206 (Year: 2009).*
European Office Action for related European Patent Application No. 14804823.4-1453 dated Jan. 29, 2016, 2 Pages.
Bacha, J., et al., "DelMar Pharmaceuticals," 14th Annual Healthcare Conference, Sep. 11, 2012.
Hu, K., et al., "Abstract 811: VAL083, a Novel N7 Alkylating Agent, Surpasses Temozolomide Activity and Inhibits Cancer Stem Cells Providing a New Potential Treatment Option for Glioblastoma Multiforme," Proceedings of the 103rd Annual Meeting of the American Association for Cancer Research, Chicago, Mar. 31-Apr. 4, 2012, Cancer Research 72(8 Suppl): Abstract, Apr. 2012.
Pikkarainen, J.T., et al., "Avidin-Biotin Technology and Targeted Treatment of Malignant Glioma," Publications of the University of Eastern Finland, Dissertations in Health Sciences., No. 109, May 2012, 112 pages.
International Search Report and Written Opinion dated Dec. 10, 2014, issued in International Application No. PCT/US2014/040461, filed Jun. 2, 2014, 17 pages.
International Preliminary Report on Patentability dated Jun. 5, 2015, issued in International Application No. PCT/US2014/040461, filed Jun. 2, 2014, 9 pages.
First Office Action dated Nov. 27, 2017, issued in Chinese Application No. 201480042784.2, filed Jun. 2, 2014, 7 pages.
Search Report and First Written Opinion dated Oct. 12, 2016, issued in Singapore Application No. 11201500987Q, filed Jun. 2, 2014, 14 pages.
Second Written Opinion dated Jul. 10, 2017, issued in Singapore Application No. 11201500987Q, filed Jun. 2, 2014, 10 pages.
First Office Action dated Apr. 18, 2017, issued in Chile Application No. 2015-003512, filed Jun. 2, 2014, 17 pages.
Second Office Action dated Aug. 16, 2017, issued in Chile Application No. 2015-003512, filed Jun. 2, 2014, 14 pages.
DelMar Pharmaceuticals, Inc., "Open-Label, Single Arm, Safety and Tolerability Dose Escalation Study of VAL-083 in Patients With Recurrent Malignant Glioma or Progressive Secondary Brain Tumor," ClinicalTrials.gov archive, No. NCT1478178, Feb. 28, 2013, <https://clinicaltrials.gov/archive/NCT01478178/2013_27_28> [retrieved Mar. 12, 2018], 3 pages.

(Continued)

*Primary Examiner* — Sarah Pihonak
(74) *Attorney, Agent, or Firm* — Christensen O'Connor Johnson Kindness PLLC

(57) ABSTRACT

Methods and compositions suitable for the treatment of malignancies such as recurrent glioma and progressive secondary brain tumor are disclosed. These methods employ a hexitol derivative such as dianhydrogalactitol, a derivative or analog of dianhydrogalactitol, diacetyldianhydrogalactitol, or a derivative or analog of diacetyldianhydrogalactitol. The compositions can include such hexitol derivatives.

8 Claims, 33 Drawing Sheets

(56) References Cited

OTHER PUBLICATIONS

Eagan, R.T., et al., "Dianhydrogalactitol and Radiation Therapy: Treatment of Supratentorial Glioma," Journal of the American Medical Association 241(19):2046-2050, May 1979.
España, P., et al., "Phase II Study of Dianhydrogalactitol in Malignant Glioma," Cancer Treatment Reports 62(8):1199-1200, Aug. 1978.
Notice of Reasons for Rejection dated Apr. 3, 2018, issued in Japanese Application No. 2016-517073, filed Jun. 2, 2014, 15 pages.
Extended European Search Report dated Dec. 20, 2016, issued in EP Application No. 14804823.4, filed Jun. 2, 2014, 8 pages.
Office Action dated Sep. 21, 2018, issued in EP Application No. 14804823.4, filed Jun. 2, 2014, 6 pages.
Brown, D.M., et al., "Abstract 4672: Phase I/II Study of Val-083 in Patients With Recurrent Malignant Glioma or Secondary Brain Tumor," In: Proceedings of the 104th Annual Meeting of the American Association for Cancer Research, Apr. 6-10, 2013; Washington, DC, Cancer Research 73(8 Suppl):Abstract nr 4672, Apr. 2013, 3 pages.
De Jager, et al., "Dianhydrogalactitol (NCS-132313): Phase II Study in Solid Tumors: A Report of the E.O.R.T.C. Early Clinical Trial Cooperative Group," European Journal of Cancer 15:971-974, Jan. 1979.
Notice of Reasons for Rejection dated Feb. 19, 2019, issued in JP Application No. 2016-517073, filed Jun. 2, 2014, 13 pages.
Brown, D.M., et al., "Phase I/II Study of VAL-083 in Patients With Recurrent Malignant Glioma or Secondary Brain Tumor," Cancer Research 73(Suppl. 8): Abstract 4672, Apr. 2013, 3 pages.

DelMar Pharmaceuticals, Inc., "Open-Label, Single Arm, Safety and Tolerability Dose Escalation Study of VAL-083 in Patients With Recurrent Malignant Glioma or Progressive Secondary Brain Tumor," ClinicalTrials.gov. Archive, No. NCT1478178, Archive History of Changes for Study: NCT1478178 <https://clinicaltrials.gov/ct2/history/NCT01478178> [retrieved May 23, 2019], pages.
Peyton, J.D., et al., "Phase I/II Study of Dianhydrogalactitol in Patients With Recurrent Malignant Glioma or Progressive Secondary Brain Tumor," Journal of Clinical Oncology 31(Suppl.15): Abstract 2093, May 2013, 2 pages.
Shin, K.C., et al., "Phase I/II Study of VAL-083 in Patients With Recurrent Malignant Glioma," Neuro-Oncology 14(Suppl. 6):vi101-vi105, Abstract OT-15, Nov. 2012.
Shin, K.C., et al., "Phase I/II Study of VAL-083 in Patients with Recurrent Malignant Glioma," 12th Annual Meeting of the Society for Neuro-Oncology, Washington, D.C., Nov. 15-18, 2012, Poster, 1 page.
Shin, K.C., et al., "Phase I/II Study of VAL-083 in Patients With Recurrent Malignant Glioma or Secondary Brain Tumor," 104th Annual Meeting of the American Society for Cancer Research, Washington, D.C, Apr. 6-10, 2013, Poster, 1 page.
Shin, K.C., et al., "Phase I/II Study of VAL-083 (Dianhydrogalactitol) in Patients With Recurrent Malignant Glioma or Progressive Secondary Brain Tumor," Annual Meeting of the American Society of Clinical Oncology, Chicago, May 31-Jun. 4, 2013, Poster, 1 page.
Eagan, R.T. et al., "Phase II Studies of Dianhydrogalactitol-Based Combination Chemotherapy for Recurrent Brain Tumors," Oncology 38:4-6, 1981.
Office Action dated Feb. 9, 2021, issued in JP Application No. 2016-517073, filed Jun. 2, 2014, 35 pages.

* cited by examiner

| GBM CELL LINE | SF188 | U251 | T98G |
|---|---|---|---|
| TMZ RESISTANCE | ++ | + | +++ |
| MGMT STATUS | - | - | + |

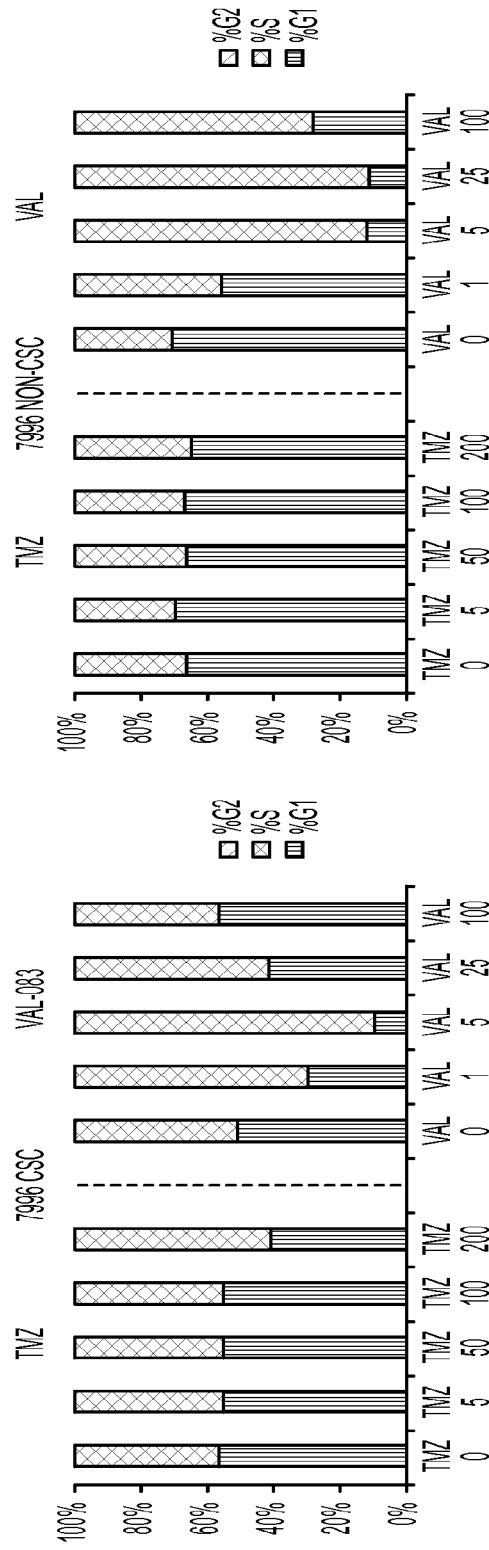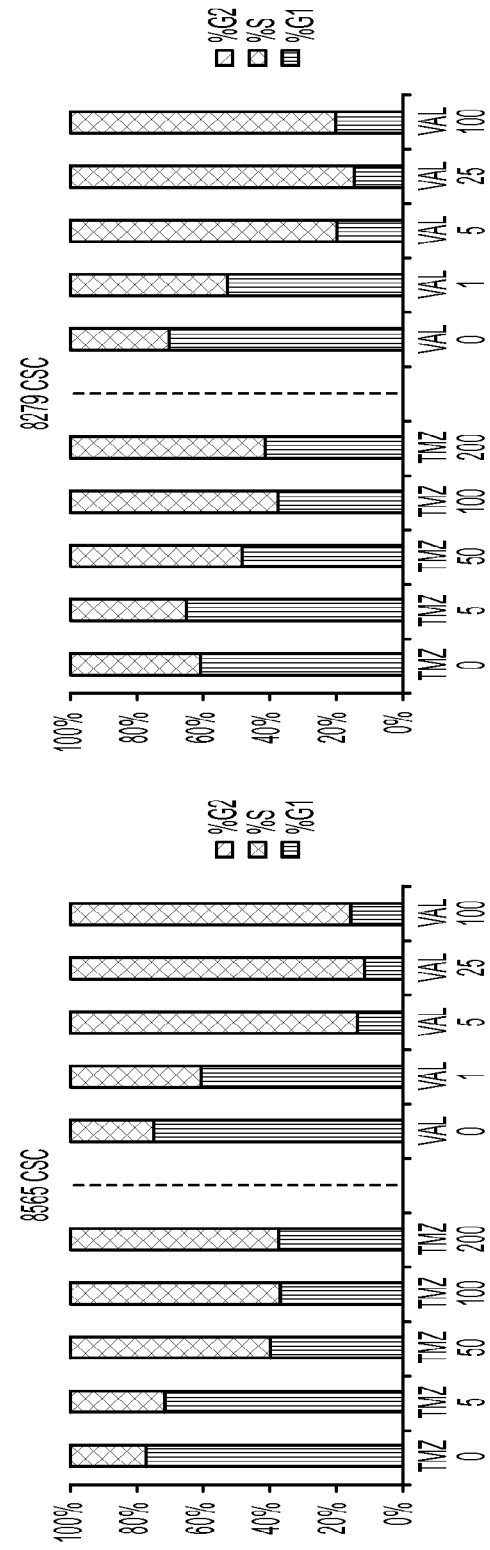
FIG. 17A
FIG. 17B
FIG. 17C
FIG. 17D

USE OF DIANHYDROGALACTITOL AND ANALOGS AND DERIVATIVES THEREOF TO TREAT RECURRENT MALIGNANT GLIOMA OR PROGRESSIVE SECONDARY BRAIN TUMOR

This application is a continuation in part of International Application No. PCT/US2014/040461, filed Jun. 2, 2014, which in turn claims the benefit of U.S. Provisional Application No. 61/829,739, filed May 31, 2013. The contents of both of these applications are hereby incorporated in their entirety by this reference.

FIELD OF THE INVENTION

This invention is directed to methods of use and compositions comprising dianhydrogalactitol or analogs or derivatives thereof to treat malignant glioma or progressive secondary brain tumor.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infection, and other conditions.

Since the "War on Cancer" began in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, and other biological response modifiers.

The work supported by the NCI, other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other information developed by this work remain critical for the discovery and development of any new therapeutic agent.

Unfortunately, many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated; such cases have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, neurotoxicity, cardiotoxicity, gastrointestinal toxicities, or other significant side effects).

In many cases, after the great time and expense of developing and moving an investigational compound into human clinical trials and where clinical failure has occurred, the tendency has been to return to the laboratory to create a better analog, look for agents with different structures but potentially related mechanisms of action, or try other modifications of the drug. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, genetic markers that can either promote or retard therapeutic efficacy, and other factors, the opportunity for cures in the near term remains elusive. Moreover, the incidence of cancer continues to rise with an approximate 4% increase predicted for 2003 in the United States by the American Cancer Society such that over 1.3 million new cancer cases are estimated. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving the therapeutic benefit of suboptimally administered chemical compounds including substituted hexitols such as dianhydrogalactitol.

Relevant literature includes Foye, W. O., "Cancer Chemotherapeutic Agents," American Chemical Society, 1995, and Dorr, R. T., and Von Hoff, D. D., "Cancer Chemotherapy Handbook," Appleton and Lange, 1994.

Therefore, there is a need for compositions and methods that improve the therapeutic benefit of suboptimally administered chemical compounds and therapeutic compositions. There is a particular need for compositions and methods for treating malignant gliomas such as glioblastoma multiforme and for treating progressive secondary brain tumors, such as those arising from metastases of breast adenocarcinoma, small-cell lung carcinoma, or melanoma.

SUMMARY OF THE INVENTION

This invention meets the needs described above for compositions and methods that improve the therapeutic benefit of suboptimally administered chemical compounds and therapeutic compositions. Specifically, this invention relates to novel compositions and methods to improve the utility of chemical agents with suboptimal performance in patients suffering with cancer, especially malignant gliomas such as glioblastoma multiforme and progressive secondary brain tumors, such as those arising from metastases of breast adenocarcinoma, small-cell lung carcinoma, or melanoma. The invention describes novel improvements, pharmaceutical ingredients, dosage forms, excipients, solvents, diluents, drug delivery systems, preservatives, more accurate drug administrations, improved dose determination and schedules, toxicity monitoring and ameliorization, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches. The invention also relates to the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some case, the use of these suboptimal therapeutics in conjunction with radiation or other conventional chemotherapeutic agents or biotherapeutic agents such as antibodies, vaccines, cytokines, lymphokines, gene and antisense therapies, or other chemotherapeutic or biotherapeutic agents, would provide novel approaches and significant improvement.

In the inventive compositions and methods, the term suboptimal therapy includes agents where Phase I toxicity precluded further human clinical evaluation. It also includes those agents from Phase II trials where limited (<25% response rates) or no significant tumor responses were identified. Also, suboptimal therapy includes those agents, the subject of Phase III clinical trials the outcome of which was either medically or statistically not significant to warrant regulatory submission or approval by government agencies for commercialization or commercialized agents whose clinical performance (i.e. response rates) as a monotherapy are less than 25%, or whose side-effects are severe enough to limit wide utility. Agents with suboptimal clinical activity include but are not limited to the following: substituted hexitols such as dianhydrogalactitol and diacetyldianhydrogalactitol and derivatives and analogs thereof. More specifically, the inventive methods and compositions also focus on improvements for substituted hexitols including dianhydrogalactitol and diacetyldianhydrogalactitol, particularly dianhydrogalactitol.

One aspect of the present invention is a method for the treatment of a malignancy selected from the group consisting of recurrent glioma and progressive secondary brain tumor comprising the administration of a therapeutically effective quantity of a hexitol derivative selected from the group consisting of dianhydrogalactitol, a derivative or analog of dianhydrogalactitol, diacetyldianhydrogalactitol, and a derivative or analog of diacetyldianhydrogalactitol.

Another aspect of the invention is a method to improve the efficacy and/or reduce the side effects of the administration of a hexitol derivative for treatment of a malignancy selected from the group consisting of recurrent glioma and progressive secondary brain tumor comprising the steps of:

(1) identifying at least one factor or parameter associated with the efficacy and/or occurrence of side effects of the administration of the hexitol derivative for treatment of the malignancy; and (2) modifying the factor or parameter to improve the efficacy and/or reduce the side effects of the administration of the hexitol derivative for treatment of the malignancy.

In this method, the factor or parameter can be selected from the group consisting of:

(1) dose modification;
(2) route of administration;
(3) schedule of administration;
(4) selection of disease stage;
(5) patient selection;
(6) patient/disease phenotype;
(7) patient/disease genotype;
(8) pre/post-treatment preparation
(9) toxicity management;
(10) pharmacokinetic/pharmacodynamic monitoring;
(11) drug combinations;
(12) chemosensitization;
(13) chemopotentiation;
(14) post-treatment patient management;
(15) alternative medicine/therapeutic support;
(16) bulk drug product improvements;
(17) diluent systems;
(18) solvent systems;
(19) excipients;
(20) dosage forms;
(21) dosage kits and packaging;
(22) drug delivery systems;
(23) drug conjugate forms;
(24) compound analogs;
(25) prodrugs;
(26) multiple drug systems;
(27) biotherapeutic enhancement;
(28) biotherapeutic resistance modulation;
(29) radiation therapy enhancement;
(30) novel mechanisms of action;
(31) selective target cell population therapeutics; and
(32) use with an agent enhancing its activity.

The drug therapy can be administered to treat a hyperproliferative disease, such as cancer. In particular, the drug therapy can be administered to treat malignant gliomas such as glioblastoma multiforme and progressive secondary brain tumors, such as those arising from metastases of breast adenocarcinoma, small-cell lung carcinoma, or melanoma. In one alternative, the drug therapy possesses cytotoxic activity against cancer stem cells.

Typically, the suboptimally administered drug therapy comprises administration of a substituted hexitol. In one alternative, preferably, the substituted hexitol is selected from the group consisting of dianhydrogalactitol and a derivative or analog thereof. In this alternative, more preferably, the substituted hexitol is dianhydrogalactitol. In another alternative, preferably, the substituted hexitol is selected from the group consisting of diacetyldianhydrogalactitol and a derivative or analog thereof. In this alternative, more preferably, the substituted hexitol is diacetyldianhydrogalactitol.

The following alternatives describe the use of dianhydrogalactitol, diacetyldianhydrogalactitol, or, in some cases as set forth below, a derivative or analog of either dianhydrogalactitol or diacetyldianhydrogalactitol, together with a modification of a factor or parameter as described above to improve the efficacy and/or reduce the side effects of the drug therapy.

Another aspect of the present invention is a composition to improve the efficacy and/or reduce the side effects of suboptimally administered drug therapy employing a substituted hexitol as described above for the treatment of recurrent malignant glioma such as glioblastoma multiforme or the treatment of progressive secondary brain tumor such as that caused by metastases of breast adenocarcinoma, small-cell lung carcinoma, or melanoma comprising an alternative selected from the group consisting of:

(i) a therapeutically effective quantity of a modified hexitol derivative or a derivative, analog, or prodrug of a hexitol derivative or a modified hexitol derivative, wherein the modified hexitol derivative or the derivative, analog or prodrug of the modified hexitol derivative possesses increased therapeutic efficacy or reduced side effects for treatment of a malignancy selected from the group consisting of recurrent glioma and progressive secondary brain tumor as compared with an unmodified hexitol derivative;

(ii) a composition comprising:
  (a) a therapeutically effective quantity of a hexitol derivative, a modified hexitol derivative, or a derivative, analog, or prodrug of a hexitol derivative or a modified hexitol derivative; and
  (b) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects for treatment of a malignancy selected from the group consisting of recurrent glioma and progressive secondary brain tumor as compared with an unmodified hexitol derivative;

(iii) a therapeutically effective quantity of a hexitol derivative, a modified hexitol derivative, or a derivative, analog, or prodrug of a hexitol derivative or a modified hexitol derivative that is incorporated into a dosage form, wherein a hexitol derivative, a modified hexitol derivative, or a derivative, analog, or prodrug of a hexitol derivative or a modified hexitol derivative incorporated into the dosage form possesses increased therapeutic efficacy or reduced side effects for treatment of a malignancy selected from the group consisting of recurrent glioma and progressive secondary brain tumor as compared with an unmodified hexitol derivative;

(iv) a therapeutically effective quantity of a hexitol derivative, a modified hexitol derivative, or a derivative, analog, or prodrug of an hexitol derivative or a modified hexitol derivative that is incorporated into a dosage kit and packaging, wherein a hexitol derivative, a modified hexitol derivative, or a derivative, analog, or prodrug of a hexitol derivative or a modified hexitol derivative incorporated into the dosage kit and packaging possesses increased therapeutic efficacy or reduced side effects for treatment of a malignancy selected from the group consisting of recurrent glioma and progressive secondary brain tumor as compared with an unmodified hexitol derivative; and (v) a therapeutically effective quantity of a hexitol derivative, a modified hexitol derivative, or a derivative, analog, or prodrug of a hexitol derivative or a modified hexitol derivative that is subjected to a bulk drug product improvement, wherein the hexitol derivative, the modified hexitol derivative, or the derivative, analog, or prodrug of the hexitol derivative or the modified hexitol derivative subject to the bulk drug product improvement possesses increased therapeutic efficacy or reduced side effects for treatment of a malignancy selected from the group consisting of recurrent glioma and progressive secondary brain tumor as compared with an unmodified alkylating hexitol derivative.

Typically, the composition possesses increased efficacy or reduced side effects for cancer therapy, especially treatment of malignant gliomas such as recurrent glioblastoma multiforme or treatment of progressive secondary brain tumors, such as those arising from metastases of breast adenocarcinoma, small-cell lung carcinoma, or melanoma. In one alternative, the composition possesses cytotoxic activity against cancer stem cells. Typically, the unmodified therapeutic agent is dianhydrogalactitol or diacetyldianhydrogalactitol.

Another aspect of the present invention is a kit comprising, separately packaged, two or more different doses of a hexitol derivative as described above for treatment of a malignancy.

BRIEF DESCRIPTION OF THE DRAWINGS

These and other features, aspects, and advantages of the present invention will become better understood with reference to the following description, appended claims, and accompanying drawings where:

FIG. 5, shown as FIGS. 5C and 5D, shows the MGMT status of the cultures. "GAPDH" refers to glyceraldehyde-3-phosphate dehydrogenase as a control. For the cell cultures, CSCs were cultured in NSA media supplemented with B27, EGF and bFGF. Non-CSCs were grown in DMEM:F12 with 10% FBS. MGMT methylation and protein expression analysis of each culture was characterized. TMZ or VAL-083 was added to the cultures in the indicated concentrations. Depending on the experiment, cells were also irradiated with 2 Gy in a Cesium irradiator. For assays, cell cycle analysis was performed with Propidium Iodide staining and FACs analysis. Cell viability was analyzed with CellTiter-Glo and read on a Promega GloMax. In FIG. 5, "1° GBM" refers to primary glioblastoma multiforme cell cultures.

In FIG. 12, for TMZ "-D/-" indicates DMSO only (vehicle), "-T/-" indicates TMZ only, and "-D/X" or "-T/X" indicate DMSO or TMZ with XRT. Similarly, for VAL, "-P/-" indicates phosphate buffered saline (PBS) only (vehicle), "-V/-" indicates VAL only, and "-P/X" or "-V/X" indicate PBS or VAL with XRT. The left side of FIG. 12 shows cell cycle analysis where G2 is shown at the top, S in the middle, and G1 at the bottom; both 4- and 6-day results are shown, with the 4-day results ("D4") presented to the left of the 6-day results ("D6"). The right side of FIG. 12 shows the results for cell viability as a percentage of control for D4 and D6.

FIG. 17, shown as FIGS. 17A, 17B, 17C, and 17D, shows that dianhydrogalactitol causes cell cycle arrest in TMZ-resistant cultures in vitro. In FIG. 17, cells were treated with either increasing doses of TMZ (5, 50 100 and 200 μM) or dianhydrogalactitol ("VAL-083") (1, 5, 25 and 100 μM) and cell cycle analysis was performed 4 days post treatment.

TMZ resistant cultures (FIG. 17A, FIG. 17B, FIG. 17D) exhibited sensitivity to VAL-083, even at single-micromolar doses. Furthermore, this response was not dependent on culture type as paired CSC (FIG. 17A) and non-CSC (FIG. 17B) both exhibit sensitivity to VAL-083.

FIG. 18, shown as FIGS. 18A, 18B, 18C, and 18D, shows that dianhydrogalactitol decreases cell viability in TMZ-resistant cultures in vitro. In FIG. 18, TMZ (50 μM) or dianhydrogalactitol ("VAL-083") (5 μM) were added to primary CSC cultures at various doses with or without irradiation (2 Gy). Shown are cell cycle profile analysis at day 4 post treatment (FIG. 18A, FIG. 18C) and cell viability analysis at day 6 post treatment (FIG. 18B, FIG. 18D) for the paired CSC (FIG. 18A, FIG. 18B) and non-CSC (FIG. 18C, FIG. 18D) 7996 culture. Whereas these cultures are not very sensitive to TMZ, they are to VAL-083. However, the addition of radiation (XRT) in both cases does not result in increased sensitivity (D=DMSO, T=TMZ, X=XRT, P=PBS).

Figure 19A:
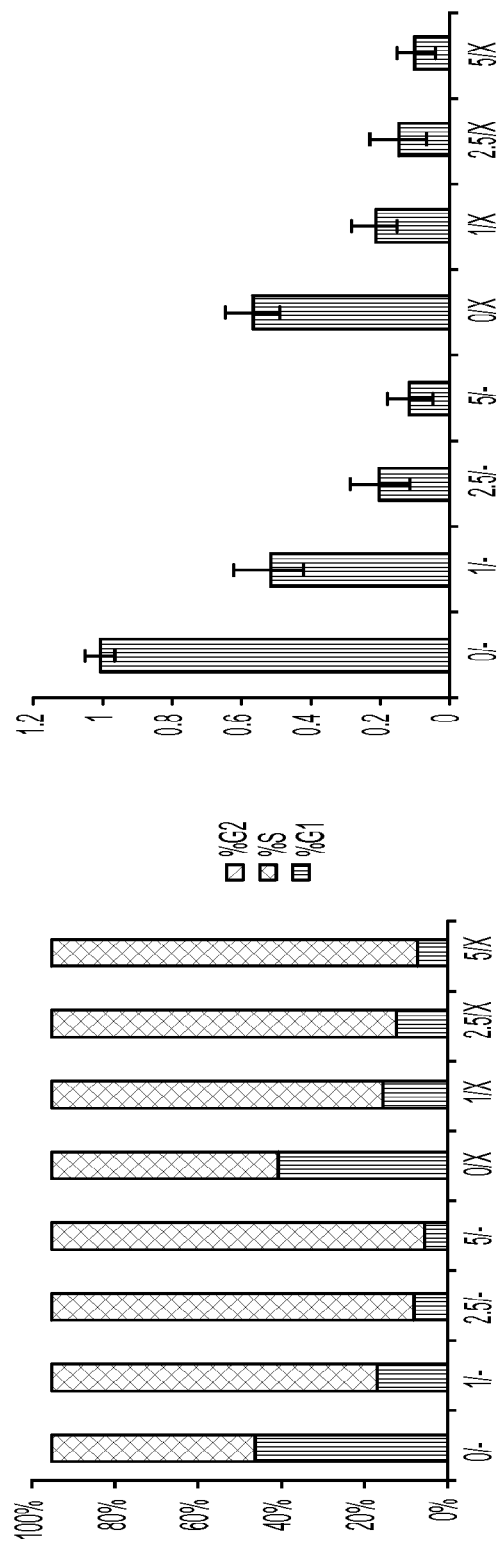
Figure 19B:
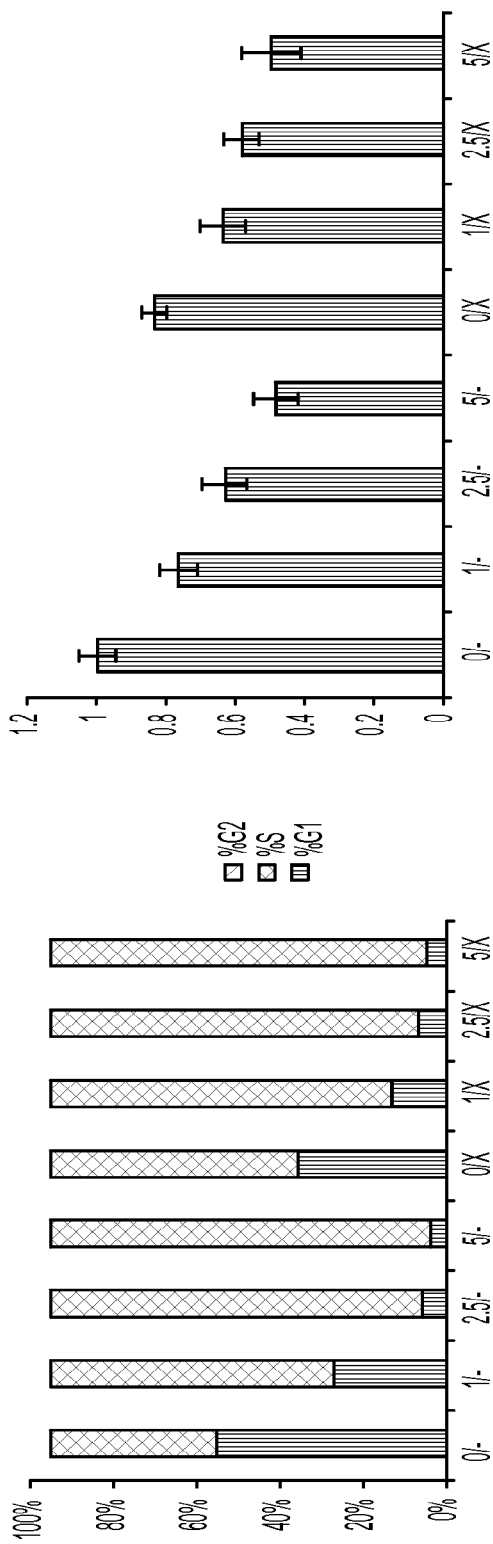
Figure 19C:
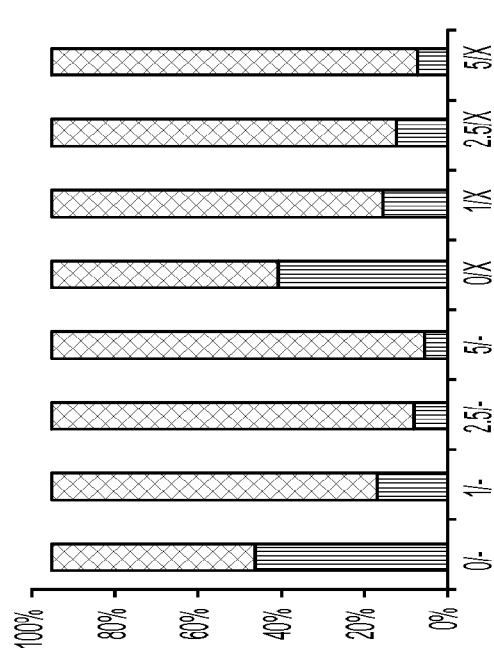
Figure 19D:
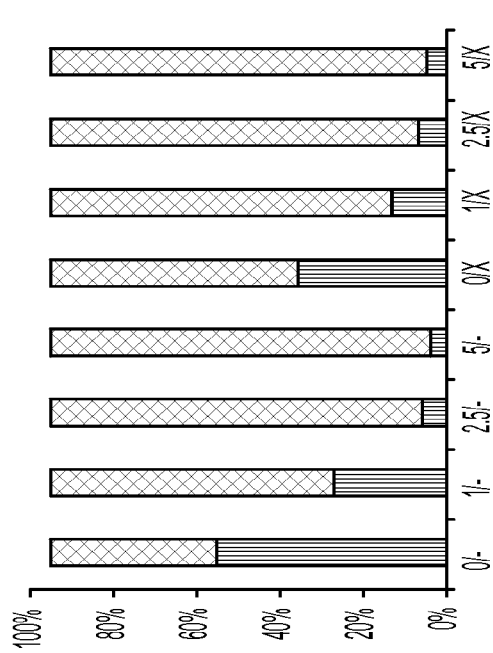

FIG. 19, shown as FIGS. 19A, 19B, 19C, and 19D, shows that dianhydrogalactitol at low dosages acts as a radiosensitizer in primary CSC cultures. In FIG. 19, dianhydrogalactitol ("VAL-083") was added to primary CSC cultures at various doses (1, 2.5 and 5 μM) with or without irradiation (2 Gy). Shown are cell cycle profile analysis at day 4 post treatment (FIG. 19A, FIG. 19C) and cell viability analysis at day 6 post treatment (FIG. 19B, FIG. 19D) for two different patient-derived CSC cultures, 7996 (FIG. 19A, FIG. 19B) and 8565 (FIG. 19C, FIG. 19D).

Figure 20:
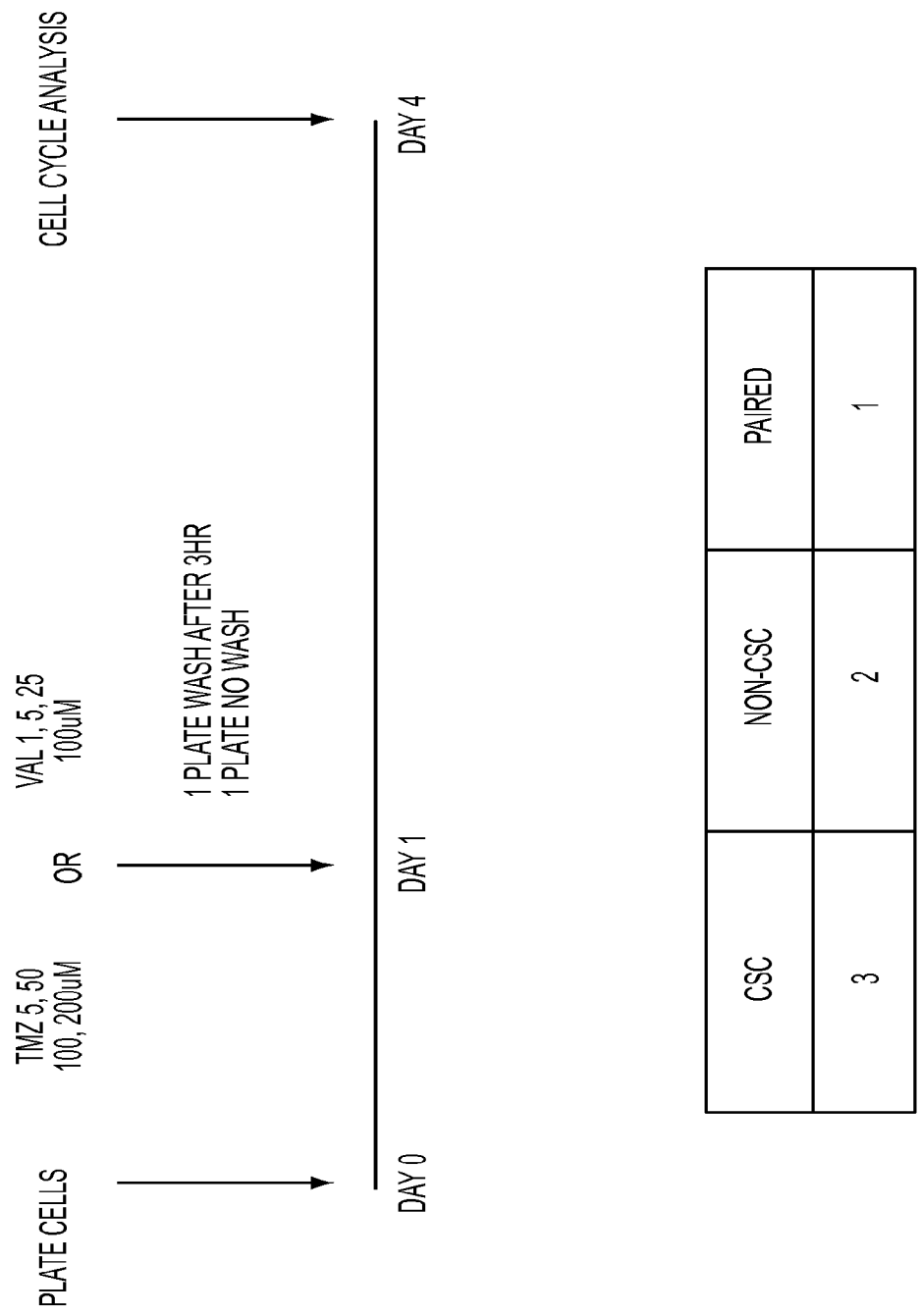

FIG. 20 shows the treatment regimens with a wash or no wash for both dianhydrogalactitol and temozolomide.

Figure 21:
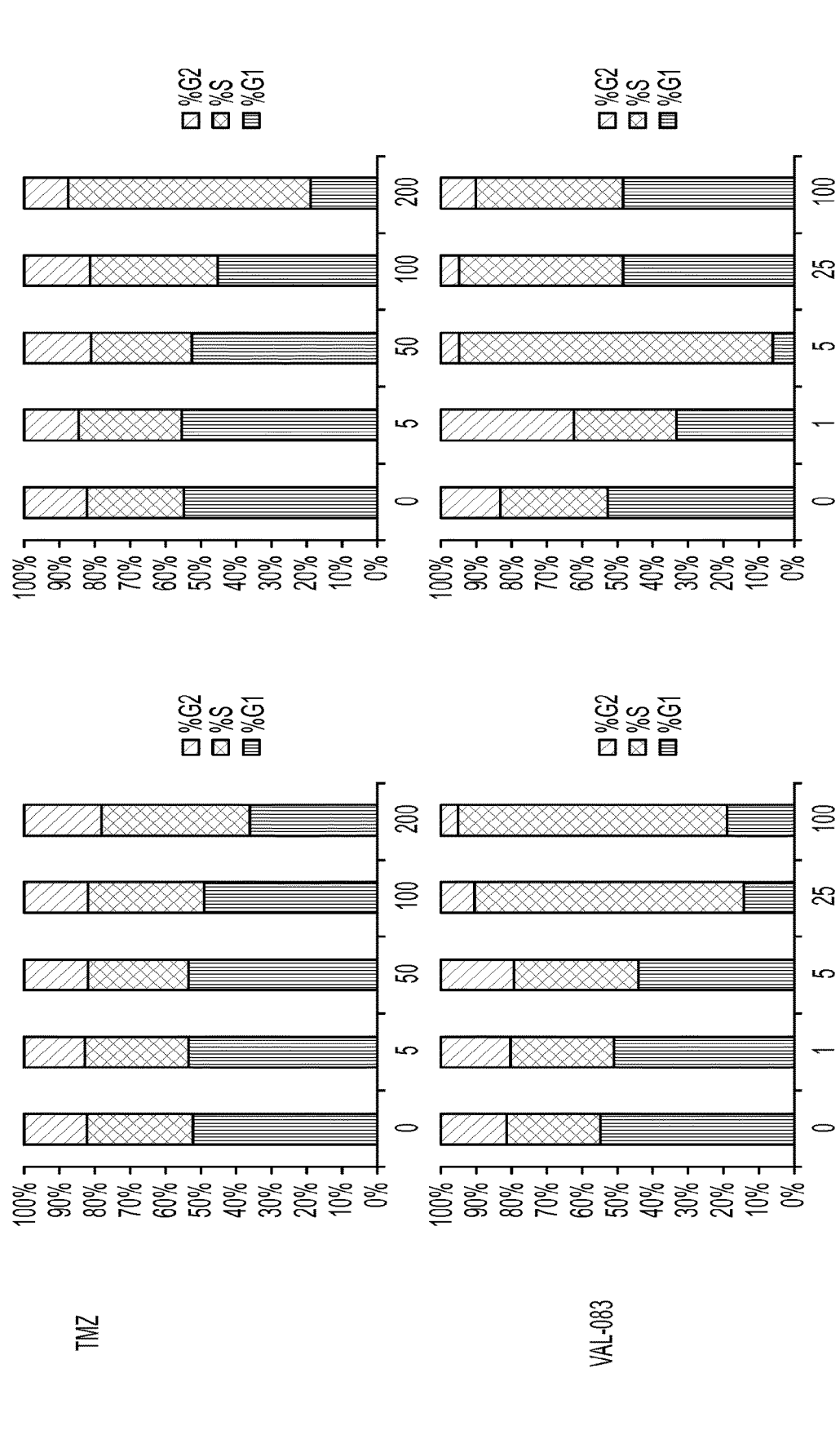

FIG. 21 shows the results for 7996 GNS, showing cell cycle analysis where G2 is shown at the top, S in the middle, and G1 at the bottom. Results for TMZ are shown on the top and results for dianhydrogalactitol on the bottom. Results with a wash are shown on the left and results without a wash are shown on the right.

Figure 22:
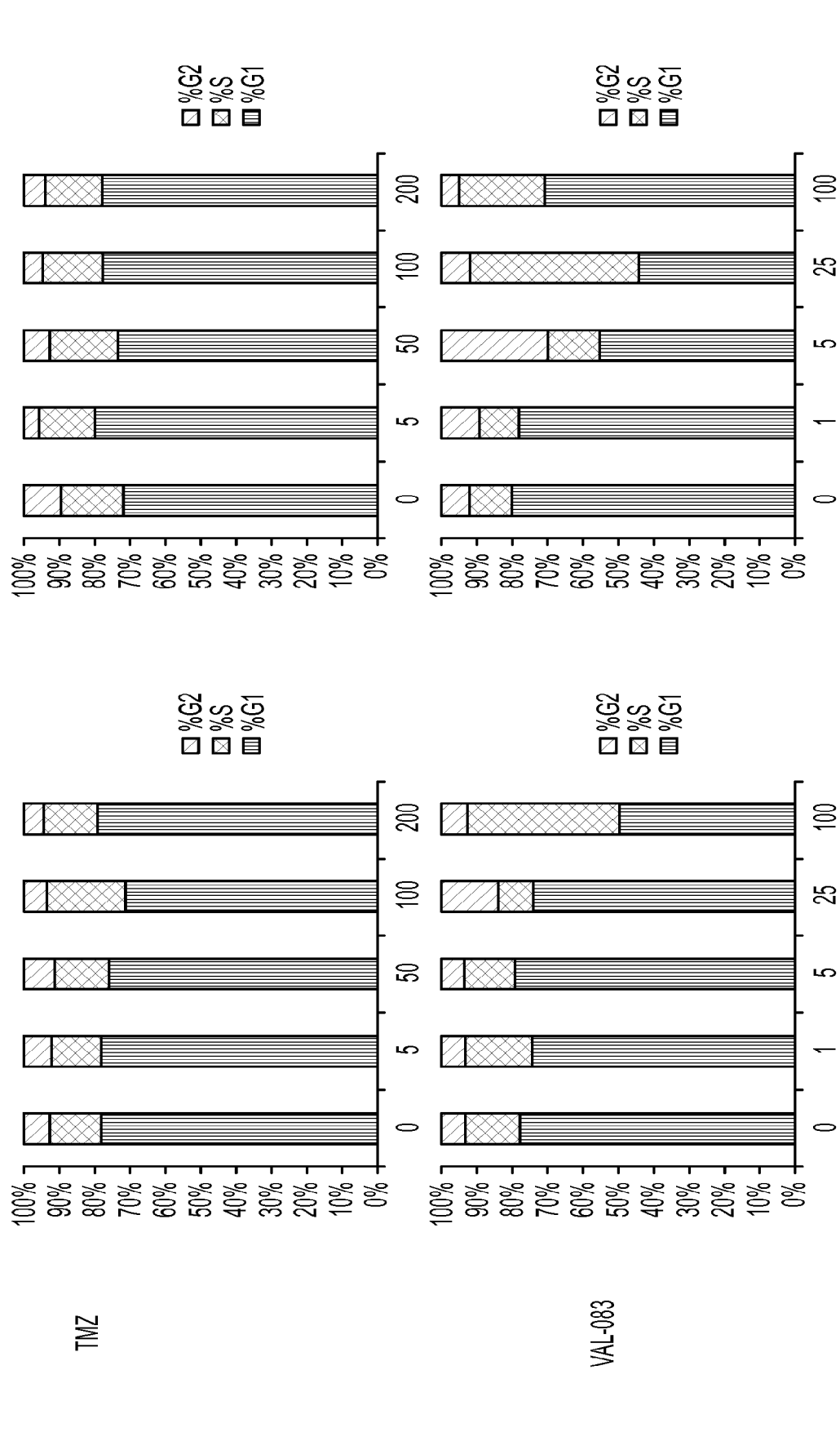

FIG. 22 shows the results for 8279 GNS, depicted as in FIG. 21.

Figure 23:
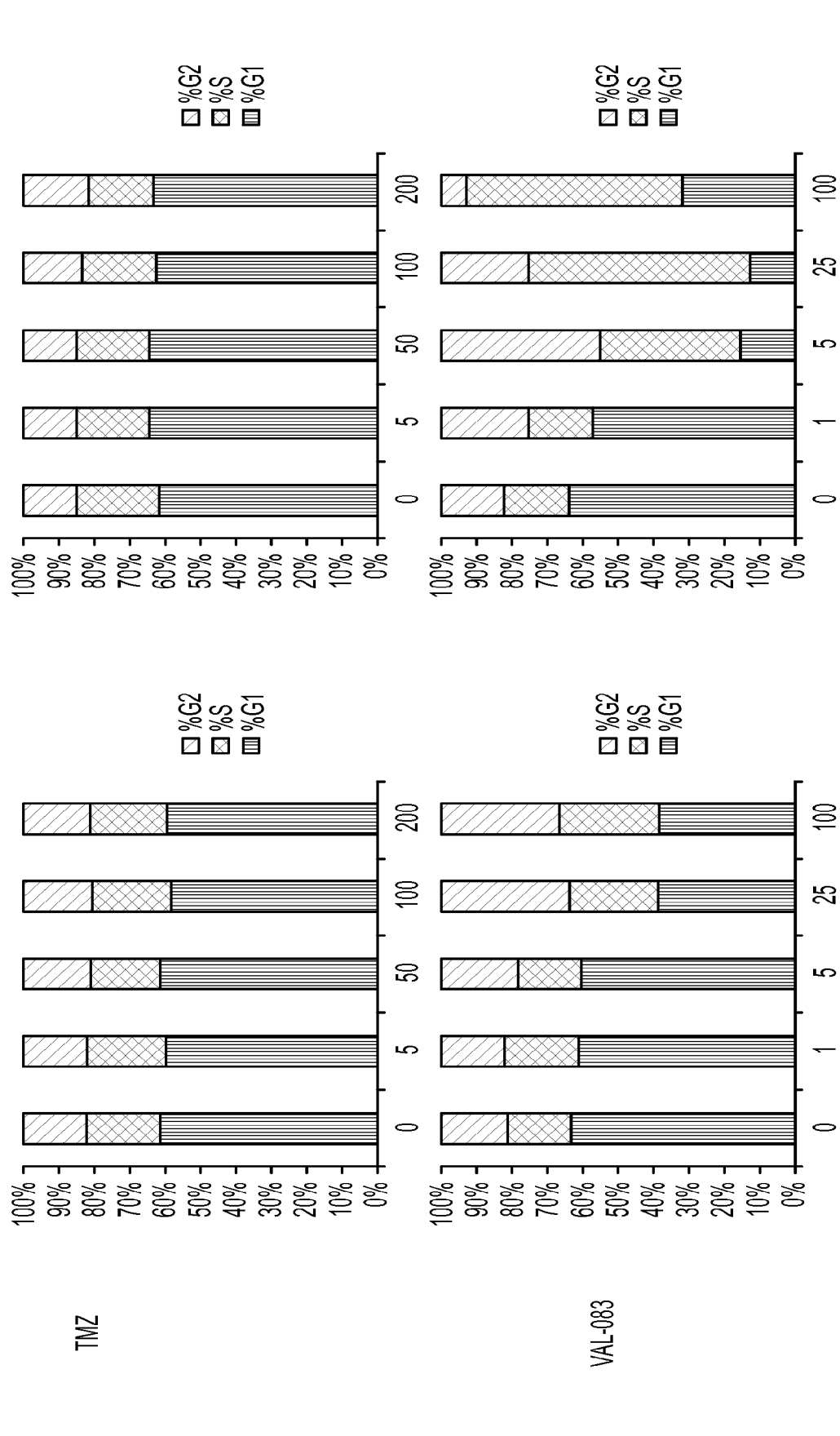

FIG. 23 shows the results for 7996 ML, depicted as in FIG. 21.

Figure 24:
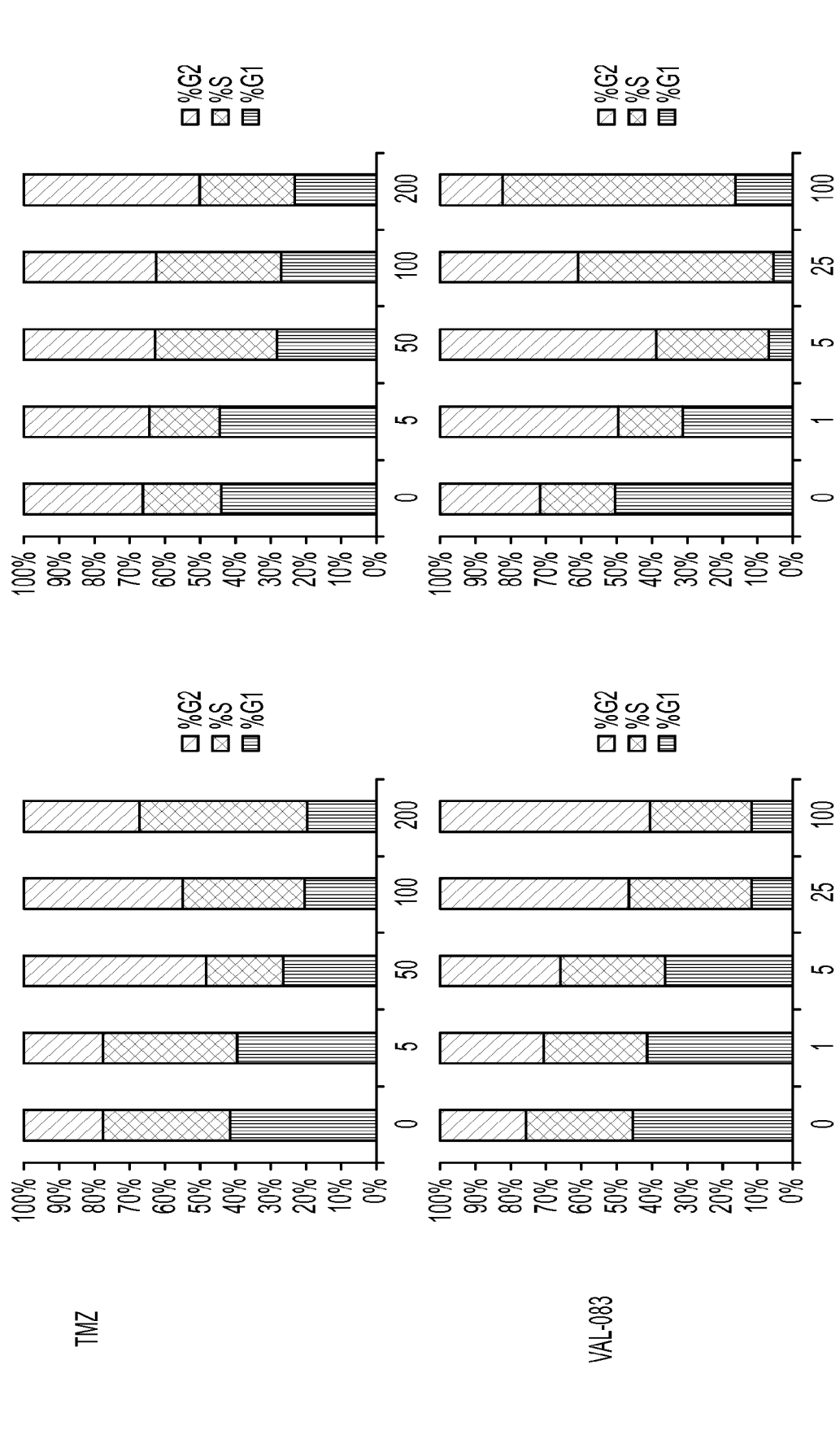

FIG. 24 shows the results for 8565 ML, depicted as in FIG. 21.

Figure 25:
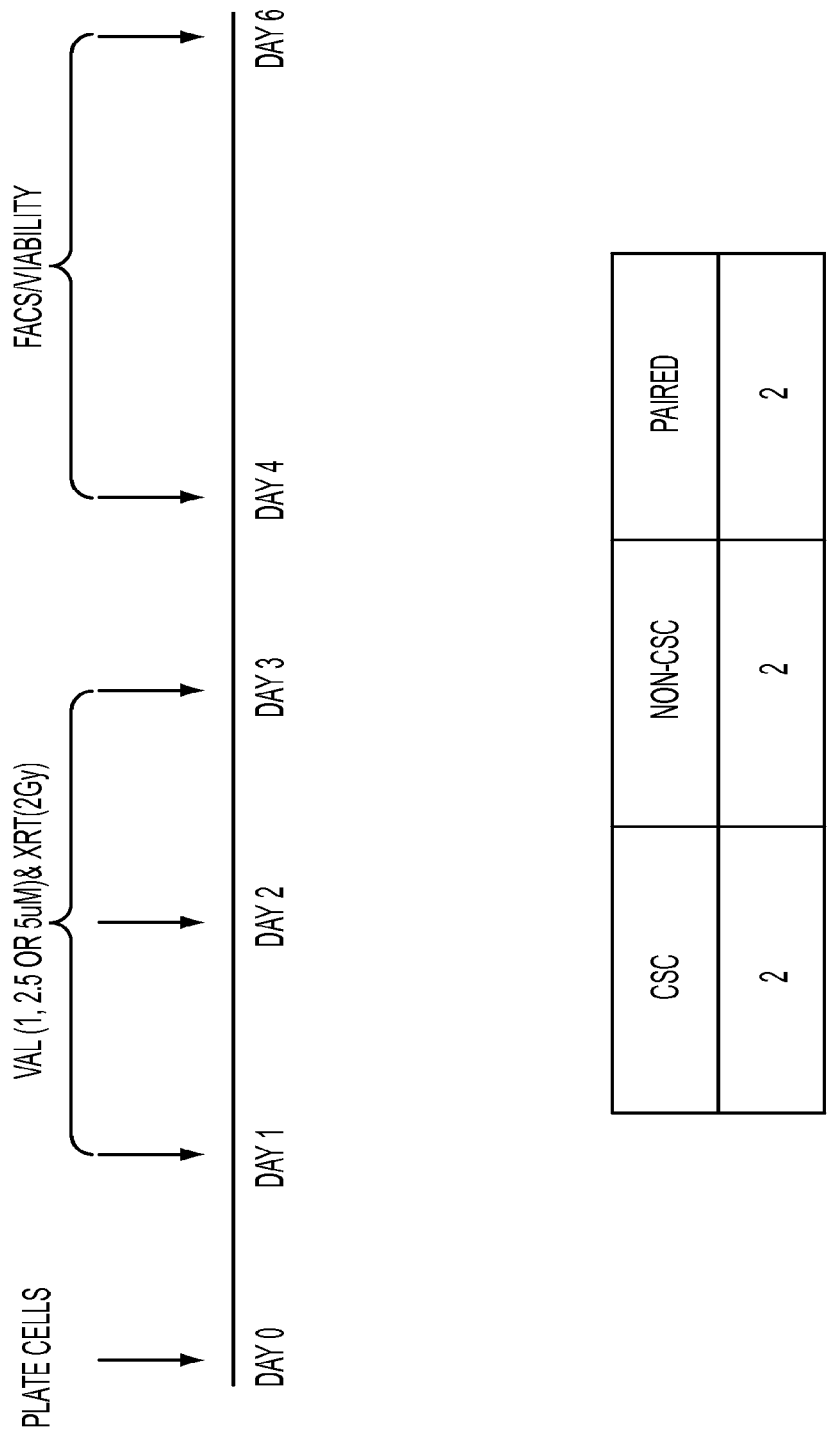

FIG. 25 shows the treatment regimens for combining dianhydrogalactitol ("VAL") and radiation ("XRT").

Figure 26:
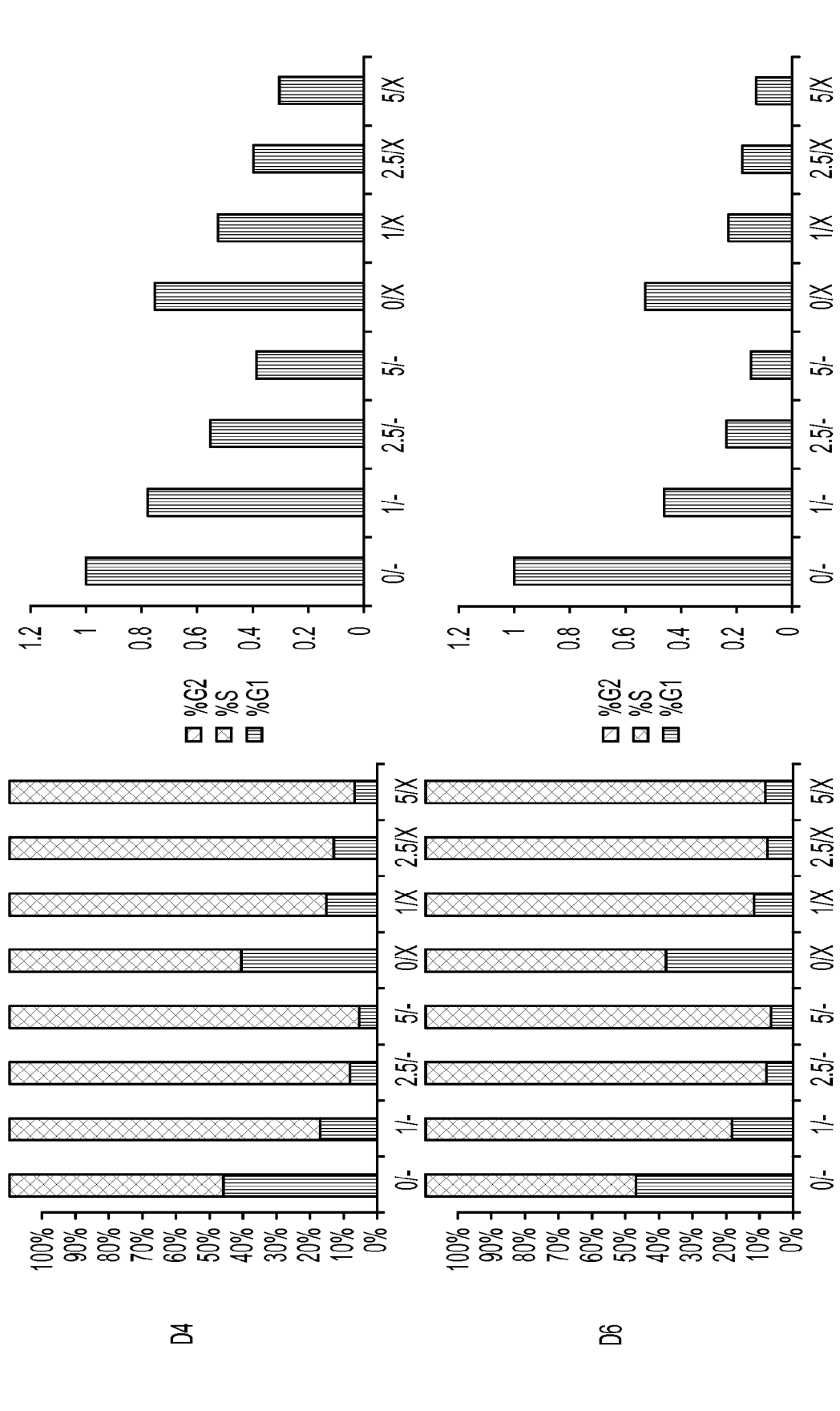

FIG. 26 shows the results for 7996 GNS (CSC) when dianhydrogalactitol is combined with radiation. Results are shown at day 4 ("D4") on the top and day 6 ("D6") on the bottom. The left side shows cell cycle analysis where G2 is shown at the top, S in the middle, and G1 at the bottom. The right side shows cell viability at D4 and D6.

Figure 27:
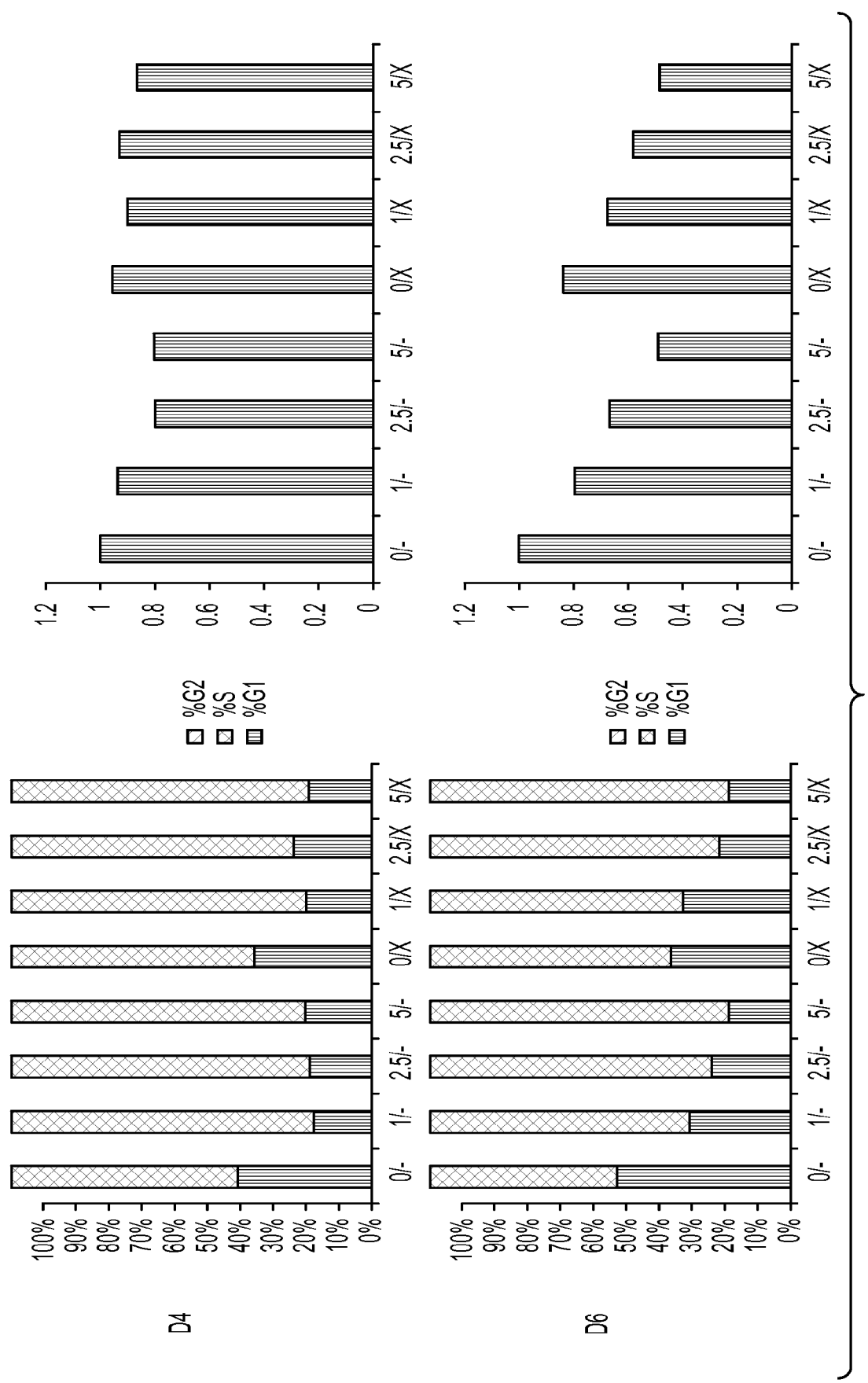

FIG. 27 shows the results for 8565 GNS (CSC) as depicted in FIG. 26.

Figure 28:
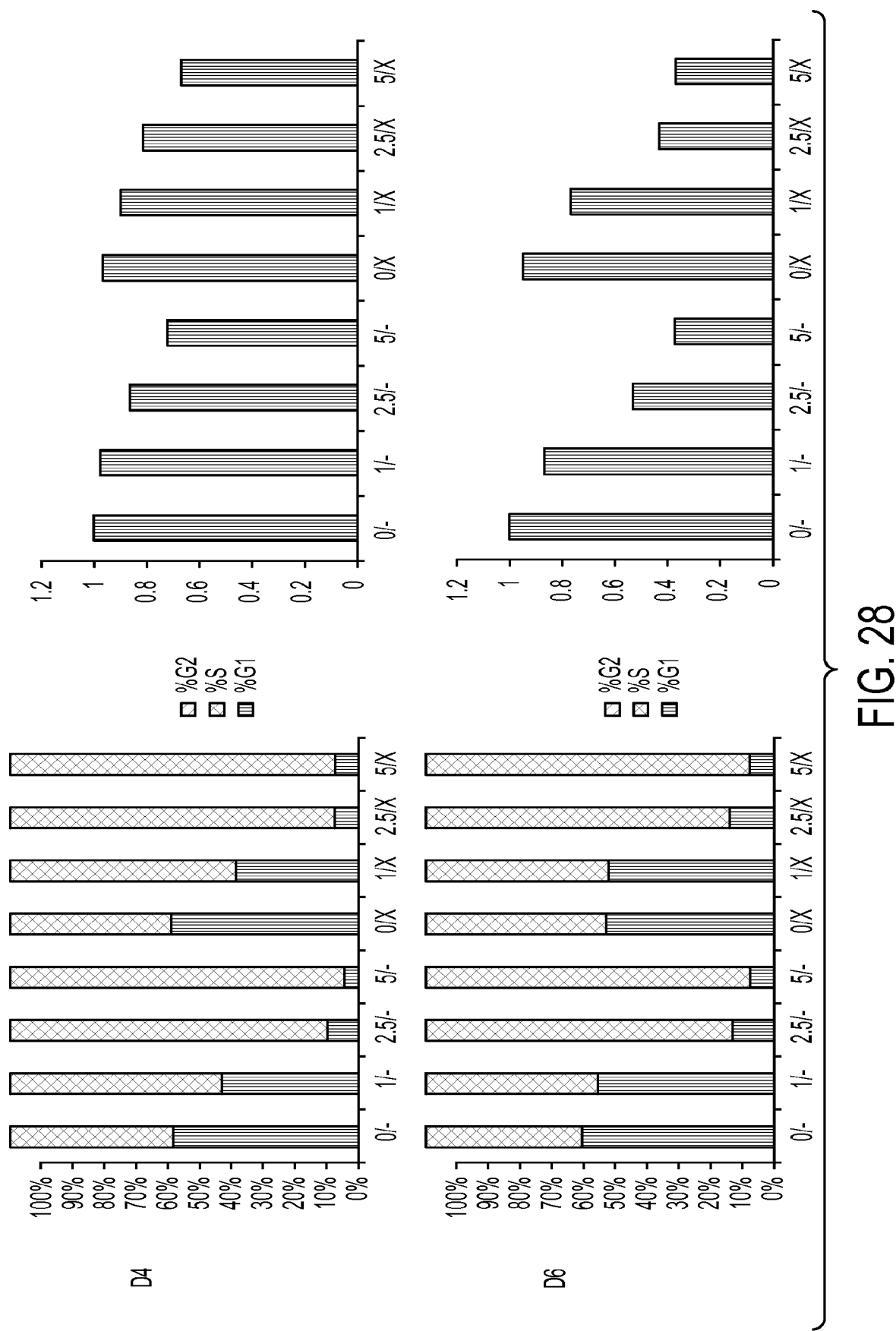

FIG. 28 shows the results for 7996 ML (non-CSC) as depicted in FIG. 26.

Figure 29:
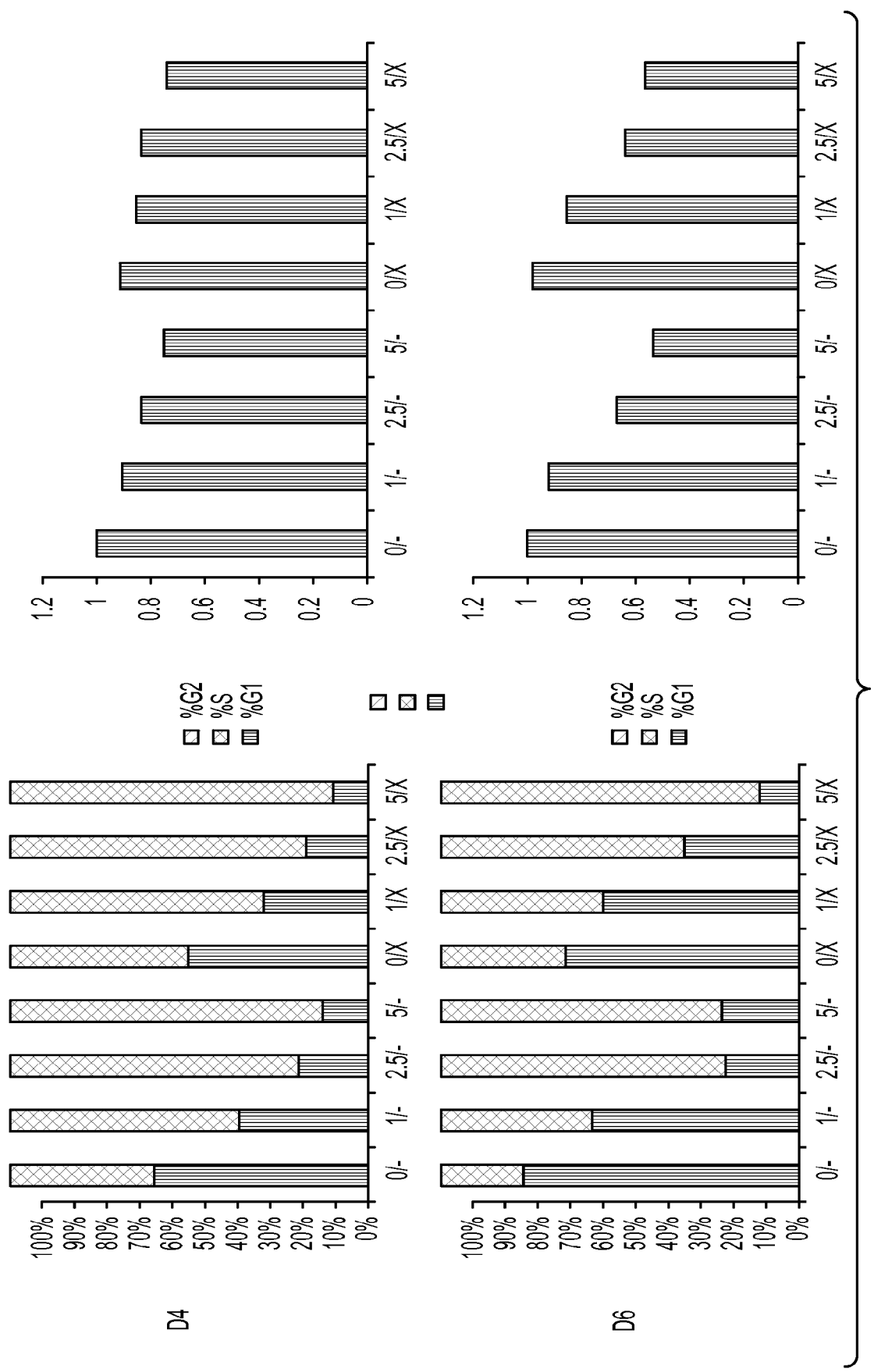

FIG. 29 shows the results for 8565 ML (non-CSC) as depicted in FIG. 26.

Figure 30:
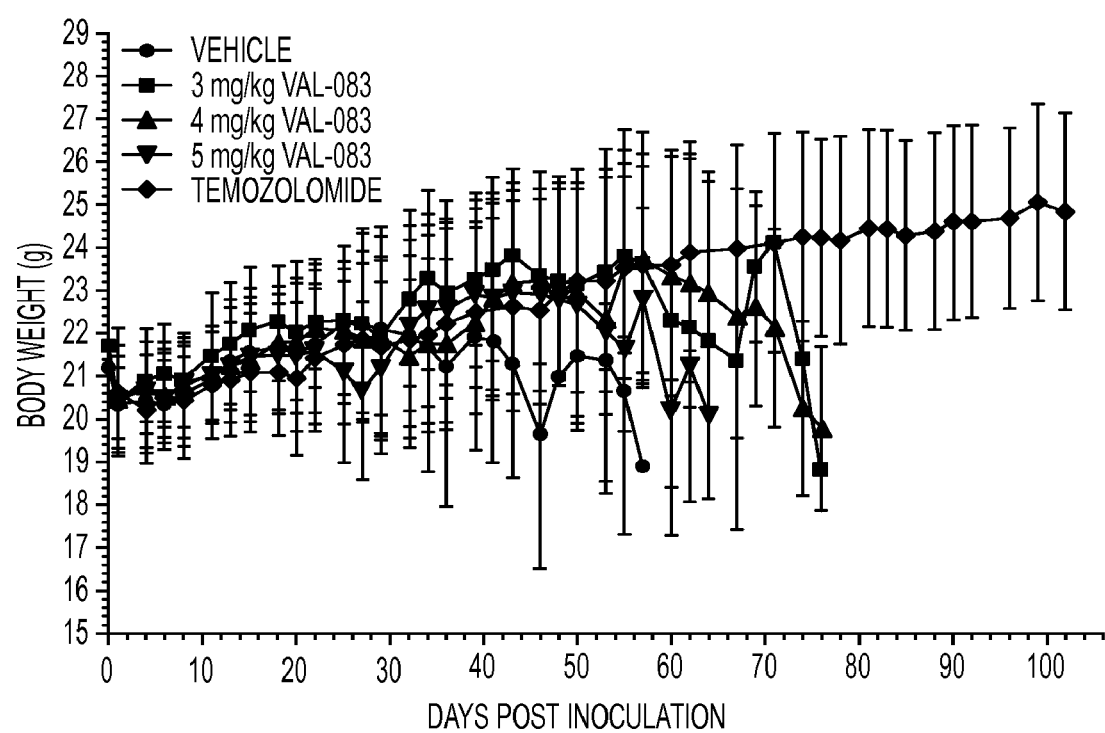

FIG. 30 shows results for body weight as a function of time for female Rag2 mice post-inoculation with U251 GBM cells. Mice were treated with varying concentrations of dianhydrogalactitol ("VAL-083") and with temozolomide (TMZ) (Example 2).

Figure 31:
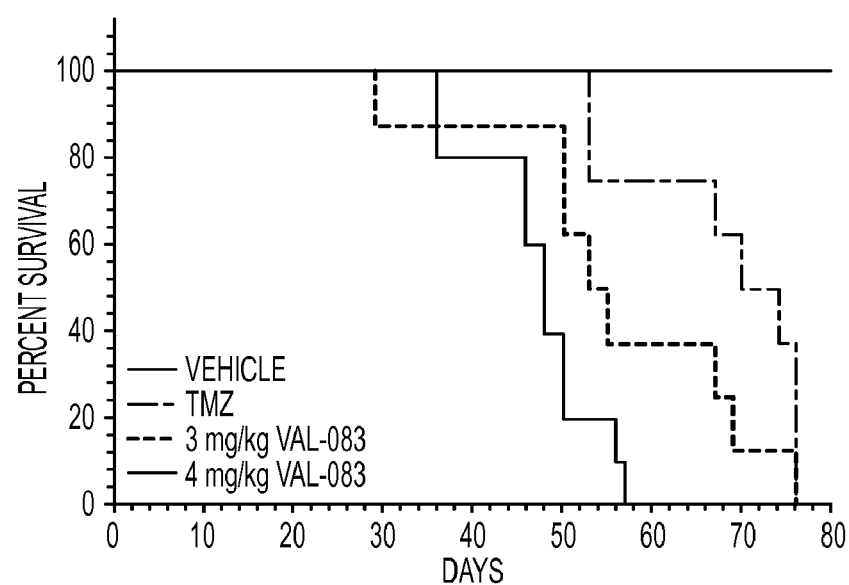

FIG. 31 shows results for survival (Kaplan-Meier plot) for the mice for which results for body weight were shown in FIG. 30 (Example 2).

Figure 2:
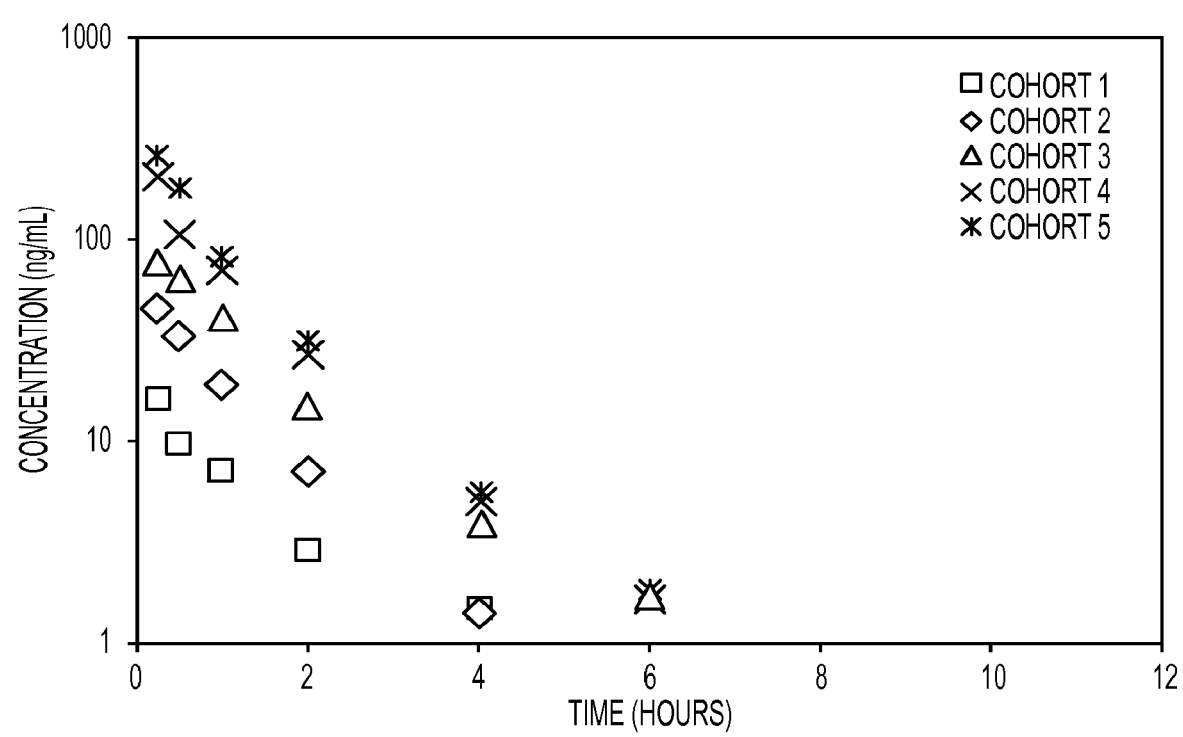
FIG. 2 shows the plasma concentration-time profiles of dianhydrogalactitol in brain tumor patients showing dose-dependent systemic exposure (mean of 3 subjects per cohort).
Figure 32:
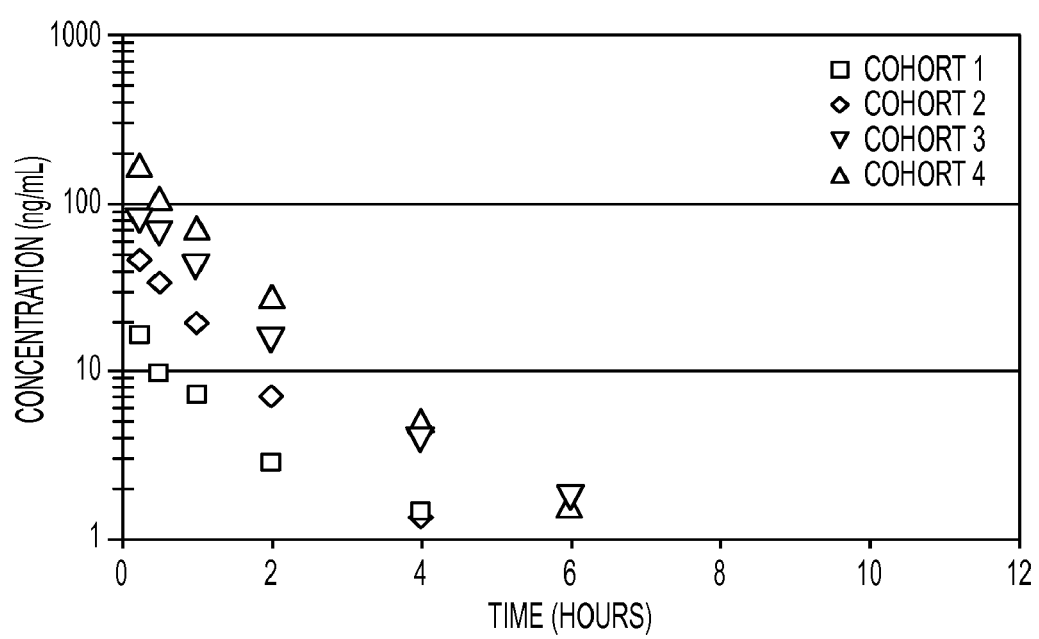

FIG. 32 shows the plasma concentration-time profile of dianhydrogalactitol in glioblastoma multiforme patients (data is shown for an additional cohort as compared with FIG. 2). Four cohorts are shown: ■ is cohort 1; ♦ is cohort 2; ▼ is cohort 3; and ▲ is cohort 4. Concentration (ng/mL) is shown on the y axis; time after administration is shown in the x axis.

DETAILED DESCRIPTION OF THE INVENTION

This invention relates to novel compositions and methods to improve the utility of chemical agents including substituted hexitols such as dianhydrogalactitol or diacetyldianhydrogalactitol with suboptimal performance for patients with cancer, especially malignant gliomas such as glioblastoma multiforme or treatment of progressive secondary brain tumors, such as those arising from metastases of breast adenocarcinoma, small-cell lung carcinoma, or melanoma.

The invention describes the novel development of improved pharmaceutical ingredients, dosage forms, excipients, solvents, diluents, drug delivery systems, preservatives, more accurate drug administrations, improved dose determination and schedules, toxicity monitoring and amelioration, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches, the use of drug delivery systems, novel prodrugs, polymer conjugates, novel routes of administration, other agents to potentiate the activity of the compounds or inhibit the repair of suboptimal cellular effects or sub-lethal damage or to "push" the cell into more destructive cellular phases such as apoptosis. In some cases, the inventive examples include the use of these sub-optimal therapeutics in conjunction with radiation or other conventional chemotherapeutic agents or biotherapeutic agents such as antibodies, vaccines, cytokines, lymphokines, gene and antisense therapies, or other chemotherapeutic or biotherapeutic agents.

By definition, the term "suboptimal therapy" includes agents where Phase I toxicity precluded further human clinical evaluation. It also includes those agents from Phase II trials where limited or no significant tumor responses were identified. In addition, it also includes those agents, the subject of Phase III clinical trials, whose outcome was either medically or statistically not significant to warrant submission or approval by regulatory agencies for commercialization or commercialized agents whose response rates as a monotherapy are less than 25% or whose side-effects are severe enough to limit wider utility. Agents with suboptimal activity include but are not limited to the following: dianhydrogalactitol and diacetyldianhydrogalactitol.

(I) Suboptimal Therapeutics

In general, examples of compounds with suboptimal therapeutic activity include, but are not limited to, compounds of the following classes: DNA/nucleic acid binding/reactive agents, topoisomerase inhibitors, anti-tubulin agents, signal transduction inhibitors, protein synthesis inhibitors, inhibitors of DNA transcribing enzymes, DNA/RNA intercalating agents, DNA minor groove binders, drugs that block steroid hormone action, photochemically active agents, immune modifying agents, hypoxia selective cytotoxins, chemical radiation sensitizers and protectors, antisense nucleic acids, oligonucleotides and polynucleotides therapeutic agents, immune modifying agents, antitumor antibiotics, biotherapeutics, biologic agents such as cancer vaccines, antibody therapies, cytokines, lyphokines, gene therapies, nucleic acid therapies, and cellular therapies. In some cases, a compound may fall within more than one of these classes; such compounds are also within the scope of the invention.

In some cases, compounds or compositions may be in current clinical use for one or more indications, but yet be considered suboptimal for another indication, such as a different type of malignancy, either in terms of the cell type involved in the malignancy or in terms of the stage of the malignancy. Such compounds or compositions are within the scope of the invention. Particular examples include dianhydrogalactitol, diacetyldianhydrogalactitol, and derivatives and analogs thereof.

In particular, the invention is directed to galactitols, substituted galactitols, and derivatives or analogs thereof, including dianhydrogalactitol and diacetyldianhydrogalactitol and derivatives or analogs thereof.

The structure of dianhydrogalactitol is shown in Formula (I), below.

(I)

Also within the scope of the invention are derivatives or analogs of dianhydrogalactitol that, for example, have the hydrogen of the hydroxyl groups replaced with lower alkyl, have the hydrogen attached to the epoxide ring replaced with lower alkyl, or have the methyl groups attached to the same carbons that bear the hydroxyl groups replaced with lower alkyl or substituted with, for example, halo groups.

The structure of diacetyldianhydrogalactitol is shown in Formula (II), below.

(II)

Also within the scope of the invention are derivatives or analogs of diacetyldianhydrogalactitol that, for example, have the methyl groups that are part of the acetyl moieties replaced with lower alkyl, have the hydrogen attached to the epoxide ring replaced with lower alkyl, or have the methyl groups attached to the same carbons that bear the acetyl groups replaced with lower alkyl or substituted with, for example, halo groups.

A particularly suitable derivative or analog of dianhydrogalactitol is a derivative of dianhydrogalactitol that is selected from the group consisting of: (i) a derivative of dianhydrogalactitol that has one or both of the hydrogens of the two hydroxyl groups of dianhydrogalactitol replaced with lower alkyl; (ii) a derivative of dianhydrogalactitol that has one or more of the hydrogens attached to the two epoxide rings replaced with lower alkyl; (iii) a derivative of dianhydrogalactitol that has one or both of the methyl groups present in dianhydrogalactitol and that are attached to the same carbons that bear the hydroxyl groups replaced with $C_2$-$C_6$ lower alkyl; and (iv) a derivative of dianhydrogalactitol that has one or both of the methyl groups present in dianhydrogalactitol and that are attached to the same carbons that bear the hydroxyl groups substituted with a halo group by replacing a hydrogen of the methyl group with a halo group.

A particularly suitable derivative or analog of diacetyldianhydrogalactitol is a derivative of diacetyldianhydrogalactitol that is selected from the group consisting of: (i) a derivative of diacetyldianhydrogalactitol that has one or both of the methyl groups that are part of the acetyl moieties replaced with $C_2$-$C_6$ lower alkyl; (ii) a derivative of diacetyldianhydrogalactitol that has one or both of the hydrogens attached to the epoxide ring replaced with lower alkyl; (iii) a derivative of diacetyldianhydrogalactitol that has one or both of the methyl groups attached to the same carbons that bear the acetyl groups replaced with $C_2$-$C_6$ lower alkyl; and (iv) a derivative of diacetyldianhydrogalactitol that has one or both of the methyl groups that are attached to the same carbons that bear the hydroxyl groups substituted with a halo group by replacing a hydrogen of the methyl group with a halo group.

Other derivatives and analogs are known in the art. These derivatives or analogs can be optionally substituted with one or more groups that do not substantially affect the pharmacological activity of the derivative or analog. These groups are generally known in the art. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicyclic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valiences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, =S⁻, —$NZ^cZ^c$, =$NZ^b$, =N—$OZ^b$, trihalomethyl, —$CF_3$, —CN, —OCN, —SCN, —NO, —$NO_2$, =$N_2$, —$N_3$, —$S(O)_2Z^b$, —$S(O)_2NZ^b$, —$S(O_2)O^-$, —$S(O_2)OZ^b$, —$OS(O_2)OZ^b$, —$OS(O_2)O^-$, —$OS(O_2)OZ^b$, —$P(O)(O^-)_2$, —$P(O)(OZ^b)$ ($O^-$), —$P(O)(OZ^b)(OZ^b)$, —$C(O)Z^b$, —$C(S)Z^b$, —$C(NZ^b)Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)Z^b$, —$NZ^bC(S)Z^b$, —$NZ^bC(O)O^-$, —$NZ^bC(O)OZ^b$, —$NZ^bC(S)OZ^b$, —$NZ^bC(O)NZ^cZ^c$, —$NZ^bC(NZ^b)Z^b$, —$NZ^bC(NZ^b)NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —$NZ^cZ^c$ is meant to include —$NH_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)$OZ^b$, -alkylene-C(O)$NZ^bZ^b$, and —$CH_2$—$CH_2$—C(O)—$CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —$Z^a$, halo, —$O^-$, —$OZ^b$, —$SZ^b$, —S—, —$NZ^cZ^c$, trihalomethyl, —$CF_3$, —CN, —OCN, —SCN, —NO, —$NO_2$, —$N_3$, —$S(O)_2Z^b$, —$S(O_2)O^-$, —$S(O_2)OZ^b$, —$OS(O_2)OZ^b$, —$OS(O_2)O^-$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, —$Z^a$, halo, —$O^-$, —$OZ^b$, —$SZ^b$, —S—, —$NZ^cZ^c$, trihalomethyl, —$CF_3$, —CN, —OCN, —SCN, —NO, —$NO_2$, —$S(O)_2Z^b$, —$S(O_2)O^-$, —$S(O_2)OZ^b$, —$OS(O_2)OZ^b$, —$OS(O_2)O^-$, —$P(O)(O^-)_2$, —$P(O)(OZ^b)(O^-)$, —$P(O)(OZ^b)(OZ^b)$, —$C(O)Z^b$, —$C(S)$ $Z^b$, —$C(NZ^b)Z^b$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)OZ^b$, —$OC(S)OZ^b$, —$NZ^bC(O)Z^b$, —$NZ^bC(S)Z^b$, —$NZ^bC(O)$ $OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers, unless the invention is specifically limited to one or more stereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures, unless the invention is specifically limited to one or more stereoisomers. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds, unless specifically restricted to one tautomer. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolyzable esters of the present compounds are the compounds whose carboxyls are present in the form of hydrolysable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the "hetero" terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —NH$_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C═O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—SO$_3$H) substituent.

As used herein, the term "sulfamoyl" refers to a substituent with the structure —S(O$_2$)NH$_2$, wherein the nitrogen of the NH$_2$ portion of the group can be optionally substituted as described above.

As used herein, the term "carboxyl" refers to a group of the structure —C(O$_2$)H.

As used herein, the term "carbamyl" refers to a group of the structure —C(O$_2$)NH$_2$, wherein the nitrogen of the NH$_2$ portion of the group can be optionally substituted as described above.

As used herein, the terms "monoalkylaminoalkyl" and "dialkylaminoalkyl" refer to groups of the structure -Alk$_1$-NH-Alk$_2$ and -Alk$_1$-N(Alk$_2$)(Alk$_3$), wherein Alk$_1$, Alk$_2$, and Alk$_3$ refer to alkyl groups as described above.

As used herein, the term "alkylsulfonyl" refers to a group of the structure —S(O)$_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —S(O)$_2$—Ar wherein Ar refers to an aryl group as described above. The term "aryloxyalkylsulfonyl" refers to a group of the structure —S(O)$_2$-Alk-O—Ar, where Alk is an alkyl group as described above and Ar is an aryl group as described above. The term "arylalkylsulfonyl" refers to a group of the structure —S(O)$_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is CH$_3$CH$_2$OC(O)—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

Dianhydrogalactitol and other substituted hexitols possess a number of advantages for use in recurrent malignant glioma and progressive secondary brain tumor, as well as other malignancies. These agents can suppress the growth of cancer stem cells (CSC) and are resistant to drug inactivation by O$^6$-methylguanine-DNA methyltransferase (MGMT). Dianhydrogalactitol is a novel alkylating agent that causes crosslinking of DNA at N$^7$.

The hexitol derivative, such as dianhydrogalactitol, a derivative or analog of dianhydrogalactitol, diacetyldianhydrogalactitol, or a derivative or analog or diacetyldianhydrogalactitol, can be administered in a pharmaceutical composition wherein the pharmaceutical composition comprises at least one excipient, solvent, filler, diluent, buffer, preservative, or additive in addition to the hexitol derivative. Further details on pharmaceutical compositions suitable for use in methods according to the present invention are described below.

Typically, the malignancy is selected from the group consisting of recurrent glioma and progressive secondary brain tumor. Typically, the recurrent glioma is glioblastoma multiforme. Typically, the glioblastoma multiforme is substantially resistant to at least one of temozolomide and bevacizumab. Typically, the progressive secondary brain tumor is a metastasis of a malignancy selected from the group consisting of adenocarcinoma of the breast, small-cell lung carcinoma, and melanoma.

Due to prior chemotherapy and radiation therapy, patients with secondary brain tumors are likely more prone to myelosuppression and may have a different MTD (maximum tolerated dose) than patients with GBM. This can be determined by assessing function of the immune system and monitoring possible myelosuppression. Myelosuppression can be monitored by determining concentrations of at least one of erythrocytes, leukocytes, or platelets. Methods for monitoring or determining the existence or severity of myelosuppression are known in the art and are described, for example, in J. E. Higgs et al., "Are Patients with Intermediate TPMT Activity at Increased Risk for Myelosuppression When Taking Thiopurine Medications," *Pharmacogenomics* 11: 177-188 (2010), incorporated herein by this reference.

(II) Dose Modification

Improvements for suboptimal chemotherapeutics including substituted hexitols such as dianhydrogalactitol or diacetyldianhydrogalactitol are made by alterations to the time that the compound is administered, the use of dose-modifying agents that control the rate of metabolism of the compound, normal tissue protective agents, and other alterations. General examples include: variations of infusion schedules (e.g., bolus i.v. versus continuous infusion), the use of lymphokines (e.g., G-CSF, GM-CSF, EPO) to increase leukocyte count for improved immune response or for preventing anemia caused by myelosuppressive agents, or the use of rescue agents such as leucovorin for 5-FU or thiosulfate for cisplatin treatment. Specific inventive examples for substituted hexitols such as dianhydrogalactitol or diacetyldianhydrogalactitol for treatment of a malignancy such as recurrent malignant glioma or progressive secondary brain tumor include: continuous i.v. infusion for hours to days; biweekly administration; doses greater than 5 mg/m$^2$/day; progressive escalation of dosing from 1 mg/m$^2$/day based on patient tolerance; use of caffeine to modulate metabolism; use of isonazid to modulate metabolism; selected and intermittent boosting of dosage administration; administration of single and multiple doses escalating from 5 mg/m$^2$/day via bolus; oral dosages of below 30 mg/m$^2$; oral dosages of above 130 mg/m$^2$; oral dosages up to 40 mg/m$^2$ for 3 days and then a nadir/recovery period of 18-21 days; oral dosages up to 50 mg/m$^3$ for 3 days and then a nadir/recovery period of 18-21 days; dosing at a lower level for an extended period (e.g., 21 days); dosing at a higher level; dosing with a nadir/recovery period longer than 21 days; the use of an alkylating hexitol derivative as a single cytotoxic agent; immediate release dosing; slow release dosing; controlled release dosing; dosage reduction to control or limit reduction of function of the immune system; dosage reduction to control or limit myelosuppression; a dose of 1.5 mg/m$^2$ (cumulative dose 9 mg/m$^2$ in a 33-day cycle); a dose of 3.0 mg/m$^2$ (cumulative dose 18 mg/m$^2$ in a 33-day cycle); a dose of 5.0 mg/m$^2$ (cumulative dose 30 mg/m$^2$ in a 33-day cycle); a dose of 10 mg/m$^2$ (cumulative dose 60 mg/m$^2$ in a 33-day cycle); a dose of 15 mg/m$^2$ (cumulative dose 90 mg/m$^2$ in a 33-day cycle); a dose of 20 mg/m$^2$ (cumulative dose 120 mg/m$^2$ in a 33-day cycle); a dose of 25 mg/m$^2$ (cumulative dose 150 mg/m$^2$ in a 33-day cycle); a dose of 30 mg/m$^2$ (cumulative dose 180 mg/m$^2$ in a 33-day cycle); a dose of 40 mg/m$^2$ (cumulative dose 240 mg/m$^2$ in 33-day cycle); a dose beginning at 1.5 mg/m$^2$ and increasing to 3.0 mg/m$^2$; a dose beginning at 1.5 mg/m$^2$, increasing to 3.0 mg/m$^2$, then increasing to 5.0 mg/m$^2$; a dose beginning at 1.5 mg/m$^2$, increasing to 3.0 mg/m$^2$, then increasing to 5.0 mg/m$^2$, then increasing to 10 mg/m$^2$; a dose beginning at 1.5 mg/m$^2$, increasing to 3.0 mg/m$^2$, then increasing to 5.0 mg/m$^2$, then increasing to 10 mg/m$^2$, then increasing to 15 mg/m$^2$; a dose beginning at 1.5 mg/m$^2$, increasing to 3.0 mg/m$^2$, then increasing to 5.0 mg/m$^2$, then increasing to 10 mg/m$^2$; then increasing to 15 mg/m$^2$, then increasing to 20 mg/m$^2$; a dose beginning at 1.5 mg/m$^2$, increasing to 3.0 mg/m$^2$, then increasing to 5.0 mg/m$^2$, then increasing to 10 mg/m$^2$; then increasing to 15 mg/m$^2$, then increasing to 20 mg/m$^2$, then increasing to 25 mg/m$^2$; a dose beginning at 1.5 mg/m$^2$, increasing to 3.0 mg/m$^2$, then increasing to 5.0 mg/m$^2$, then increasing to 10 mg/m$^2$, then increasing to 15 mg/m$^2$, then increasing to 20 mg/m$^2$, then increasing to 25 mg/m$^2$, then increasing to 30 mg/m$^2$; a dose beginning at 1.5 mg/m$^2$, increasing to 3.0 mg/m$^2$, then increasing to 5.0 mg/m$^2$, then increasing to 10 mg/m$^2$, then increasing to 15 mg/m$^2$, then increasing to 20 mg/m$^2$, then increasing to 25 mg/m$^2$, then increasing to 30 mg/m$^2$, then increasing to 40 mg/m$^2$; and a dose beginning at 1.5 mg/m$^2$, increasing to 3.0 mg/m$^2$, then increasing to 5.0 mg/m$^2$, then increasing to 10 mg/m$^2$, then increasing to 15 mg/m$^2$, then increasing to 20 mg/m$^2$, then increasing to 25 mg/m$^2$, then increasing to 30 mg/m$^2$, then increasing to 40 mg/m$^2$; and then increasing to 50 mg/m$^2$. Due to prior chemotherapy and radiation therapy, patients with secondary brain tumors are likely more prone to myelosuppression and may have a different MTD (maximum tolerated dose) than patients with GBM. This can be determined by assessing function of the immune system and monitoring possible myelosuppression. Dosages can then be adjusted if required to maintain function of the immune system or prevent myelosuppression.

(III) Route of Administration

Improvements for suboptimal chemotherapeutics including substituted hexitols such as dianhydrogalactitol or diacetyldianhydrogalactitol are made by alterations in the route by which the compound is administered. General examples include: changing route from oral to intravenous administration and vice versa; or the use of specialized routes such as subcutaneous, intramuscular, intraarterial, intraperitoneal, intralesional, intralymphatic, intratumoral, intrathecal, intravesicular, intracranial. Specific inventive examples for substituted hexitols such as dianhydrogalactitol or diacetyldianhydrogalactitol for treatment of a malignancy such as recurrent malignant glioma or progressive secondary brain tumor include: topical administration; oral administration; slow release oral delivery; intrathecal administration; intraarterial administration; administration by continuous infusion; or administration by intermittent infusion.

(IV) Schedule of Administration

Improvements for suboptimal chemotherapeutics including substituted hexitols such as dianhydrogalactitol or diacetyldianhydrogalactitol are made by alterations to the time that the compound is administered. General examples include: changing from a monthly administration to a weekly or daily dosing or variations of the schedule. Specific inventive examples for substituted hexitols such as dianhydrogalactitol or diacetyldianhydrogalactitol for treatment of a malignancy such as recurrent malignant glioma or progressive secondary brain tumor include: daily; weekly for three weeks, weekly for two weeks, biweekly; biweekly for three weeks with a 1-2 week rest period; intermittent boost dose administration; daily for one week then once per week for multiple weeks; dosing at up to 50 mg/m$^2$ for 3 days and then a nadir/recovery period of 18 to 21 days (dosages can be at 25 mg/m$^2$/day, 40 mg/m$^2$/day, or 50 mg/m$^2$/day);

dosing at a lower level for extended periods (e.g., 21 days); dosing at a higher level; dosing with a nadir/recovery period longer than 21 days; or the use of an alkylating hexitol derivative as a single therapeutic agent. A particularly suitable dose schedule is once daily for three consecutive days every 21 days; dosages for this dose schedule are as described above and can be increased in stages.

(V) Disease Stages

Improvements for suboptimal chemotherapeutics including substituted hexitols such as dianhydrogalactitol or diacetyldianhydrogalactitol are made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for substituted hexitols such as dianhydrogalactitol or diacetyldianhydrogalactitol include: use for the treatment of recurrent malignant glioma such as glioblastoma multiforme or use for the treatment of progressive secondary brain tumor such as that caused by metastases of breast adenocarcinoma, small-cell lung carcinoma, or melanoma.

(VI) Patient Selection

Improvements for suboptimal chemotherapeutics including substituted hexitols such as dianhydrogalactitol or diacetyldianhydrogalactitol are made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other conditions that may uniquely exploit a feature of the compound. Specific inventive examples for substituted hexitols such as dianhydrogalactitol or diacetyldianhydrogalactitol for treatment of a malignancy such as recurrent malignant glioma or progressive secondary brain tumor include: patients with disease conditions with high levels of metabolic enzymes, histone deacetylase, protein kinases, ornithine decarboxylase; patients with disease conditions with low levels of metabolic enzymes, histone deacetylase, protein kinases, ornithine decarboxylase; patients with low or high susceptibility to thrombocytopenia, neutropenia; patients intolerant of GI toxicities; over- or under-expression of jun, GPCR's and signal transduction proteins, VEGF, prostate specific genes, protein kinases, or telomerase.

(VII) Patient/Disease Phenotype

Improvements for suboptimal chemotherapeutics including substituted hexitols such as dianhydrogalactitol or diacetyldianhydrogalactitol are made by more precise identification of a patient's ability to tolerate, metabolize and exploit the use of the compound. General examples include: use of diagnostic tools and kits to better characterize a patient's ability to process/metabolize a chemotherapeutic agent or their susceptibility to toxicity caused by potential specialized cellular, metabolic, organ system phenotypes: Specific inventive examples for substituted hexitols such as dianhydrogalactitol or diacetyldianhydrogalactitol for treatment of a malignancy such as recurrent malignant glioma or progressive secondary brain tumor include: diagnostic tools, techniques, kits and assays to confirm a patient's particular phenotype and for the measurement of metabolism enzymes and metabolites, histone deacetylase, protein kinases, ornithine decarboxylase, VEGF, prostate specific genes, protein kinases, telomerase, jun GPCR's; surrogate compound dosing or low dose drug pre-testing for enzymatic status.

(VIII) Patient/Disease Genotype

Improvements for suboptimal chemotherapeutics including substituted hexitols such as dianhydrogalactitol or diacetyldianhydrogalactitol are made by testing and analyzing a patient's genotype for unique features that may be of value to predict efficacy, toxicity, metabolism, or other factors affecting the therapeutic efficacy of the drug. General examples include: biopsy samples of tumors or normal tissues (e.g., white blood cells) that may also be taken and analyzed to specifically tailor or monitor the use of a particular drug against a gene target; studies of unique tumor gene expression patterns; or analysis of SNPs (single nucleotide polymorphisms), to enhance efficacy or to avoid particular drug-sensitive normal tissue toxicities. Specific inventive examples for substituted hexitols such as dianhydrogalactitol or diacetyldianhydrogalactitol for treatment of a malignancy such as recurrent malignant glioma or progressive secondary brain tumor include: diagnostic tools, techniques, kits and assays to confirm a patient's particular genotype; gene/protein expression chips and analysis; Single Nucleotide Polymorphisms (SNPs) assessment; SNPs for histone deacetylase, ornithine decarboxylase, GPCRs, protein kinases, telomerase, jun: identification and the measurement of metabolism enzymes and metabolites.

(IX) Pre/Post-Treatment Preparation

Improvements for suboptimal chemotherapeutics including substituted hexitols such as dianhydrogalactitol or diacetyldianhydrogalactitol are made by specialized preparation of a patient prior to or after the use of a chemotherapeutic agent. General examples include: induction or inhibition of metabolizing enzymes, specific protection of sensitive normal tissues or organ systems. Specific inventive examples for substituted hexitols such as dianhydrogalactitol or diacetyldianhydrogalactitol for treatment of a malignancy such as recurrent malignant glioma or progressive secondary brain tumor include: the use of colchicine or analogs; use of diuretics such as probenecid; use of uricase; non-oral use of nicotinamide; sustained release forms of nicotinamide; use of inhibitors of polyADP ribose polymerase; use of caffeine; leucovorin rescue; infection control; antihypertensives.

(X) Toxicity Management

Improvements for suboptimal chemotherapeutics including substituted hexitols such as dianhydrogalactitol or diacetyldianhydrogalactitol are made by use of additional drugs or procedures to prevent or reduce potential side-effects or toxicities. General examples include: the use of anti-emetics, anti-nausea, hematological support agents to limit or prevent neutropenia, anemia, thrombocytopenia, vitamins, antidepressants, treatments for sexual dysfunction, and other supportive techniques. Specific inventive examples for substituted hexitols such as dianhydrogalactitol or diacetyldianhydrogalactitol for treatment of a malignancy such as recurrent malignant glioma or progressive secondary brain tumor include: the use of colchicine or analogs; use of diuretics such as probenecid; use of uricase; non-oral use of nicotinamide; sustained release forms of nicotinamide; use of inhibitors of poly ADP-ribose polymerase; use of caffeine; leucovorin rescue; use of sustained release allopurinol; non-oral use of allopurinol; bone marrow transplant stimulants, blood, platelet infusions, Neupogen, G-CSF; GM-CSF; pain management; anti-inflammatories; fluids; corticosteroids; insulin control medications; anti-pyretics; anti-nausea treatments; anti-diarrhea treatment; N-acetylcysteine, antihistamines.

(XI) Pharmacokinetic/Pharmacodynamic Monitoring

Improvements for suboptimal chemotherapeutics including substituted hexitols such as dianhydrogalactitol or diacetyldianhydrogalactitol are made by the use of monitoring drug levels after dosing in an effort to maximize a patient's drug plasma level, to monitor the generation of toxic metabolites, monitoring of ancillary medicines that could be beneficial or harmful in terms of drug-drug interactions. General examples include: the monitoring of drug plasma protein binding, and monitoring of other pharmacokinetic or pharmacodynamic variables. Specific inventive examples for substituted hexitols such as dianhydrogalactitol or diacetyldianhydrogalactitol for treatment of a malignancy such as recurrent malignant glioma or progressive secondary brain tumor include: multiple determinations of drug plasma levels; or multiple determinations of metabolites in the blood or urine.

(XII) Drug Combinations

Improvements for suboptimal chemotherapeutics including substituted hexitols such as dianhydrogalactitol or diacetyldianhydrogalactitol are made by exploiting unique drug combinations that may provide a more than additive or synergistic improvement in efficacy or side-effect management. General examples include: alkylating agents with anti-metabolites, topoisomerase inhibitors with antitubulin agents. Specific inventive examples for substituted hexitols such as dianhydrogalactitol or diacetyldianhydrogalactitol for treatment of a malignancy such as recurrent malignant glioma or progressive secondary brain tumor include: in combination with topoisomerase inhibitors; use with fraudulent nucleosides; use with fraudulent nucleotides; use with thymidylate synthetase inhibitors; use with signal transduction inhibitors; use with cisplatin or platinum analogs; use with alkylating agents such as the nitrosoureas (BCNU, Gliadel wafers, CCNU, nimustine (ACNU), bendamustine (Treanda)); use with alkylating agents that damage DNA at a different place than does dianhydrogalactitol or another alkylating hexitol derivative (TMZ, BCNU, CCNU, and other alkylating agents all damage DNA at $O^6$ of guanine, whereas dianhydrogalactitol cross-links at $N^7$); use with a monofunctional alkylating agent; use with a bifunctional alkylating agent; use with anti-tubulin agents; use with antimetabolites; use with berberine; use with apigenin; use with amonafide; use with colchicine or an analog thereof; use with genistein; use with etoposide; use with cytarabine; use with campothecins; use with vinca alkaloids; use with topoisomerase inhibitors; use with 5-fluorouracil; use with curcumin; use with NF-κB inhibitors; use with rosmarinic acid; use with mitoguazone; use with tetrandrine; use with temozolomide (TMZ); use in combination with biological therapies such as antibodies such as Avastin (a VEGF inhibitor), Rituxan, Herceptin, Erbitux; use in combination with cancer vaccine therapy; use with epigenetic modulators; use with transcription factor inhibitors; use with taxol; use with homoharringtonine; use with pyridoxal; use with spirogermanium; use with caffeine; use with nicotinamide; use with methylglyoxalbisguanylhydrazone; use with Rho kinase inhibitors; use with 1,2,4-benzotriazine oxides; use with an alkylglycerol; use with an inhibitor of a Mer, Ax1, or Tyro-3 receptor kinase; use with an inhibitor of ATR kinase; use with a modulator of Fms kinase, Kit kinase, MAP4K4 kinase, TrkA kinase, or TrkB kinase; use with endoxifen; use with a mTOR inhibitor; use with an inhibitor of Mnk1a kinase, Mkn1b kinase, Mnk2a kinase, or Mnk2b kinase; use with a modulator of pyruvate kinase M2; use with a modulator of phosphoinositide 3-kinases; use with a cysteine protease inhibitor; use with phenformin; use with Sindbis virus-based vectors; use with peptidomimetics that act as mimetics of Smac and inhibit IAPs to promote apoptosis; use with a Raf kinase inhibitor; use with a nuclear transport modulator; use with an acid ceramidase inhibitor and a choline kinase inhibitor; use with tyrosine kinase inhibitors; use with anti-CS1 antibodies; use with inhibitors of protein kinase CK2; use with anti-guanylyl cyclase C (GCC) antibodies; use with histone deacetylase inhibitors; use with cannabinoids; use with glucagon-like peptide-1 (GLP-1) receptor agonists; use with inhibitors of Bcl-2 or Bcl-xL; use with Stat3 pathway inhibitors; use with inhibitors of polo-like kinase 1 (Plk1); use with GBPAR1 activators; use with modulators of serine-threonine protein kinase and poly(ADP-ribose) polymerase (PARP) activity; use with taxanes; use with inhibitors of dihydrofolate reductase; use with inhibitors of aromatase; use with benzimidazole-based anti-neoplastic agents; use with an 06-methylguanine-DNA-methyltransferase (MGMT) inhibitor; use with CCR9 inhibitors; use with acid sphingomyelinase inhibitors; use with peptidomimetic macrocycles; use with cholanic acid amides; use with substituted oxazaphosphorines; use with anti-TWEAK receptor antibodies; use with an ErbB3 binding protein; use with a glutathione S-transferase-activated anti-neoplastic compound; use with substituted phosphorodiamidates; use with inhibitors of MEKK protein kinase; use with COX-2 inhibitors; use with cimetidine and a cysteine derivative; use with anti-IL-6 receptor antibody; use with an antioxidant; use with an isoxazole inhibitor of tubulin polymerization; use with PARP inhibitors; use with Aurora protein kinase inhibitors; use with peptides binding to prostate-specific membrane antigen; use with CD19 binding agents; use with benzodiazepines; use with Toll-like receptor (TLR) agonists; use with bridged bicyclic sulfamides; use with inhibitors of epidermal growth factor receptor kinase; use with a ribonuclease of the T2 family having actin-binding activity; use with myrsinoic acid A or an analog thereof; use with inhibitors of a cyclin-dependent kinase; use with inhibitors of the interaction between p53 and MDM2; use with inhibitors of the receptor tyrosine kinase MET; use with largazole or largazole analogs; use with inhibitors of AKT protein kinase; use with 2'-fluoro-5-methyl-β-L-arabinofuranosyluridine or L-deoxythymidine; use with HSP90 modulators; use with inhibitors of JAK kinases; use with inhibitors of PDK1 protein kinase; use with PDE4 inhibitors; use with inhibitors of proto-oncogene c-Met tyrosine kinase; use with inhibitors of indoleamine 2,3-dioxygenase; use with agents that inhibit expression of ATDC (TRIM29); use with proteomimetic inhibitors of the interaction of nuclear receptor with coactivator peptides; use with antagonists of XIAP family proteins; use with tumor-targeted superantigens; use with inhibitors of Pim kinases; use with inhibitors of CHK1 or CH2 kinases; use with inhibitors of angiopoietin-like 4 protein; use with Smo antagonists; use with nicotinic acetylcholine receptor antagonists; use with farnesyl protein transferase inhibitors; use with adenosine A3 receptor antagonists; use with cancer vaccines; use with a JAK2 inhibitor; use with a Src inhibitor; or use with an agent that suppresses growth or replication of glioma cancer stem cells.

(XIII) Chemosensitization

Improvements for suboptimal chemotherapeutics including substituted hexitols such as dianhydrogalactitol or diacetyldianhydrogalactitol are made by exploiting them as chemosensitizers where no measurable activity is observed when used alone but in combination with other therapeutics a more than additive or synergistic improvement in efficacy is observed. General examples include: misonidazole with alkylating agents, or tirapazamine with cisplatin. Specific inventive examples for substituted hexitols such as dianhydrogalactitol or diacetyldianhydrogalactitol for treatment of a malignancy such as recurrent malignant glioma or progressive secondary brain tumor include: as a chemosensitizer in combination with topoisomerase inhibitors; use with fraudulent nucleosides; use with fraudulent nucleotides; use with thymidylate synthetase inhibitors; use with signal transduction inhibitors; use with cisplatin or platinum analogs; use with alkylating agents such as BCNU Gliadel wafers, CCNU, bendamustine (Treanda), or Temozoloimide (Temodar); use with anti-tubulin agents; use with antimetabolites; use with berberine; apigenin; amonafide; colchicine and analogs; genistein; etoposide; cytarabine; campothecins; vinca alkaloids; topoisomerase inhibitors; 5-fluorouracil; curcumin; NF-κB inhibitors; rosmarinic acid; mitoguazone; or tetrandrine.

(XIV) Chemopotentiation

Improvements for suboptimal chemotherapeutics including substituted hexitols such as dianhydrogalactitol or diacetyldianhydrogalactitol are made by exploiting them as chemopotentiators where minimal therapeutic activity is observed alone but in combination with other therapeutics unique drug a more than additive or synergistic improvement in efficacy is observed. General examples include: amonafide with cisplatin or 5-FU. Specific inventive examples for substituted hexitols such as dianhydrogalactitol or diacetyldianhydrogalactitol for treatment of a malignancy such as recurrent malignant glioma or progressive secondary brain tumor include: as a chemopotentiator in combination with topoisomerase inhibitors; use with fraudulent nucleosides; use with thymidylate synthetase inhibitors; use with signal transduction inhibitors; use with cisplatin or platinum analogs; use with alkylating agents such as BCNU, BCNU wafers, Gliadel, bendamustine (Treanda); use with anti-tubulin agents; use with antimetabolites; use with berberine; apigenin; amonafide; colchicine and analogs; genistein; etoposide; cytarabine; campothecins; vinca alkaloids; topoisomerase inhibitors; 5-fluorouracil; curcumin; NF-κB inhibitors; rosmarinic acid; mitoguazone; or tetrandrine.

(XV) Post-Treatment Patient Management

Improvements for suboptimal chemotherapeutics including substituted hexitols such as dianhydrogalactitol or diacetyldianhydrogalactitol are made by drugs, treatments and diagnostics to allow for the maximum benefit to patients treated with a compound. General examples include: pain management, nutritional support, anti-emetics, anti-nausea therapies, anti-anemia therapy, anti-inflammatories. Specific inventive examples for substituted hexitols such as dianhydrogalactitol or diacetyldianhydrogalactitol for treatment of a malignancy such as recurrent malignant glioma or progressive secondary brain tumor include: use with therapies associated with pain management; nutritional support; anti-emetics; anti-nausea therapies; anti-anemia therapy; anti-inflammatories: antipyretics; immune stimulants.

(XVI) Alternative Medicine/Therapeutic Support

Improvements for suboptimal chemotherapeutics including substituted hexitols such as dianhydrogalactitol or diacetyldianhydrogalactitol are made by the use of unapproved/non-conventional therapeutics or methods to enhance effectiveness or reduce side effects. General examples include: hypnosis, acupuncture, meditation, herbal medications and extracts, applied kinesiology. Specific inventive examples for substituted hexitols for treatment of a malignancy such as recurrent malignant glioma or progressive secondary brain tumor such as dianhydrogalactitol or diacetyldianhydrogalactitol include: hypnosis; acupuncture; meditation; herbal medications created either synthetically or through extraction including NF-κB inhibitors (such as parthenolide, curcumin, rosmarinic acid); natural anti-inflammatories (including rhein, parthenolide); immunostimulants (such as those found in *Echinacea*); antimicrobials (such as berberine); flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); applied kinesiology.

(XVII) Bulk Drug Product Improvements

Improvements for suboptimal chemotherapeutics including substituted hexitols such as dianhydrogalactitol or diacetyldianhydrogalactitol are made by alterations in the pharmaceutical bulk substance. General examples include: salt formation, homogeneous crystalline structure, pure isomers. Specific inventive examples for substituted hexitols such as dianhydrogalactitol or diacetyldianhydrogalactitol for treatment of a malignancy such as recurrent malignant glioma or progressive secondary brain tumor include: salt formation; homogeneous crystalline structure; pure isomers; increased purity; lower residual solvents and heavy metals.

(XVIII) Diluent Systems

Improvements for suboptimal chemotherapeutics including substituted hexitols such as dianhydrogalactitol or diacetyldianhydrogalactitol are made by alterations in the diluents used to solubilize and deliver/present the compound for administration. General examples include: Cremophor-EL, cyclodextrins for poorly water soluble compounds. Specific inventive examples for substituted hexitols such as dianhydrogalactitol or diacetyldianhydrogalactitol for treatment of a malignancy such as recurrent malignant glioma or progressive secondary brain tumor include: use of emulsions; dimethyl sulfoxide (DMSO); N-methylformamide (NMF); dimethylformamide (DMF); dimethylacetamide (DMA); ethanol; benzyl alcohol; dextrose containing water for injection; Cremophor; cyclodextrins; PEG.

(XIX) Solvent Systems

Improvements for suboptimal chemotherapeutics including substituted hexitols such as dianhydrogalactitol or diacetyldianhydrogalactitol are made by alterations in the solvents used or required to solubilize a compound for administration or for further dilution. General examples include: ethanol, dimethylacetamide (DMA). Specific inventive examples for substituted hexitols such as dianhydrogalactitol or diacetyldianhydrogalactitol for treatment of a malignancy such as recurrent malignant glioma or progressive secondary brain tumor include: the use of emulsions; DMSO; NMF; DMF; DMA; ethanol; benzyl alcohol; dextrose containing water for injection; Cremophor; PEG; salt systems (XX) Excipients Improvements for suboptimal chemotherapeutics including substituted hexitols such as dianhydrogalactitol or diacetyldianhydrogalactitol are made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for substituted hexitols such as dianhydrogalactitol or diacetyldianhydrogalactitol for treatment of a malignancy such as recurrent malignant glioma or progressive secondary brain tumor include: the use of mannitol; the use of albumin; the use of EDTA; the use of sodium bisulfite; the use of benzyl alcohol; the use of carbonate buffers; the use of phosphate buffers; the use of polyethylene glycol (PEG); the use of vitamin A; the use of vitamin D; the use of vitamin E; the use of esterase inhibitors; the use of cytochrome P450 inhibitors; the use of multi-drug resistance (MDR) inhibitors; the use of organic resins; the use of detergents; the use of perillyl alcohol or an analog thereof; or the use of activators of channel-forming receptors.

(XXII) Dosage Forms

Improvements for suboptimal chemotherapeutics including substituted hexitols such as dianhydrogalactitol or diacetyldianhydrogalactitol are made by alterations in the potential dosage forms of the compound dependent on the route of administration, duration of effect, plasma levels required, exposure to side-effect normal tissues and metabolizing enzymes. General examples include: tablets, capsules, topical gels, creams, patches, suppositories. Specific inventive examples for substituted hexitols such as dianhydrogalactitol or diacetyldianhydrogalactitol for treatment of a malignancy such as recurrent malignant glioma or progressive secondary brain tumor include: the use of tablets; capsules; topical gels; topical creams; patches; suppositories; lyophilized dosage fills; the use of immediate-release formulations; the use of slow-release formulations; the use of controlled-release formulations; or the use of liquid in capsules.

(XXII) Dosage Kits and Packaging

Improvements for suboptimal chemotherapeutics including substituted hexitols such as dianhydrogalactitol or diacetyldianhydrogalactitol are made by alterations in the dosage forms, container/closure systems, accuracy of mixing and dosage preparation and presentation. General examples include: amber vials to protect from light, stoppers with specialized coatings. Specific inventive examples for substituted hexitols such as dianhydrogalactitol or diacetyldianhydrogalactitol for treatment of a malignancy such as recurrent malignant glioma or progressive secondary brain tumor include: the use of amber vials to protect from light; stoppers with specialized coatings to improve shelf-life stability.

(XXIII) Drug Delivery Systems

Improvements for suboptimal chemotherapeutics including substituted hexitols such as dianhydrogalactitol or diacetyldianhydrogalactitol are made by the use of delivery systems to improve the potential attributes of a pharmaceutical product such as convenience, duration of effect, reduction of toxicities. General examples include: nanocrystals, bioerodible polymers, liposomes, slow release injectable gels, microspheres. Specific inventive examples for substituted hexitols such as dianhydrogalactitol or diacetyldianhydrogalactitol for treatment of a malignancy such as recurrent malignant glioma or progressive secondary brain tumor include: the use of oral dosage forms; the use of nanocrystals; the use of nanoparticles; the use of cosolvents; the use of slurries; the use of syrups, the use of bioerodible polymers; the use of liposomes; the use of slow release injectable gels; the use of microspheres; or the use of targeting compositions with epidermal growth factor receptor-binding peptides.

(XXIV) Drug Conjugate Forms

Improvements for suboptimal chemotherapeutics including substituted hexitols such as dianhydrogalactitol or diacetyldianhydrogalactitol are made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, or multivalent linkers. Specific inventive examples for substituted hexitols such as dianhydrogalactitol or diacetyldianhydrogalactitol for treatment of a malignancy such as recurrent malignant glioma or progressive secondary brain tumor include: the use of polymer systems such as polyethylene glycols; the use of polylactides; the use of polyglycolides; the use of amino acids; the use of peptides; the use of multivalent linkers; the use of immunoglobulins; the use of cyclodextrin polymers; the use of modified transferrin; the use of hydrophobic or hydrophobic-hydrophilic polymers; the use of conjugates with a phosphonoformic acid partial ester; the use of conjugates with a cell-binding agent incorporating a charged cross-linker; or the use of conjugates with β-glucuronides through a linker.

(XXV) Compound Analogs

Improvements for suboptimal chemotherapeutics including substituted hexitols such as dianhydrogalactitol or diacetyldianhydrogalactitol are made by alterations to the parent structure of a molecule with additional chemical functionalities that may alter efficacy, or reduce toxicity, pharmacological performance, route of administration, or another relevant factor for therapeutic efficacy. General examples include: alteration of side chains to increase or decrease lipophilicity, additional chemical functionalities to alter reactivity, electron affinity, binding capacity, salt forms. Specific inventive examples for substituted hexitols such as dianhydrogalactitol or diacetyldianhydrogalactitol for treatment of a malignancy such as recurrent malignant glioma or progressive secondary brain tumor include: alteration of side chains to increase or decrease lipophilicity; additional chemical functionalities to alter reactivity; electron affinity; binding capacity; salt forms.

(XXVI) Prodrugs

Improvements for suboptimal chemotherapeutics including substituted hexitols such as dianhydrogalactitol or diacetyldianhydrogalactitol are made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for substituted hexitols such as dianhydrogalactitol or diacetyldianhydrogalactitol for treatment of a malignancy such as recurrent malignant glioma or progressive secondary brain tumor include: the use of enzyme sensitive esters; the use of dimers; the use of Schiff bases; the use of pyridoxal complexes; the use of caffeine complexes; the use of nitric oxide-releasing prodrugs; the use of prodrugs with fibroblast activation protein α-cleavable oligopeptides; the use of prodrugs that are products of reaction with an acetylating or carbamylating agent; the use of prodrugs that are hexanoate conjugates; the use of prodrugs that are polymer-agent conjugates; or the use of prodrugs that are subject to redox activation.

(XXVII) Multiple Drug Systems

Improvements for suboptimal chemotherapeutics including substituted hexitols such as dianhydrogalactitol or diacetyldianhydrogalactitol are made by the use of additional compounds, biological agents that when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for substituted hexitols such as dianhydrogalactitol or diacetyldianhydrogalactitol for treatment of a malignancy such as recurrent malignant glioma or progressive secondary brain tumor include: the use of inhibitors of multi-drug resistance; the use of specific drug resistance inhibitors; the use of specific inhibitors of selective enzymes; the use of signal transduction inhibitors; the use of repair inhibition; or the use of topoisomerase inhibitors with non-overlapping side effects.

(XXVIII) Biotherapeutic Enhancement

Improvements for suboptimal chemotherapeutics including substituted hexitols such as dianhydrogalactitol or diacetyldianhydrogalactitol are made by their use in combination as sensitizers/potentiators with biological response modifiers. General examples include: use in combination as sensitizers/poteniators with biological response modifiers, cytokines, lymphokines, therapeutic antibodies, antisense therapies, gene therapies. Specific inventive examples for substituted hexitols such as dianhydrogalactitol or diacetyldianhydrogalactitol for treatment of a malignancy such as recurrent malignant glioma or progressive secondary brain tumor include: use in combination as sensitizers/potentiators with biological response modifiers; cytokines; lymphokines; therapeutic antibodies; antisense therapies such as Avastin, Herceptin, Rituxan, and Erbitux; gene therapies; ribozymes; RNA interference.

(XXIX) Biotherapeutic Resistance Modulation

Improvements for suboptimal chemotherapeutics including substituted hexitols such as dianhydrogalactitol or diacetyldianhydrogalactitol are made by exploiting their selective use to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for substituted hexitols such as dianhydrogalactitol or diacetyldianhydrogalactitol for treatment of a malignancy such as recurrent malignant glioma or progressive secondary brain tumor include: the use against tumors resistant to the effects of biological response modifiers; cytokines; lymphokines; therapeutic antibodies; antisense therapies; therapies such as Avastin, Rituxan, Herceptin, Erbitux; gene therapies; ribozymes; RNA interference.

(XXX) Radiation Therapy Enhancement

Improvements for suboptimal chemotherapeutics including substituted hexitols such as dianhydrogalactitol or diacetyldianhydrogalactitol are made by exploiting their use in combination with ionizing radiation, phototherapies, heat therapies, or radio-frequency generated therapies. General examples include: hypoxic cell sensitizers, radiation sensitizers/protectors, photosensitizers, radiation repair inhibitors. Specific inventive examples for substituted hexitols such as dianhydrogalactitol or diacetyldianhydrogalactitol for treatment of a malignancy such as recurrent malignant glioma or progressive secondary brain tumor include: the use with hypoxic cell sensitizers; radiation sensitizers/protectors; photosensitizers; radiation repair inhibitors; thiol depletion; vaso-targeted agents; use with radioactive seeds, radionuclides, radiolabeled antibodies, brachytherapy.

(XXXI) Novel Mechanisms of Action

Improvements for suboptimal chemotherapeutics including substituted hexitols such as dianhydrogalactitol or diacetyldianhydrogalactitol are made by optimizing their utility by determining the various mechanisms of action, biological targets of a compound for greater understanding and precision to better exploit the utility of the molecule. General examples include: Gleevec for chronic myelocytic leukemia (CML), arsenic trioxide for acute promyelocytic leukemia (APL), retinoic acid for APL. Specific inventive examples for substituted hexitols such as dianhydrogalactitol or diacetyldianhydrogalactitol for treatment of a malignancy such as recurrent malignant glioma or progressive secondary brain tumor include: the use with inhibitors of poly-ADP ribose polymerase; agents that effect vasculature; vasodilation; oncogenic targeted agents; signal transduction inhibitors; EGFR inhibition; Protein Kinase C inhibition; Phospholipase C down-regulation; jun down-regulation; histone genes; VEGF; ornithine decarboxylase; jun D; v-jun; GPCRs; protein kinase A; telomerase, prostate specific genes; protein kinases; histone deacetylase.

(XXXII) Selective Target Cell Population Therapeutics

Improvements for suboptimal chemotherapeutics including substituted hexitols such as dianhydrogalactitol or diacetyldianhydrogalactitol are made by more precise identification and exposure of the compound to those select cell populations where the compound's effect can be maximally exploited. General examples include: tirapazamine and mitomycin C for hypoxic cells, vinca alkaloids for cells entering mitosis. Specific inventive examples for substituted hexitols such as dianhydrogalactitol or diacetyldianhydrogalactitol for treatment of a malignancy such as recurrent malignant glioma or progressive secondary brain tumor include: use against radiation sensitive cells; radiation resistant cells; energy depleted cells; or endothelial cells.

(XXXIII) Use with an Agent Enhancing Activity

Improvements for suboptimal chemotherapeutics including substituted hexitols such as dianhydrogalactitol or diacetyldianhydrogalactitol are made by use of agents to enhance activity of the substituted hexitol. General examples include: use with nicotinamide, caffeine, tetandrine, or berberine. Specific inventive examples for a substituted hexitol for treatment of a malignancy such as recurrent malignant glioma or progressive secondary brain tumor include: use with nicotinamide; use with caffeine; use with tetandrine; or use with berberine.

(XXXIV) Use with an Agent to Counteract Myelosuppression

Improvements for suboptimal chemotherapeutics including substituted hexitols such as dianhydrogalactitol or diacetyldianhydrogalactitol are made by use of agents to counteract myelosuppression. Specific inventive examples for a substituted hexitol derivative such as dianhydrogalactitol for treatment of a malignancy such as recurrent malignant glioma or progressive secondary brain tumor include use of dithiocarbamates to counteract myelosuppression.

(XXXV) Use with an Agent to Increase Ability of Substituted Hexitol to Pass Through the Blood-Brain Barrier Improvements for suboptimal chemotherapeutics including substituted hexitols such as dianhydrogalactitol or diacetyldianhydrogalactitol are made by use of an agent that increases the ability of the substituted hexitol to pass through the blood-brain barrier. Specific examples for a substituted hexitol derivative such as dianhydrogalactitol for treatment of a malignancy such as recurrent malignant glioma or progressive secondary brain tumor include: chimeric peptides; compositions comprising either avidin or an avidin fusion protein bonded to a biotinylated substituted hexitol derivative; neutral liposomes that are pegylated and that incorporate the substituted hexitol derivative and wherein the polyethylene glycol strands are conjugated to at least one transportable peptide or targeting agent; a humanized murine antibody that binds to the human insulin receptor linked to the substituted hexitol derivative through an avidin-biotin linkage; and a fusion protein linked to the hexitol through an avidin-biotin linkage.

Accordingly, another aspect of the present invention is a method to improve the efficacy and/or reduce the side effects of the administration of an alkylating hexitol derivative for treatment of a TKI-resistant malignancy comprising the steps of:

(1) identifying at least one factor or parameter associated with the efficacy and/or occurrence of side effects of the administration of an alkylating hexitol derivative for treatment of a TKI-resistant malignancy; and (2) modifying the factor or parameter to improve the efficacy and/or reduce the side effects of the administration of the alkylating hexitol derivative for treatment of the TKI-resistant malignancy.

Typically, the factor or parameter is selected from the group consisting of:
(1) dose modification;
(2) route of administration;
(3) schedule of administration;
(4) selection of disease stage;
(5) patient selection;
(6) patient/disease phenotype;
(7) patient/disease genotype;
(8) pre/post-treatment preparation
(9) toxicity management;
(10) pharmacokinetic/pharmacodynamic monitoring;
(11) drug combinations;
(12) chemosensitization;
(13) chemopotentiation;
(14) post-treatment patient management;
(15) alternative medicine/therapeutic support;
(16) bulk drug product improvements;
(17) diluent systems;
(18) solvent systems;
(19) excipients;
(20) dosage forms;
(21) dosage kits and packaging;
(22) drug delivery systems;
(23) drug conjugate forms;
(24) compound analogs;
(25) prodrugs;
(26) multiple drug systems;
(27) biotherapeutic enhancement;
(28) biotherapeutic resistance modulation;
(29) radiation therapy enhancement;
(30) novel mechanisms of action;
(31) selective target cell population therapeutics;
(32) use with an agent enhancing its activity;
(33) use with an agent to counteract myelosuppression; and;
(34) use with an agent that increases the ability of the substituted hexitol to pass through the blood-brain barrier.

In some alternatives, the method to improve the efficacy and/or reduce the side effects of the administration of an alkylating hexitol derivative exerts a cytotoxic effect against cancer stem cells.

When the improvement made by is dose modification, the dose modification can be, but is not limited to, at least one dose modification selected from the group consisting of:
(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) use of caffeine to modulate metabolism;
(f) use of isonazid to modulate metabolism;
(g) selected and intermittent boosting of dosage administration;
(h) administration of single and multiple doses escalating from 5 mg/m$^2$/day via bolus;
(i) oral dosages of below 30 mg/m$^2$;
(j) oral dosages of above 130 mg/m$^2$;
(k) oral dosages up to 50 mg/m$^2$ for 3 days and then a nadir/recovery period of 18-21 days, including dosages of 40 mg/m$^2$ or 50 mg/m$^2$);
(l) dosing at a lower level for an extended period (e.g., 21 days);
(m) dosing at a higher level;
(n) dosing with a nadir/recovery period longer than 21 days;
(o) the use of an alkylating hexitol derivative as a single cytotoxic agent;
(p) immediate release dosing;
(q) slow release dosing;
(r) controlled release dosing;
(s) dosage reduction to control or limit reduction of function of the immune system;
(t) dosage reduction to control or limit myelosuppression;
(u) a dose of 1.5 mg/m$^2$ (cumulative dose 9 mg/m$^2$ in a 33-day cycle);
(v) a dose of 3.0 mg/m$^2$ (cumulative dose 18 mg/m$^2$ in a 33-day cycle);
(w) a dose of 5.0 mg/m$^2$ (cumulative dose 30 mg/m$^2$ in a 33-day cycle);
(x) a dose of 10 mg/m$^2$ (cumulative dose 60 mg/m$^2$ in a 33-day cycle);
(y) a dose of 15 mg/m$^2$ (cumulative dose 90 mg/m$^2$ in a 33-day cycle);
(z) a dose of 20 mg/m$^2$ (cumulative dose 120 mg/m$^2$ in a 33-day cycle);
(aa) a dose of 25 mg/m$^2$ (cumulative dose 150 mg/m$^2$ in a 33-day cycle);
(ab) a dose of 30 mg/m$^2$ (cumulative dose 180 mg/m$^2$ in a 33-day cycle);
(ac) a dose of 40 mg/m$^2$ (cumulative dose 240 mg/m$^2$ in a 33-day cycle);
(ad) a dose of 50 mg/m$^2$ (cumulative dose 300 mg/m$^2$ in a 33-day period);
(ae) a dose beginning at 1.5 mg/m$^2$ and increasing to 3.0 mg/m$^2$;
(af) a dose beginning at 1.5 mg/m$^2$, increasing to 3.0 mg/m$^2$, then increasing to 5.0 mg/m$^2$;
(ag) a dose beginning at 1.5 mg/m$^2$, increasing to 3.0 mg/m$^2$, then increasing to 5.0 mg/m$^2$, then increasing to 10 mg/m$^2$;
(ah) a dose beginning at 1.5 mg/m$^2$, increasing to 3.0 mg/m$^2$, then increasing to 5.0 mg/m$^2$, then increasing to 10 mg/m$^2$, then increasing to 20 mg/m$^2$;
(ai) a dose beginning at 1.5 mg/m$^2$, increasing to 3.0 mg/m$^2$, then increasing to 5.0 mg/m$^2$, then increasing to 10 mg/m$^2$, then increasing to 20 mg/m$^2$, then increasing to 25 mg/m$^2$;
(aj) a dose beginning at 1.5 mg/m$^2$, increasing to 3.0 mg/m$^2$, then increasing to 5.0 mg/m$^2$, then increasing to 10 mg/m$^2$, then increasing to 20 mg/m$^2$, then increasing to 25 mg/m$^2$, then increasing to 30 mg/m$^2$;
(ak) a dose beginning at 1.5 mg/m$^2$, increasing to 3.0 mg/m$^2$, then increasing to 5.0 mg/m$^2$, then increasing to 10 mg/m$^2$, then increasing to 20 mg/m$^2$, then increasing to 25 mg/m$^2$, then increasing to 30 mg/m$^2$, then increasing to 40 mg/m$^2$; and
(al) a dose beginning at 1.5 mg/m$^2$, increasing to 3.0 mg/m$^2$, then increasing to 5.0 mg/m$^2$, then increasing to 10 mg/m$^2$, then increasing to 20 mg/m$^2$, then increasing to 25 mg/m$^2$, then increasing to 30 mg/m$^2$, then increasing to 40 mg/m$^2$; then increasing to 50 mg/m$^2$.

Other sequences of dosages can be employed, starting with one of the dosage steps described above and increasing through other dosage steps; one or more steps can be skipped depending on clinical response.

The use of immediate release dosing is described in U.S. Pat. No. 8,299,052 by Flanner et al., incorporated herein by this reference. The use of slow release dosing is described in U.S. Pat. No. 8,303,986 to Vergnault et al., incorporated herein by this reference. The use of controlled release dosing is described in U.S. Pat. No. 8,304,577 to Dzierba et al., incorporated herein by this reference. Controlled release dosing can be achieved by the use of biodegradable polymers such as, but not limited to, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Due to prior chemotherapy and radiation therapy, patients with secondary brain tumors are likely more prone to myelosuppression and may have a different MTD (maximum tolerated dose) than patients with GBM. This can be determined by assessing function of the immune system and monitoring possible myelosuppression. Dosages can then be adjusted if required to maintain function of the immune system or prevent myelosuppression. Methods for clinical assessment of immune function are well known in the art and are described in P. Hutchinson et al., "Laboratory Assessment of Immune Function in Renal Transplant Patients," *Nephrol. Dial. Transplant.* 18: 983-989 (2003), incorporated herein by this reference, and include assessment of lymphocyte subsets, measurement of mitogen-induced T-cell responses, neutrophil phagocytic capacity, and reactive oxygen species (ROS) generation. Methods for clinical assessment of myelosuppression are well known in the art and are described in R. E. Parchment et al., "Predicting Hematological Toxicity (Myelosuppression) of Cytotoxic Drug Therapy from in Vitro Tests," *Ann. Oncol.* 9: 357-364 (1998) and in J. W. Winter et al., "Assessment of Thiopurine Methyltransferase Activity Is Superior to Genotype in Predicting Myelosuppression Following Azathioprine Therapy in Patients with Inflammatory Bowel Disease," *Aliment. Pharmacol. Ther.* 25: 1069-1077 (2007), both incorporated herein by this reference, and include clonogenic assays for detection of CFU-GM (granulocyte-macrophage colony-forming cells), genotypic analysis of genes for thiopurine methyltransferase, and assay of thiopurine methyltransferase activity.

When the improvement is made by route of administration, the route of administration can be, but is not limited to, at least one route of administration selected from the group consisting of:
  (a) topical administration;
  (b) oral administration;
  (c) slow release oral delivery;
  (d) intrathecal administration;
  (e) intraarterial administration;
  (f) continuous infusion;
  (g) intermittent infusion;
  (h) intravenous administration, such as intravenous administration for 30 minutes;
  (i) administration through a longer infusion;
  (j) administration through IV push; and
  (k) intraperitoneal administration.

When the improvement comprises route of administration, typically the method comprises the administration of dianhydrogalactitol by dosing once daily for three consecutive days every 21 days. Dosages are typically as described above. Other schedules of administration can be employed as described in further detail below.

When the improvement is made by schedule of administration, the schedule of administration can be, but is not limited to, at least one schedule of administration selected from the group consisting of:
  (a) daily administration;
  (b) weekly administration;
  (c) weekly administration for three weeks;
  (d) biweekly administration;
  (e) biweekly administration for three weeks with a 1-2 week rest period;
  (f) intermittent boost dose administration;
  (g) daily administration for one week for multiple weeks;
  (h) dosing at up to 50 mg/m$^2$ for 3 days and then a nadir/recovery period of 18 to 21 days (dosages can be at 25 mg/m$^2$/day, 40 mg/m$^2$/day, or 50 mg/m$^2$/day);
  (i) dosing at a lower level for extended periods (e.g., 21 days);
  (j) dosing at a higher level;
  (k) dosing with a nadir/recovery period longer than 21 days; and
  (l) dosing once daily for three consecutive days every 21 days.

When the schedule of administration is dosing once daily for three consecutive days every 21 days, the dosage can be a constant dose or can be increased with each successive three-day period of dosing according to clinical response and toleration of the increasing dosages as described above.

In the improvements described below, typically the methods comprise the administration of dianhydrogalactitol by dosing once daily for three consecutive days every 21 days. When the methods comprise the administration of dianhydrogalactitol by dosing once daily for three consecutive days every 21 days, dosages are typically as described above. However, other dosage schedules and dosages can be employed as described above.

When the improvement is made by selection of disease stage, the selection of disease stage can be, but is not limited to, at least one selection of disease stage selected from the group consisting of:
  (a) use for the treatment of recurrent malignant glioma; and
  (b) use for the treatment of progressive secondary brain tumor such as that caused by metastases of breast adenocarcinoma, small-cell lung carcinoma, or melanoma.

When the improvement is made by patient selection, the patient selection can be, but is not limited to, a patient selection carried out by a criterion selected from the group consisting of:
  (a) selecting patients with a disease condition characterized by a high level of a metabolic enzyme selected from the group consisting of histone deacetylase and ornithine decarboxylase;
  (b) selecting patients with a low or high susceptibility to a condition selected from the group consisting of thrombocytopenia and neutropenia;
  (c) selecting patients intolerant of GI toxicities; and
  (d) selecting patients characterized by over- or under-expression of a gene selected from the group consisting of c-Jun, a GPCR, a signal transduction protein, VEGF, a prostate-specific gene, and a protein kinase.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, $β_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

When the improvement is made by analysis of patient or disease phenotype, the analysis of patient or disease phenotype can be, but is not limited to, a method of analysis of patient or disease phenotype carried out by a method selected from the group consisting of:
(a) use of a diagnostic tool, a diagnostic technique, a diagnostic kit, or a diagnostic assay to confirm a patient's particular phenotype;
(b) use of a method for measurement of a marker selected from the group consisting of histone deacetylase, ornithine decarboxylase, VEGF, a protein that is a gene product of a prostate specific gene, a protein that is a gene product of jun, a protein kinase, desmoglein-3, and a caspase-derived neo-epitope;
(c) surrogate compound dosing; and
(d) low dose pre-testing for enzymatic status.

The measurement of the protein desmoglein-3 as a marker of metastasis of a tumor to lymph nodes and the selection of appropriate therapy based on the amount of desmoglein-3 in a sample from a subject is described in United States Patent Application Publication No. 2012/0087892 by Gutkind et al., incorporated herein by this reference.

The measurement of caspase-derived neo-epitopes as an indicator of apoptosis, including apoptosis induced by antineoplastic agents, is described in United States Patent Application Publication No. 2012/0028266 by Wells et al., incorporated herein by this reference.

When the improvement is made by analysis of patient or disease genotype, the analysis of patient or disease genotype can be, but is not limited to, a method of analysis of patient or disease genotype carried out by a method selected from the group consisting of:
(a) use of a diagnostic tool, a diagnostic technique, a diagnostic kit, or a diagnostic assay to confirm a patient's particular genotype;
(b) use of a gene chip;
(c) use of gene expression analysis;
(d) use of single nucleotide polymorphism (SNP) analysis; and
(e) measurement of the level of a metabolite or a metabolic enzyme.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference.

When the improvement is made by pre/post-treatment preparation, the pre/post-treatment preparation can be, but is not limited to, a method of pre/post treatment preparation selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) infection control; and
(j) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:
  (a) the use of colchicine or an analog thereof;
  (b) the use of a uricosuric;
  (c) the use of uricase;
  (d) the non-oral use of nicotinamide;
  (e) the use of a sustained-release form of nicotinamide;
  (f) the use of an inhibitor of poly-ADP ribose polymerase;
  (g) the use of caffeine;
  (h) the use of leucovorin rescue;
  (i) the use of sustained-release allopurinol;
  (j) the non-oral use of allopurinol;
  (k) the use of bone marrow transplants;
  (l) the use of a blood cell stimulant;
  (m) the use of blood or platelet infusions;
  (n) the administration of an agent selected from the group consisting of filgrastim (Neupogen®), G-CSF, and GM-CSF;
  (o) the application of a pain management technique;
  (p) the administration of an anti-inflammatory agent;
  (q) the administration of fluids;
  (r) the administration of a corticosteroid;
  (s) the administration of an insulin control medication;
  (t) the administration of an antipyretic;
  (u) the administration of an anti-nausea treatment;
  (v) the administration of an anti-diarrheal treatment;
  (w) the administration of N-acetylcysteine;
  (x) the administration of an antihistamine; and
  (y) the administration of agents for reduction of gastric toxicity.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Nonsteroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

Agents for reduction of gastric toxicity include, but are not limited to, ferruginol (C. Areche et al., "Gastroprotective Activity of Ferruginol in Mice and Rats: Effects on Gastric Secretion, Endogenous Prostaglandins and Non-Protein Sulfhydryls," *J. Pharm. Pharmacol.* 60: 245-251 (2008)), incorporated herein by this reference.

When the improvement is made by pharmacokinetic/pharmacodynamic monitoring, the pharmacokinetic/pharmacodynamic monitoring can be, but is not limited to a method selected from the group consisting of:
  (a) multiple determinations of blood plasma levels; and
  (b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

When the improvement is made by drug combination, the drug combination can be, but is not limited to, a drug combination selected from the group consisting of:
(a) use with fraudulent nucleosides;
(b) use with fraudulent nucleotides;
(c) use with thymidylate synthetase inhibitors;
(d) use with signal transduction inhibitors;
(e) use with cisplatin or platinum analogs;
(f) use with alkylating agents;
(g) use with anti-tubulin agents;
(h) use with antimetabolites;
(i) use with berberine;
(j) use with apigenin;
(k) use with colchicine or an analog thereof;
(l) use with genistein;
(m) use with etoposide;
(n) use with cytarabine;
(o) use with camptothecins;
(p) use with vinca alkaloids;
(q) use with topoisomerase inhibitors;
(r) use with 5-fluorouracil;
(s) use with curcumin;
(t) use with NF-κB inhibitors;
(u) use with rosmarinic acid;
(v) use with mitoguazone;
(w) use with meisoindigo;
(x) use with imatinib;
(y) use with dasatinib;
(z) use with nilotinib;
(aa) use with epigenetic modulators;
(ab) use with transcription factor inhibitors;
(ac) use with taxol;
(ad) use with homoharringtonine;
(ae) use with pyridoxal;
(af) use with spirogermanium;
(ag) use with caffeine;
(ah) use with nicotinamide;
(ai) use with methylglyoxalbisguanylhydrazone;
(aj) use with Rho kinase inhibitors;
(ak) use with 1,2,4-benzotriazine oxides;
(al) use with an alkylglycerol;
(am) use with an inhibitor of a Mer, Ax1, or Tyro-3 receptor kinase;
(an) use with an inhibitor of ATR kinase;
(ao) use with a modulator of Fms kinase, Kit kinase, MAP4K4 kinase, TrkA kinase, or TrkB kinase;
(ap) use with endoxifen;
(aq) use with a mTOR inhibitor;
(ar) use with an inhibitor of Mnk1a kinase, Mkn1b kinase, Mnk2a kinase, or Mnk2b kinase;
(as) use with a modulator of pyruvate kinase M2;
(at) use with a modulator of phosphoinositide 3-kinases;
(au) use with a cysteine protease inhibitor;
(av) use with phenformin;
(aw) use with Sindbis virus-based vectors;
(ax) use with peptidomimetics that act as mimetics of Smac and inhibit IAPs to promote apoptosis;
(ay) use with a Raf kinase inhibitor;
(az) use with a nuclear transport modulator;
(ba) use with an acid ceramidase inhibitor and a choline kinase inhibitor;
(bb) use with tyrosine kinase inhibitors;
(bc) use with anti-CS1 antibodies;
(bd) use with inhibitors of protein kinase CK2;
(be) use with anti-guanylyl cyclase C (GCC) antibodies;
(bf) use with histone deacetylase inhibitors;
(bg) use with cannabinoids;
(bh) use with glucagon-like peptide-1 (GLP-1) receptor agonists;
(bi) use with inhibitors of Bcl-2 or Bcl-xL;
(bj) use with Stat3 pathway inhibitors;
(bk) use with inhibitors of polo-like kinase 1 (Plk1);
(bl) use with GBPAR1 activators;
(bm) use with modulators of serine-threonine protein kinase and poly(ADP-ribose) polymerase (PARP) activity;
(bn) use with taxanes;
(bo) use with inhibitors of dihydrofolate reductase;
(bp) use with inhibitors of aromatase;
(bq) use with benzimidazole-based anti-neoplastic agents;
(br) use with an 06-methylguanine-DNA-methyltransferase (MGMT) inhibitor;
(bs) use with CCR9 inhibitors;
(bt) use with acid sphingomyelinase inhibitors;
(bu) use with peptidomimetic macrocycles;
(bv) use with cholanic acid amides;
(bw) use with substituted oxazaphorines;
(bx) use with anti-TWEAK receptor antibodies;
(by) use with an ErbB3 binding protein;
(bz) use with a glutathione S-transferase-activated anti-neoplastic compound;
(ca) use with substituted phosphorodiamidates;
(cb) use with inhibitors of MEKK protein kinase;
(cd) use with COX-2 inhibitors;
(ce) use with cimetidine and a cysteine derivative;
(cf) use with anti-IL-6 receptor antibody;
(cg) use with an antioxidant;
(ch) use with an isoxazole inhibitor of tubulin polymerization;
(ci) use with PARP inhibitors;
(cj) use with Aurora protein kinase inhibitors;
(ck) use with peptides binding to prostate-specific membrane antigen;
(cl) use with CD19 binding agents;
(cm) use with benzodiazepines;
(cn) use with Toll-like receptor (TLR) agonists;
(co) use with bridged bicyclic sulfamides;
(cp) use with inhibitors of epidermal growth factor receptor kinase;
(cq) use with a ribonuclease of the T2 family having actin-binding activity;
(cr) use with myrsinoic acid A or an analog thereof;
(cs) use with inhibitors of a cyclin-dependent kinase;
(ct) use with inhibitors of the interaction between p53 and MDM2;
(cu) use with inhibitors of the receptor tyrosine kinase MET;
(cv) use with largazole or largazole analogs;
(cw) use with inhibitors of AKT protein kinase;
(cx) use with 2'-fluoro-5-methyl-β-L-arabinofuranosyluridine or L-deoxythymidine;
(cy) use with HSP90 modulators;
(cz) use with inhibitors of JAK kinases;
(da) use with inhibitors of PDK1 protein kinase;
(db) use with PDE4 inhibitors;
(de) use with inhibitors of proto-oncogene c-Met tyrosine kinase;
(df) use with inhibitors of indoleamine 2,3-dioxygenase;
(dg) use with agents that inhibit expression of ATDC (TRIM29);
(dh) use with proteomimetic inhibitors of the interaction of nuclear receptor with coactivator peptides;

(di) use with antagonists of XIAP family proteins;
(dj) use with tumor-targeted superantigens;
(dk) use with inhibitors of Pim kinases;
(dl) use with inhibitors of CHK1 or CHK2 kinases;
(dm) use with inhibitors of angiopoietin-like 4 protein;
(dn) use with Smo antagonists;
(do) use with nicotinic acetylcholine receptor antagonists;
(dp) use with farnesyl protein transferase inhibitors;
(dq) use with adenosine A3 receptor antagonists;
(dr) use with a cancer vaccine;
(ds) use with a JAK2 inhibitor; and
(dt) use with a Src inhibitor.

Topoisomerase inhibitors include, but are not limited to, irinotecan, topotecan, camptothecin, lamellarin D, amsacrine, etoposide, etoposide phosphate, teniposide, doxorubicin, and 4-[2-(3,5-dioxo-1-piperazinyl)-1-methylpropyl]piperazine-2,6-dione (ICRF-193).

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Colchicine is a tricyclic alkaloid that exerts its activity by binding to the protein tubulin. Analogs of colchicine include, but are not limited to, colchiceinamide, N-desacetylthiocolchicine, demecolcine, N-acetyliodocolchinol, trimethylcolchicinic acid (TMCA) methyl ether, N-acetylcolchinol, TMCA ethyl ether, isocolchicine, isocolchiceinamide, iso-TMCA methyl ether, colchiceine, TMCA, N-benzoyl TMCA, colchicosamide, colchicoside, colchinol and colchinoic acid (M. H. Zweig & C. F. Chignell, "Interaction of Some Colchicine Analogs, Vinblastine and Podophyllotoxin with Rat Brain Microtubule Protein," *Biochem. Pharmacol.* 22: 2141-2150 (1973) and B. Yang et al., "Syntheses and Biological Evaluation of Ring C-Modified Colchicine Analogs," *Bioorg. Med. Chem. Lett.* 20: 3831-3833 (2010)), both of which are incorporated herein by this reference.

Genistein is an isoflavone with the systemic name 5,7-dihydroxy-3-(4-hydroxyphenyl)chromen-4-one. Genistein has a number of biological activities, including activation of PPARs, inhibition of several tyrosine kinases, inhibition of topoisomerase, antioxidative activity, activation of Nrf2 antioxidative response, activation of estrogen receptor beta, and inhibition of the mammalian hexose transporter GLUT2.

Etoposide is an anticancer agent that acts primarily as a topoisomerase II inhibitor. Etoposide forms a ternary complex with DNA and the topoisomerase II enzyme, prevents re-ligation of the DNA strands and thus induces DNA strand breakage and promotes apoptosis of the cancer cells.

Cytarabine is a nucleoside analog replacing the ribose with arabinose. It can be incorporated into DNA and also inhibits both DNA and RNA polymerases and nucleotide reductase. It is particularly useful in the treatment of acute myeloid leukemia and acute lymphocytic leukemia, but can be used for other malignancies and in various drug combinations.

Camptothecins include camptothecin, homocamptothecin, topotecan, irinotecan, DB 67, BNP 1350, exatecan, lurtotecan, ST 1481, and CKD 602. These compounds act as topoisomerase I inhibitors and block DNA synthesis in cancer cells.

Vinca alkaloids include vinblastine, vincristine, vindesine, and vinorelbine.

Topoisomerase inhibitors include topoisomerase I inhibitors and topoisomerase II inhibitors. Topoisomerase I inhibitors include the camptothecins and lamellarin D. Topoisomerase II inhibitors include, in addition to amonafide and derivatives and analogs thereof, etoposide, teniposide, doxorubicin, daunorubicin, mitoxantrone, amsacrine, ellipticines, and aurintricarboxylic acid. A number of plant-derived naturally-occurring phenolic compounds, such as genistein, quercetin, and resveratrol, exhibit inhibitory activity toward both topoisomerase I and topoisomerase II.

The compound 5-fluorouracil is a base analog that acts as a thymidylate synthase inhibitor and thereby inhibits DNA synthesis. When deprived of a sufficient supply of thymidine, rapidly dividing cancer cells die by a process known as thymineless death.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Meisoindigo is active via several, possibly novel mechanisms of action. It has cell cycle specific effects, including arrest in G(O)/G1 for AML cell lines and G2/M arrest for HT-29 colorectal cell lines. It also stimulates apoptosis through a number of mechanisms, including the upregulation of p21 and p27 and the downregulation of Bcl-2 in primary AML cells, as well as upregulation of Bak and Bax in AML cells (DKO insensitive to chemotherapy), and a novel caspase-dependent pathway in K562 cells. Meisoindigo also has effects on mitochondria, but with no change in Bcl-2, Bax, and Bid protein expression. Meisoindigo also stimulates the cleavage of pro-caspase 3, 8, 9 and PARP in HL-60 myeloid cells. Meisoindigo also is directed to multiple cellular targets, which are possibly synergistic and complementary. For example, it promotes differentiation of human myeloblastic leukemic cells, accompanied by downregulation of c-myb gene expression. It also promotes inhibition of DNA and RNA synthesis in W256 cells, microtubule assembly, glycogen synthase kinase-3β (GSK-3β) (at 5-50 nM), CDK1/cyclin B, and CDK5/p25 (tau microtubule protein phosphorylation). Additionally, meisoindigo decreases β-catenin and c-myc (HL-60 cells, but not in K562), affects the Wnt pathway through inhibiting GSK-3β and downregulating β-catenin and c-myc protein expression. Meisoindigo also promotes upregulation of CD1 b, promoting myeloid differentiation, and upregulation of Ahi-1 in Jurkat cells (inducing phosphorylation of c-Myb). Furthermore, meisoindigo exhibits antiangiogenic effects, including decreased VEGF protection, VCAM-1, tubule formulation in HUVEC, and ECV304 apoptosis.

Imatinib is an inhibitor of the receptor tyrosine kinase enzyme ABL and is used to treat chronic myelogenous leukemia, gastrointestinal stromal tumors, and other hyperproliferative disorders.

Dasatinib is an inhibitor of BCR/ABL and Src family tyrosine kinases and is used to treat chronic myelogenous leukemia and acute lymphoblastic leukemia.

Nilotinib is another tyrosine kinase inhibitor approved for the treatment of chronic myelogenous leukemia; it inhibits the kinases BCR/ABL, KIT, LCK, EPHA3, and a number of other kinases. The use of nilotinib is described in United States Patent Application Publication No. 2011/0028422 by Aloyz et al., incorporated herein by this reference.

Epigenetic modulators include polyamine-based epigenetic modulators, such as the polyamine-based epigenetic modulators described in S. K. Sharma et al., "Polyamine-Based Small Molecule Epigenetic Modulators," *Med. Chem. Commun.* 3: 14-21 (2012), and L. G. Wang & J. W. Chiao, "Prostate Cancer Chemopreventive Activity of Phenethyl Isothiocyanate Through Epigenetic Regulation (Review), *Int. J. Oncol.* 37: 533-539 (2010), both incorporated herein by this reference.

Transcription factor inhibitors include 1-(4-hexaphenyl)-2-propane-1-one, 3-fluoro-4-[[2-hydroxy-2-(5,5,8,8-tetramethyl-5,6,7,8,-tetrahydro-2-naphthalenyl)acetyl]amino]-benzoic acid (BMS 961), 4-[5-[8-(1-methylethyl)-4-phenyl-2-quinolinyl]-1H-pyrrolo-2-benzoic acid (ER-50891), 7-ethenyl-2-(3-fluoro-4-hydroxyphenyl)-5-benzoxazolol (ERB 041), and other compounds. Trascription factor inhibitors are described in T. Berg, "Inhibition of Transcription Factors with Small Organic Molecules," *Curr. Opin. Chem. Biol.* 12: 464-471 (2008), incorporated herein by this reference.

Tetrandrine has the chemical structure 6,6',7,12-tetramethoxy-2,2'-dimethyl-1β-berbaman and is a calcium channel blocker that has anti-inflammatory, immunologic, and anti-allergenic effects, as well as an anti-arrhythmic effect similar to that of quinidine. It has been isolated from *Stephania tetranda* and other Asian herbs.

VEGF inhibitors include bevacizumab (Avastin), which is a monoclonal antibody against VEGF, itraconazole, and suramin, as well as batimastat and marimastat, which are matrix metalloproteinase inhibitors, and cannabinoids and derivatives thereof.

Cancer vaccines are being developed. Typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," *Crit. Rev. Oncol. Hematol.* 67: 93-102 (2008), incorporated herein by this reference.

The use of methylglyoxalbisguanylhydrazone in cancer therapy has been described in D. D. Von Hoff, "MGBG: Teaching an Old Drug New Tricks," *Ann. Oncol.* 5: 487-493 (1994), incorporated herein by this reference.

The use of Rho kinase inhibitors, such as (R)-(+)-N-(4-pyridyl)-4-(1-aminoethyl)benzamide, ethacrynic acid, 4-[2 (2,3,4,5,6-pentafluorophenyl)acryloyl]cinnamic acid, (+)-trans-4-(1-aminoethyl)-1-(4-pyridylcarbamoyl) cyclohexane, (+)-10 trans-N-(1H-pyrrolo[2,3-b]pyridin-4-yl)-4-(1-aminoethyl)cyclohexanecarboxamide, and (R)-(+)-N-(1H-pyrrolo[2,3-b]pyridin-4-yl)-4-(1-aminoethyl) benzamide, as described in U.S. Pat. No. 6,930,115 to Fujii et al., incorporated herein by this reference.

The use of 1,2,4-benzotriazine oxides, such as 3-hydroxy-1,2,4-benzotriazine 1,4-dioxide, 3-amino-7-trifluoromethyl-1,2,4-benzotriazine 1-oxide, 3-amino-7-carbamyl-1,2,4-benzotriazine 1-oxide, 7-acetyl-3-amino-1,2,4-benzotriazine 1-oxide oxime, 3-amino-6(7)decyl-1,2,4-benzotriazine 1,4-dioxide, 1,2,4-benzotriazine dioxide, 7-chloro-3-hydroxy-1,2,4-benzotriazine 1,4-dioxide, 7-nitro-3-amino-1,2,4-benzotriazine 1,4-dioxide, 3-(3-N, N-diethyl-aminopropylamino)-1,2,4-benzotriazine 1,4-dioxide, 7-nitro-3-(2-N,N-diethylaminoethylamino)-1,2,4-benzotriazine 1,4-dioxide, 7-allyloxy-1,2,4-benzotriazine 1,4-dioxide, 7-(3-N-ethylacetamido-2-acetoxypropoxy) 1,2,4-benzotriazine 1,4-dioxide, 7-nitro-1,2,4-benzotriazine 1,4-dioxide. 3-propyl-1,2,4-benzotriazine 1,4-dioxide, and 3-(1-hydroxyethyl)-1,2,4-benzotriazine 1,4-dioxide, as described in U.S. Pat. No. 6,277,835 by Brown, incorporated herein by this reference.

The use of alkylglycerols is described in U.S. Pat. No. 6,121,245 to Firshein, incorporated herein by this reference.

The use of inhibitors of Mer, Ax1, or Tyro-3 receptor tyrosine kinase is described in United States Patent Application Publication No. 2012/0230991 by Graham et al., incorporated herein by this reference. These inhibitors can be antibodies, including monoclonal antibodies, or fusion proteins.

The use of inhibitors of ATR kinase is described in United States Patent Application Publication No. 2012/0177748 by Charrier et al., incorporated by these reference. These inhibitors of ATR kinase are substituted pyridine compounds such as 2-amino-N-phenyl-5-(3-pyridyl)pyridine-3-carboxamide, 5-(4-(methylsulfonyl)phenyl-3-(5-phenyl-1,3,4-oxadiazol-2-yl)pyridine-2-amine, and 5-(1-ethylsulfonyl-3,6-dihydro-2H-pyridin-4-yl)-3-(5-phenyl-1,3,4-oxadiazol-2-yl)pyridine-2-amine.

The use of compounds that modulate the activity of one or more of Fms kinase, Kit kinase, MAP4K4 kinase, TrkA kinase, or TrkB kinase is described in United States Patent Application Publication No. 2012/0165329 by Ibrahim et al., incorporated herein by this reference. These compounds include (6-methoxy-pyridin-3-ylmethyl)[5-(7H-pyrrolo[2,3-d]pyrimidin-5-ylmethyl)-pyrimidin-2-yl]-amine, (5-fluoro-2-methoxy-pyridin-3-ylmethyl)-[5-(7H-pyrrolo[2,3-d]pyrimidin-5-ylmethyl)-pyrimidin-2-y]-amine, and (5-fluoro-6-methoxy-pyridin-3-ylmethyl)-[5-(7H-pyrrolo[2,3-d]pyrimidin-5-ylmethyl)-pyrimidin-2-yl]-amine. Compounds that inhibit Trk kinases, particularly TrkA, are described in United States Patent Application Publication No. 2011/0301133 by Wu et al., incorporated herein by this reference.

The use of endoxifen is described in United States Patent Application Publication No. 2012/0164075 by Ahmad et al., incorporated herein by this reference.

The use of a mTOR inhibitor is described in United States Patent Application Publication No. 2012/0129881 by Burke et al., incorporated herein by this reference. Suitable mTOR inhibitors include, but are not limited to, 40-O-(2-hydroxyethyl)rapamycin. These mTOR inhibitors can be used together with Raf kinase inhibitors, as described in United States Patent Application Publication No. 2011/0301184 by Lane, incorporated herein by this reference. Raf kinase inhibitors are also described in United States Patent Application Publication No. 2010/0286178 by Ibrahim et al., incorporated herein by this reference; these compounds include, but are not limited to, propane-1-sulfonic acid {2,4-difluoro-3-[5-(2-methoxy-pyrimidin-5-yl)-1H-pyrrolo[2,3-b]pyridine-3-carbonyl]-phenyl}-amide, propane-1-sulfonic acid [3-(5-cyano-1H-pyrrolo[2,3-b]pyridine-3-carbonyl)-2,4-difluoro-phenyl]-amide, propane-1-sulfonic acid [3-(5-cyano-1H-pyrrolo[2,3-b]pyridine-3-carbonyl)-2-fluoro-phenyl]-amide, N-[3-(5-cyano-1H-pyrrolo[2,3-b]pyridine-3-carbonyl)-2,4-difluoro-phenyl]-2,5-difluoro-benzenesulfonamide, N-[3-(5-cyano-1H-pyrrolo[2,3-b]pyridine-3-carbonyl)-2,4-difluoro-phenyl]-3-fluoro-benzenesulfonamide, pyrrolidine-1-sulfonic acid [3-(5-cyano-1H-pyrrolo[2,3-b]pyridine-3-carbonyl)-2,4-difluoro-phenyl]-amide, and N,N-dimethylamino-sulfonic acid [3-(5-cyano-1H-pyrrolo[2,3-b]pyridine-3-carbonyl)-2,4-difluoro-phenyl]-amide. These mTOR inhibitors can also be used together with compounds that elevate pAkt levels in malignant cells, as described in United States Patent Application Publication No. 2009/0274698 by Bhagwat et al., incorporated herein by this reference. A number of compounds that elevate pAkt levels are described, including chemotherapeutic agents, analogs of rapamycin, and other agents. The use of mTOR inhibitors is also described in U.S. Pat. No. 8,268,819 to Jin et al., incorporated by this reference; these mTOR inhibitors are hexahydrooxazinopterine compounds.

The use of an inhibitor of Mnk1a kinase, Mnk1b kinase, Mnk2a kinase, or Mnk2b kinase is described in United States Patent Application Publication No. 2012/0128686 by Austen et al., incorporated herein by this reference. These compounds include thienopyrimidines. Additional thienopyrimidine inhibitors of one or more of these kinases are described in United States Patent Application Publication No. 2011/0212103 by Heckel et al. and in United States Patent Application Publication No. 2011/0212102 by Lehmann-Lintz et al., both incorporated herein by this reference.

The use of a modulator of pyruvate kinase M2 is described in United States Patent Application Publication 2012/0122885 by Salituro et al., incorporated herein by this reference. Suitable modulators of pyruvate kinase M2 include, but are not limited to, 1-(3-chloro-5-(trifluoromethyl)pyridin-2-yl)-N-(3,5-dimethylphenyl)-1H-imidazole-5-sulfonamide; 1-(3-chloro-5-(trifluoromethyl)pyridin-2-yl)-N-(5-methoxyphenyl)-1H-imidazole-5-sulfonamide; and N-(4-methoxyphenyl)-1-(5-(trifluoromethyl)pyridine-2-yl)-H-imidazole-5-sulfonamide.

The use of a modulator of a phosphoinositide 3-kinase is described in United States Patent Application Publication No. 2012/0122838 by Ren et al., incorporated herein by this reference. Inhibitors of phosphoinositide 3-kinase are also described in United States Patent Application Publication No. 2010/0209420 by Lamb et al., incorporated herein by this reference, and in United States Patent Application Publication No. 2009/0209340 by Buhr et al., incorporated herein by this reference; these inhibitors include pyridopyrimidones. Inhibitors of phosphoinositide 3-kinase are also described in U.S. Pat. No. 8,242,104 to Blaquiere et al., incorporated herein by this reference; these inhibitors include benzoxazepines. Inhibitors of phosphoinositide 3-kinase are also described in U.S. Pat. No. 8,193,182 to Ren et al.; these inhibitors include isoquinolin-1(2H)-ones. Inhibitors of phosphoinositide 3-kinase are also described in U.S. Pat. No. 7,928,428 to Do et al., incorporated herein by this reference; these inhibitors include benzopyrans and benzoxepines.

The use of a cysteine protease inhibitor is described in United States Patent Application Publication No. 2012/0114765 by Cao et al., incorporated herein by this reference. Suitable cysteine protease inhibitors include, but are not limited to, 1-[5-(2,4-dichlorophenylsulfanyl)-4-nitro-2-thienyl]ethanone, 1-[5-(2,4-difluorophenylsulfanyl)-4-nitro-2-thienyl]ethanone, and 1-{4-nitro-5-[2-(trifluoromethyl)phenylsulfanyl]-2-thienyl}ethanone.

The use of phenformin is described in United States Patent Application Publication No. 2012/0114676 by Thompson et al., incorporated herein by this reference.

The use of Sindbis-based virus vectors is described in United States Patent Application Publication No. 2011/0318430 by Meruelo et al., incorporated herein by this reference. These vectors are capable of binding to solid tumors that express higher levels of high affinity laminin receptors.

The use of peptidomimetics that act as mimetics of Smac and inhibit IAPs to promote apoptosis is described in United States Patent Application Publication No. 2011/0305777 by Condon et al., incorporated herein by this reference.

The use of nuclear transport modulators, especially inhibitors of Crm1, is described in United States Patent Application Publication No. 2011/0275607 by Shacham et al., incorporated herein by this reference. These inhibitors of Crm1 include, but are not limited to, (Z)-3-[3-(3-chlorophenyl)[1,2,4]-triazol-1-yl]-acrylic acid ethyl ester, (E)-3-[3-(3-chlorophenyl)[1,2,4]-triazol-1-yl]-acrylic acid ethyl ester, (Z)-3-[3-(3-chlorophenyl)-[1,2,4]-triazol-1-yl]-acrylic acid isopropyl ester, (E)-3-[3-(3-chlorophenyl)-[1,2,4]-triazol-1- yl]-acrylic acid isopropyl ester, (Z)-3-[3-(3-chlorophenyl)-[1,2,4]-triazol-1-yl]-acrylic acid t-butyl ester, (Z)-3-[3-(3-chlorophenyl)-[1,2,4]-triazol-1-yl]-acrylic acid t-butyl ester, (E)-3-[3-(3-chlorophenyl)-[1,2,4]-triazol-1-yl]-N-phenyl-acrylamide, (E)-N-(2-chlorophenyl)-3-[3-(3-chlorophenyl)-[1,2,4]-triazol-1-yl]-acrylamide, (4-{(E)-3-[3-(3-chlorophenyl)[1,2,4]-triazol-1-yl]-acryloylamino}-phenyl-)-carbamic acid t-butyl ester, (E)-3-[3-(3-chlorophenyl)-[1,2,4]-triazol-1-yl]-N-(4-methoxyphenyl)-acrylamide, (E)-3-[3-(3-chlorophenyl)-[1,2,4]-triazol-1-yl]-N-methyl-N-phenyl-acrylamide, and (E)-N-(4-aminophenyl)-3-[3-(3-chlorophenyl)-[1,2,4]-triazol-1-yl]-acrylamide.

The use of tyrosine kinase inhibitors is described in United States Patent Application Publication No. 2011/0206661 by Zhang et al., which is directed to trimethoxy-phenyl inhibitors of tyrosine kinase, and in United States Patent Application Publication No. 2011/0195066, which is directed to quinoline inhibitors of tyrosine kinase, both of which are incorporated herein by this reference. The use of tyrosine kinase inhibitors is also described in United States Patent Application Publication No. 2011/053968 by Zhang et al., incorporated herein by this reference, which is directed to aminopyridine inhibitors of tyrosine kinase. The use of tyrosine kinase inhibitors is also described in United States Patent Application Publication No. 2010/0291025, incorporated herein by this reference, which is directed to indazole inhibitors of tyrosine kinase. The use of tyrosine kinase inhibitors is also described in United States Patent Application Publication No. 2010/0190749 by Ren et al., incorporated herein by this reference; these tyrosine kinase inhibitors are benzoxazole compounds; compounds of this class can also inhibit mTOR and lipid kinases such as phosphoinositide 3-kinases. The use of tyrosine kinase inhibitors is also described in U.S. Pat. No. 8,242,270 by Lajeunesse et al., incorporated herein by this reference; these tyrosine kinase inhibitors are 2-aminothiazole-5-aromatic carboxamides.

The use of an acid ceramidase inhibitor and a choline kinase inhibitor is described in United States Patent Application Publication No. 2011/0256241 by Ramirez de Molina et al., incorporated herein by this reference.

The use of anti-CS1 antibodies is described in United States Patent Application Publication No. 2011/0165154 by Afar, incorporated herein by this reference.

The use of protein kinase CK2 inhibitors is described in United States Patent Application Publication No. 2011/0152240 by Haddach et al., incorporated herein by this reference. These protein kinase CK2 inhibitors include pyrazolopyrimidines. Additional protein kinase CK2 inhibitors, including tricyclic compounds, are described in United States Patent Application Publication No. 2011/0071136 by Haddach et al., incorporated herein by this reference; these protein kinase CK2 inhibitors may also inhibit Pim kinases or other kinases. Additional protein kinase CK2 inhibitors, including heterocycle-substituted lactams, are also described in United States Patent Application Publication No. 2011/0071115 by Haddach et al., incorporated herein by this reference; these protein kinase CK2 inhibitors may also inhibit Pim kinases or other kinases.

The use of anti-guanylyl cyclase C (GCC) antibodies is described in United States Patent Application Publication No. 2011/0110936 by Nam et al., incorporated herein by this reference.

The use of histone deacetylase inhibitors is described in United States Patent Application Publication No. 2011/0105474 by Thaler et al., incorporated herein by this reference. These histone deacetylase inhibitors include, but are not limited to, (E)-N-hydroxy-3-{4-[(E)-3-(4-methyl-piperazin-1-yl)-3-oxo-propenyl]-phenyl}-acrylamide; (E)-N-hydroxy-3-{3-[(E)-3-(4-methyl-piperazin-1-yl)-3-oxo-propenyl]-phenyl}-acrylamide; (E)-N-hydroxy-3-{3-[(E)-3-oxo-3-(4-phenyl-piperazin-1-yl)-propenyl]-phenyl}-acrylamide; (E)-3-[3-((E)-3-[1,4']bipiperidinyl-1'-yl-3-oxo-propenyl)-phenyl]-N-hydroxy-acrylamide; (E)-N-hydroxy-3-{3-[(E)-3-oxo-3-(cis-3,4,5-trimethyl-piperazin-1-yl)-propenyl]-phenyl}-acrylamide; (E)-3-{3-[(E)-3-((1S,4S)-5-methyl-2,5-diaza-bicyclo[2.2.1]hept-2-yl)-3-oxo-propenyl]-phenyl}-N-hydroxy-acrylamide; (E)-N-hydroxy-3-{4-[(E)-3-oxo-3-(4-phenyl-piperazin-1-yl)-propenyl]-phenyl}-acrylamide; (E)-3-[4-((E)-3-[1,4']bipiperidinyl-1'-yl-3-oxo-propenyl)-phenyl]-N-hydroxy-acrylamide; (E)-N-hydroxy-3-{4-[(E)-3-oxo-3-(cis-3,4,5-trimethyl-piperazin-1-yl)-propenyl]-phenyl}-acrylamide; (E)-N-hydroxy-3-{4-[(E)-3-oxo-3-((1S,4S)-5-methyl-2,5-diaza-bicyclo[2.2.1]hept-2-yl)-propenyl]-phenyl}-acrylamide; (E)-N-hydroxy-3-{5-[(E)-3-oxo-3-(4-phenyl-piperazin-1-yl)-propenyl]-pyridin-2-yl}-acrylamide; (E)-N-hydroxy-3-{5-[(E)-3-(4-methyl-piperazin-1-yl)-3-oxo-propenyl]-pyridin-2-yl}-acrylamide; (E)-N-hydroxy-3-{6-[(E)-3-oxo-3-(4-phenyl-piperazin-1-yl)-propenyl]-pyridin-2-yl}-acrylamide; (E)-N-hydroxy-3-{6-[(E)-3-(4-methyl-piperazin-1-yl)-3-oxo-propenyl]-pyridin-2-yl}-acrylamide; (E)-3-(6-{(E)-3-[4-(3-chloro-phenyl)-piperazin-1-yl]-3-oxo-propenyl}-pyridin-2-yl)-N-hydroxy-acrylamide; (E)-3-{6-[(E)-3-(4-benzoyl-piperazin-1-yl)-3-oxo-propenyl]-pyridin-2-yl}-N-hydroxy-acrylamide hydrochloride; (E)-3-(6-{(E)-3-[4-(2-chloro-phenyl)-piperazin-1-yl]-3-oxo-propenyl}-pyridin-2-yl)-N-hydroxy-acrylamide hydrochloride; (E)-N-hydroxy-3-{6-[(E)-3-oxo-3-(4-phenyl-piperidin-1-yl)-propenyl]-pyridin-2-yl}-acrylamide hydrochloride; (E)-N-hydroxy-3-{6-[(E)-3-oxo-3-(4-pyrimidin-2-yl-piperazin-1-yl)-propenyl]-pyridin-2-yl}-acrylamide hydrochloride; (E)-3-(6-{(E)-3-[4-(4-chloro-phenyl)-piperazin-1-yl]-3-oxo-propenyl}-pyridin-2-yl)-N-hydroxy-acrylamide hydrochloride; and (E)-3-{6-[(E)-3-(4-benzyl-piperazin-1-yl)-3-oxo-propenyl]-pyridin-2-yl}-N-hydroxy-acrylamide hydrochloride. Additional histone deacetylase inhibitors, including spirocyclic derivatives, are described in United States Patent Application Publication No. 2011/039840 by Varasi et al., incorporated herein by this reference. Prodrugs of histone deacetylase inhibitors are described in U.S. Pat. No. 8,227,636 to Miller et al., incorporated herein by this reference. Histone deacetylase inhibitors are described in U.S. Pat. No. 8,222,451 to Kozikowski et al., incorporated herein by this reference. Histone deacetylase inhibitors, including disubstituted aniline compounds, are also described in U.S. Pat. No. 8,119,685 to Heidebrecht et al., incorporated herein by this reference. Histone deacetylase inhibitors, including aryl-fused spirocyclic compounds, are also described in U.S. Pat. No. 8,119,852 to Hamblett et al., incorporated herein by this reference.

The use of cannabinoids is disclosed in United States Patent Application Publication No. 2011/0086113 by Velasco Diez et al., incorporated herein by this reference. Suitable cannabinoids include, but are not limited to, tetrahydrocannabinol and cannabidiol.

The use of glucagon-like peptide-1 (GLP-1) receptor agonists is described in United States Patent Application Publication No. 2011/0046071 by Karasik et al., incorporated herein by this reference. A suitable GLP-1 receptor agonist is exendin-4.

The use of inhibitors of anti-apoptotic proteins Bcl-2 or Bcl-xL is described in United States Patent Application Publication No. 2011/0021440 by Martin et al., incorporated herein by this reference.

The use of Stat3 pathway inhibitors is described in United States Patent Application Publication No. 2010/0310503 by Li et al., incorporated herein by this reference. These Stat3 pathway inhibitors include, but are not limited to, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, and 2-ethyl-naphtho[2,3-b]furan-4,9-dione.

The use of inhibitors of polo-like kinase 1 (Plk1) is described in United States Patent Application Publication No. 2010/0278833 by Stengel et al., incorporated herein by this reference. These inhibitors include, but are not limited to, thiophene-imidazopyridines, including, but not limited to, 5-(6-chloro-1H-imidazo[4,5-c]pyridin-1-yl)-3-{[2-(trifluoromethyl)benzyl]oxy}thiophene-2-carboxamide, 5-(1H-imidazo[4,5-c]pyridin-1-yl)-3-{[2-(trifluoromethyl)benzyl]oxy}thiophene-2-carboxamide, 5-(3H-imidazo[4,5-c]pyridin-3-yl)-3-{[2-(trifluoromethyl)benzyl]oxy}thiophene-2-carboxamide, 1-(5-carbamoyl-4-{[2-(trifluoromethyl)benzyl]oxy}-2-thienyl)-N-(2-methoxyethyl)-1H-imidazo[4,5-c]pyridine-6-carboxamide, 1-(5-carbamoyl-4-{[2-(trifluoromethyl)benzyl]oxy}-2-thienyl)-N-(2-morpholin-4-ylethyl)-1H-imidazo[4,5-c]pyridine-6-carboxamide, 5-{6-[diethylamino)methyl]-1H-imidazo[4,5-c]pyridin-1-yl}-3-{[2-(trifluoromethyl)benzyl]oxy}thiophene-2-carboxamide, 5-{6-[(cyclopropylamino)methyl]-1H-imidazo[4,5-c]pyridin-1-yl}-3-{[2-(trifluoromethyl)benzyl]oxy}thiophene-2-carboxamide, 5-{6-[(4-methylpiperazin-1-yl)methyl]-1H-imidazo[4,5-c]pyridin-1-yl}-3-{[2-(trifluoromethyl)benzyl]oxy}thiophene-2-carboxamide, and 5-[6-(hydroxymethyl)-1H-imidazo[4,5-c]pyridin-1-yl]-3-{[2-(trifluoromethyl)benzyl]oxy}thiophene-2-carboxamide.

The use of GBPAR1 activators is described in United States Patent Application Publication No. 2010/0261758 by Arista et al., incorporated by this reference. These GBPAR1 activators include, but are not limited to, heterocyclic amides. These compounds include, but are not limited to, N-(3,5-dichlorophenyl)-3-methyl-N-naphthalen-2-ylmethyl-isonicotinamide, (3,5-dichlorophenyl)-N-(2-methoxybenzyl)-3-methyl-isonicotinamide, 3-methyl-N-phenyl-N-pyridin-3-ylmethyl-isonicotinamide, N-naphthalen-2-ylmethyl-1-oxy-N-phenyl-isonicotinamide, N-(3,5-dichlorophenyl)-3-methyl-N-(2-trifluoromethoxybenzyl)-isonicotinamide, 4-methyl-oxazole-5-carboxylic acid benzyl-phenyl-amide, N-benzyl-N-phenylisonicotinamide, N-benzyl-N-β-tolylisonicotinamide, N-benzyl-2-fluoro-N-phenylisonicotinamide, N-benzyl-3,5-dichloro-N-phenyl-isonicotinamide, N-benzyl-2-chloro-N-phenyl-isonicotinamide, N-benzyl-2-chloro-6-methyl-N-phenyl-isonicotinamide, N-benzyl-3-methyl-N-phenyl-isonicotinamide, N-benzyl-3-chloro-N-phenyl-isonicotinamide, N-benzyl-2,5-dichloro-N-phenyl-isonicotinamide, N-benzyl-2-methyl-N-phenyl-isonicotinamide, N-benzyl-2-cyano-N-phenyl-isonicotinamide, N-benzyl-N-phenethyl-isonicotinamide, N-benzyl-N-(2-fluoromethoxy-phenyl)-isonicotinamide, and N-benzyl-N-(4-chlorophenyl)-isonicotinamide. Additional GBPAR1 activators are described in United States Patent Application Publication No. 2010/0048579 by Arista, incorporated herein by this reference, including pyridazine, pyridine, and pyrane derivatives.

The use of modulators of serine-threonine protein kinase and poly(ADP-ribose) polymerase (PARP) activity is described in United States Patent Application Publication No. 2009/0105233 by Chua et al. and in United States Patent Application Publication No. 2010/0173013 by Drygin et al., both incorporated herein by this reference. The serine-threonine protein kinase can be, but is not limited to, CK2, CK2a2, Pim-1, CDK1/cyclinB, c-RAF, Mer, MELK, DYRK2, Flt3, Flt3 (D835Y), Flt4, HIPK3, HIPK2, and ZIPK.

The use of taxanes is described in United States Patent Application Publication No. 2010/0166872 by Singh et al., incorporated herein by this reference. The taxane can be, but is not limited to, paclitaxel or docitaxel.

The use of inhibitors of dihydrofolate reductase is described in United States Patent Application Publication No. 2010/0150896 by Gant et al., incorporated herein by this reference. These inhibitors of dihydrofolate reductase include, but are not limited to, diaminoquinazolines.

The use of inhibitors of aromatase is described in United States Patent Application Publication No. 2010/0111901 by Gant et al., incorporated herein by this reference. These inhibitors of aromatase include, but are not limited to, triazoles.

The use of benzimidazole-based anti-neoplastic agents is described in United States Patent Application Publication No. 2010/0098691 by Goh et al., incorporated herein by this reference. The benzimidazole-based anti-neoplastic agent can be, but is not limited to, (E)-3-[1-(3-dimethylamino-2,2-dimethyl-propyl)-2-isopropyl-1H-benzimidazol-5-yl]-N-hydroxy-acrylamide, (E)-3-[2-butyl-1-(3-dimethylamino-2,2-dimethyl-propyl)-1H-benzimidazol-5-yl]-N-hydroxy-acrylamide, (E)-3-[1-(3-dimethylamino-2,2-dimethyl-propyl)-2-(2-methylsulfanyl-ethyl)-1H-benzimidazol-5-yl]-N-hydroxy-acrylamide, (E)-3-[1-(3-dimethylamino-2,2-dimethyl-propyl)-2-ethoxymethyl-1H-benzimidazol-5-yl]-N-hydroxy-acrylamide, (E)-3-[1-(3-dimethylamino-2,2-dimethyl-propyl)-2-isobutyl-1H-benzimidazol-5-yl]-N-hydroxy-acrylamide, (E)-3-[1-(2-diethylamino-ethyl)-2-isobutyl-1H-benzimidazol-5-yl]-N-hydroxy-acrylamide, (E)-3-[2-butyl-1-(2-diethylamino-ethyl)-1H-benzimidazol-5-yl]-N-hydroxy-acrylamide, (E)-3-[2-but-3-ynyl-1-(3-dimethylamino-2,2-dimethyl-propyl)-1H-benzimidazol-5-yl]-N-hydroxy-acrylamide, (E)-3-[2-but-3-enyl-1-(3-dimethylamino-2,2-dimethyl-propyl)-1H-benzimidazol-5-yl]-N-hydroxy-acrylamide, (E)-3-[2-but-3-enyl-1-(2-diethylamino-ethyl)-1H-benzimidazol-5-yl]-N-hydroxy-acrylamide, (E)-3-[2-but-3-ynyl-1-(2-diethylamino-ethyl)-1H-benzimidazol-5-yl]-N-hydroxy-acrylamide, (E)-3-[1-(3-dimethylamino-2,2-dimethyl-propyl)-2-(3,3,3-trifluoro-propyl)-1H-benzimidazol-5-yl]-N-hydroxy-acrylamide (E)-3-[1-(2-diethylamino-ethyl)-2-(3,3,3-trifluoro-propyl)-1H-benzimidazol-5-yl]-N-hydroxy-acrylamide, (E)-3-[1-(2-diethylamino-ethyl)-2-ethoxymethyl-1H-benzimidazol-5-yl]-N-hydroxy-acrylamide, (E)-3-[1-(3-dimethylamino-2,2-dimethyl-propyl)-2-methyl-1H-benzimidazol-5-yl]-N-hydroxy-acrylamide, (E)-3-[1-(2-diethylamino-ethyl)-2-(2,2-dimethyl-propyl)-1H-benzimidazol-5-yl]-N-hydroxy-acrylamide, (E)-N-hydroxy-3-[1-(3-isopropylamino-propyl)-2-(3,3,3-trifluoro-propyl)-1-H-benzimidazol-5-yl]-acrylamide, (E)-3-[2-(2,2-dimethyl-propyl)-1-(2-isopropylamino-ethyl)-1H-benzimidazol-5-yl]-N-hydroxy-acrylamide, (E)-3-[1-(2-diisopropylamino-ethyl)-2-(2,2-dimethyl-propyl)-1H-benzimidazol-5-yl]-N-hydroxy-acrylamide, (E)-3-[1-(2-diisopropylamino-ethyl)-2-isobutyl-1H-benzimidazol-5-yl]-N-hydroxy-acrylamide, (E)-3-[1-(3-dimethylamino-2,2-dimethyl-propyl)-2-hex-3-enyl-1H-benzimidazol-5-yl]-N-hydroxy-acrylamide, (E)-3-[1-(3-dimethylamino-2,2-dimethyl-propyl)-2-(2,4,4-trimethyl-pentyl)-1H-benzimidazol-5-yl]-N-hydroxy-acrylamide, (E)-3-[2-cyclohexyl-1-(3-dimethylamino-2,2-dimethyl-propyl)-1H-benzimidazol-5-yl]-N-hydroxy-acrylamide, (E)-3-[2-bicyclo[2.2.1]hept-5-en-2-yl-1-(3-dimethylamino-2,2-dimethyl-propyl)-1H-benzimidazol-5-yl]-N-hydroxy-acrylamide, (E)-3-[1-(2-diethylamino-ethyl)-2- hex-3-enyl-1H-benzimidazol-5-yl]-N-hydroxy-acrylamide, (E)-3-[1-(2-diisopropylamino-ethyl)-2-hex-3-enyl-1H-benzimidazol-5-yl]-N-hydroxy-acrylamide, (E)-3-[2-hex-3-enyl-1-(2-isopropylamino-ethyl)-1H-benzimidazol-5-yl]-N-hydroxy-acrylamide, (E)-3-[2-hex-3-enyl-1-(3-isopropylamino-propyl)-1H-benzimidazol-5-yl]-N-hydroxy-acrylamide, (E)-3-[1-(2-ethylamino-ethyl)-2-hex-3-enyl-1H-benzimidazol-5-yl]-N-hydroxy-acrylamide, (E)-3-[1-(2-diethylamino-ethyl)-2-hexyl-1H-benzimidazol-5-yl]-N-hydroxy-acrylamide, (E)-N-hydroxy-3-[1-(3-isopropylamino-propyl)-2-(2,4,4-trimethyl-pentyl)-1H-benzimidazol-5-yl]-acrylamide, (E)-3-[2-(2,2-dimethyl-propyl)-1-(3-isopropylamino-propyl)-1H-benzimidazol-5-yl]-N-hydroxy-acrylamide, (E)-3-[1-(2-diisopropylamino-ethyl)-2-(3,3,3-trifluoro-propyl)-1H-benzimidazol-5-yl]-N-hydroxy-acrylamide, and (E)-N-hydroxy-3-[2-isobutyl-1-(2-isopropylamino-ethyl)-1H-benzimidazol-5-yl]-acrylamide.

The use of $O^6$-methylguanine-DNA-methyltransferase (MGMT) inhibitors is described in United States Patent Application 2010/0093647 by Liu et al., incorporated herein by this reference. Suitable MGMT inhibitors include, but are not limited to, $O^6$-benzylguanine, $O^6$-2-fluoropyridinylmethylguanine, $O^6$-3-iodobenzyl guanine, $O^6$-4-bromophenylguanine, $O^6$-5-iodophenylguanine $O^6$-benzyl-8-oxoguanine, $O^6$-(p-chlorobenzyl)guanine, $O^6$-(p-methylbenzyl) guanine, $O^6$-(p-bromobenzyl)guanine, $O^6$-(p-isopropylbenzyl)guanine, $O^6$-(3,5-dimethylbenzyl)guanine, $O^6$-(p-n-butylbenzyl)guanine, $O^6$-(p-hydroxymethybenzyl)guanine, $O^6$-benzylhypoxanthine, $N^2$-acetyl-$O^6$-benzylguanine, $N^2$-acetyl-$O^6$-benzyl-8-oxo-guanine, 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, $O^6$-benzyl-7,8-dihydro-8-oxoguanine, 2,4,5-triamino-6-benzyloxyprimidine, $O^6$-benzyl-9-[(3-oxo-5α-androstan-17β-yloxy-carbonylmethyl]guanine, $O^6$-benzyl-9-[(3-oxo-4-androsten-17β-yloxycarbonyl)methyl(guanine, 8-amino-$O^6$-benzyl-guanine (8-amino-BG), 2,4-diamino-6-benzyloxy-5-nitrosopyrimidine, 2,4-diamino-6-benzyloxy-5-nitropyrimidine, and 2-amino-4-benzyloxy-5-nitropyrimidine.

The use of CCR9 inhibitors is described in United States Patent Application Publication No. 2010/0075963 by Lehr et al., incorporated herein by this reference. These CCR9 inhibitors include, but are not limited to, benzylsulfonylindoles.

The use of acid sphingomyelinase inhibitors is described in United States Patent Application Publication No. 2010/0022482 by Baumann et al., incorporated herein by this reference. Typically, these compounds are biphenyl derivatives.

The use of peptidomimetic macrocycles is described in United States Patent Application Publication No. 2009/0275519 by Nash et al., incorporated herein by this reference.

The use of cholanic acid amides is described in United States Patent Application Publication No. 2009/0258847 by Schreiner et al., incorporated herein by this reference. These cholanic acid amides include, but are not limited to, substituted 4-(3-hydroxy-10,13-hydroxymethyl-hexadecahydrocyclopenta(a)-phenanthren-17-yl)pentanoic acid amides.

The use of substituted oxazaphosphorines is described in United States Patent Application Publication No. 2009/0202540, incorporated herein by this reference. The oxazaphosphorine can be, but is not limited to, ifosphamide and cyclophosphamide.

The use of anti-TWEAK receptor antibodies is described in United States Patent Application Publication No. 2009/0074762 by Culp, incorporated herein by this reference. The TWEAK receptor is a member of the tumor necrosis receptor superfamily and is expressed on the surface of cancer cells in a number of solid tumors.

The use of ErbB3 binding protein is described in United States Patent Application Publication No. 2008/0269133 by Zhang et al., incorporated herein by this reference.

The use of a glutathione S-transferase-activated (GST-activated) anti-neoplastic compound is described in United States Patent Application Publication No. 2008/0166428 by Brown et al., incorporated herein by this reference. A preferred GST-activated anti-neoplastic compound is canfosfamide.

The use of substituted phosphorodiamidates is described in United States Patent Application Publication No. 2008/0125398 by Ma et al., incorporated herein by this reference, which describes 2-{[2-(substituted amino)ethyl]sulfonyl}ethyl N,N,N',N'-tetrakis(2-chloroethyl)-phosphorodiamidates, and in United States Patent Application Publication No. 2008/0125397 by Lui et al., incorporated herein by this reference, which describes 2-({2-oxo-2-[(pyridin-3-ylmethyl)amino]ethyl}sulfonyl)ethyl N,N,N',N'-tetrakis(2-chloroethyl)phosphorodiamidate. The use of substituted phosphorodiamidates is also described in United States Patent Application Publication No. 2008/0039429 by Allen et al., incorporated herein by this reference, which describes sulfonylethyl and thioethyl phosphorodiamidates.

The use of inhibitors of MEKK protein kinase is described in United States Patent Application Publication No. 2006/0100226 by Sikorski et al., incorporated herein by this reference. These inhibitors include, but are not limited to, 2-thiopyrimidinones, such as 2-[3-(3,4-dichloro-benzylamino)-benzylsulfanyl]-4-(3-methoxy-phenyl)-6-oxo-1,6-dihydro-pyrimidine-5-carbonitrile, 2-[3-(3,4-dichloro-benzylamino)-benzylsulfanyl]-4-(3,4-dimethoxy-phenyl)-6-oxo-1,6-dihydro-pyrimidine-5-carbonitrile, and 2-[3-(3,4-dichloro-benzylamino)-benzylsulfanyl-4-(4-methoxy-3-thiophen-2-yl-phenyl)-6-oxo-1,6-dihydro-pyrimidine-5-carbonitrile.

The use of COX-2 inhibitors is described in United States Patent Application Publication No. 2004/0072889 by Masferrer et al., incorporated herein by this reference. Suitable COX-2 inhibitors include, but are not limited to, celecoxib, parecoxib, deracoxib, rofecoxib, etoricoxib, valdecoxib, and meloxicam.

The use of cimetidine and N-acetylcysteine is described in United States Patent Application Publication No. 2003/0158118 by Weidner, incorporated herein by this reference. Derivatives of cimetidine or N-acetylcysteine can also be used.

The use of an anti-IL-6 receptor antibody is described in United States Patent Application Publication No. 2002/0131967 by Nakamura et al., incorporated herein by this reference. The antibody can be a humanized antibody.

The use of an antioxidant is described in United States Patent Application Publication No. 2001/0049349 by Chinery et al., incorporated herein by this reference. Suitable antioxidants include, but are not limited to, pyrrolidinedithiocarbamate, probucol (4,4'-(isopropylidenedithio)bis(2,6-di-t-butylphenol), vitamin C, vitamin E, and 6-hydroxy-2,5,7,8-tetramethylchroman-2-carboxylic acid.

The use of an isoxazole inhibitor of tubulin polymerization is described in U.S. Pat. No. 8,269,017 by Sun et al., incorporated herein by this reference. Suitable isoxazole inhibitors of tubulin polymerization include, but are not limited to, 2-amino-N-(2-methoxy-5-[5-(3,4,5-trimethoxy-phenyl)-isoxazol-4-yl)-phenyl)acetamide hydrochloride; 2-amino-3-hydroxy-N-(2-methoxy-5-[5-(3,4,5-trimethoxyphenyl)isoxazol-4-yl)-phenyl)propanamide hydrochloride; 2-amino-N-(2-methoxy-5-[5-(3,4,5-trimethoxyphenyl)isoxazol-4-yl)-phenyl)propanamide; 2-amino-N-(2-methoxy-5-[5-(3,4,5-trimethoxyphenyl)-isoxazol-4-yl)-phenyl)-4-(methylthio)butanamide hydrochloride; 2-amino-N-(2-methoxy-5-[5-(3,4,5-trimethoxyphenyl)-isoxazol-4-yl)-phenyl)butanamide; 2-amino-N-(2-methoxy-5-[5-(3,4,5-trimethoxyphenyl)-isoxazol-4-yl)-phenyl)-3-phenylpropanamide hydrochloride; 2-amino-N-(2-methoxy-5-[5-(3,4,5-trimethoxyphenyl)-isoxazol-4-yl)-phenyl)-4-methylpentanamide hydrochloride; 2-amino-N-(2-methoxy-5-[5-(3,4,5-trimethoxy-phenyl)-isoxazol-4-yl)-phenyl)-3-(4-methoxyphenyl)propanamide hydrochloride; 1-{2-methoxy-5-[5-(3,4,5-trimethoxy-phenyl)-isoxazol-4-yl]-phenylcarbamoyl}-2-methyl-propyl-ammonium chloride; 1-{2-methoxy-5-[5-(3,4,5-trimethoxyphenyl)-isoxazol-4-yl]-phenylcarbamoyl}-2-methyl-butyl-ammonium chloride; 2-hydroxy-1-{2-methoxy-5-[5-(3,4,5-trimethoxyphenyl)-isoxazol-4-yl]-phenylcarbamoyl}-propyl-ammonium chloride; 2-(4-hydroxyphenyl)-1-{2-methoxy-5-[5-(3,4,5-trimethoxyphenyl)-isoxazol-4-yl]-phenylcarbamoyl}-ethyl-ammonium chloride; C-{2-methoxy-5-[5-(3,4,5-trimethoxyphenyl)-isoxazol-4-yl]-phenylcarbamoyl}-C-phenyl-methyl-ammonium chloride; 2-(1H-indol-2-yl)-1-{2-methoxy-5-[5-(3,4,5-trimethoxyphenyl)-isoxazol-4-yl]-phenylcarbamoyl}-ethyl-ammonium chloride; 2-benzofuran-2-yl-1-{2-methoxy-5-[5-(3,4,5-trimethoxyphenyl)-isoxazol-4-yl]-phenylcarbamoyl}-ethyl-ammonium chloride; 2-carboxyl-1-{2-methoxy-5-[5-(3,4,5-trimethoxyphenyl)-isoxazol-4-yl]-phenylcarbamoyl}-ethyl-ammonium chloride; 3-carboxyl-1-{2-methoxy-5-[5-(3,4,5-trimethoxyphenyl)-isoxazol-4-yl]-phenylcarbamoyl}-propyl-ammonium chloride; 3-carbamoyl-1-{2-methoxy-5-[5-(3,4,5-trimethoxyphenyl)-isoxazol-4-yl]-phenylcarbamoyl}-propyl-ammonium chloride; 2-carbamoyl-1-{2-methoxy-5-[5-(3,4,5-trimethoxyphenyl)-isoxazol-4-yl]-phenylcarbamoyl}-ethyl-ammonium chloride; and 2-(3H-imidazol-4-yl)-1-{2-methoxy-5-[5-(3,4,5-trimethoxyphenyl)-isoxazol-4-yl]-phenylcarbamoyl}-ethyl-ammonium chloride.

The use of pyridazinone PARP inhibitors is described in U.S. Pat. No. 8,268,827 by Branca et al., incorporated herein by this reference. Pyridazinone PARP inhibitors include, but are not limited to, 6-{4-fluoro-3-[(3-oxo-4-phenylpiperazin-1-yl)carbonyl]benzyl}-4,5-dimethyl-3-oxo-2,3-dihydropyridazin-1-ium trifluoroacetate; 6-{3-[(4-cyclohexyl-3-oxopiperazin-1-yl)carbonyl]-4-fluorobenzyl}-4,5-dimethyl-3-oxo-2,3-dihydropyridazin-1-ium trifluoroacetate; 6-{3-[(4-cyclopentyl-3-oxopiperazin-1-yl)carbonyl]-4-fluorobenzyl}-4,5-dimethylpyridazin-3(2H)-one; 6-{4-fluoro-3-[(3-oxo-4-phenylpiperazin-1-yl)carbonyl]benzyl}-4,5-dimethylpyridazin-3(2H)-one hydrochloride; 4-ethyl-6-{4-fluoro-3-[(3-oxo-4-phenylpiperazin-1-yl)carbonyl]benzyl}pyridazin-3(2H)-one trifluoroacetate; 6-{3-[(4-cyclohexyl-3-oxopiperazin-1-yl)carbonyl]-4-fluorobenzyl}-4-ethyl pyridazin-3(2H)-one trifluoroacetate; 3-{4-fluoro-3-[(4-methyl-3-oxopiperazin-1-yl)carbonyl]benzyl}-4,5-dimethyl-6-oxo-1,6-dihydropyridazin-1-ium trifluoroacetate; 3-(4-fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate; 6-(3-{[4-(2-chlorophenyl)-3-oxopiperazin-1-yl]carbonyl}-4-fluorobenzyl)-4,5-dimethyl-3-oxo-2,3-dihydropyridazin-1-ium trifluoroacetate; 6-(3-{[4-(3-chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate; and 6-(3-{[4-(3,4-difluorophenyl)-3-oxopiperazin-1-yl]carbonyl}-4-fluorobenzyl)-4,5-dimethyl-3-oxo-2,3-dihydropyridazin-1-ium trifluoroacetate. Other PARP inhibitors are described in U.S. Pat. No. 8,143,447 by Moore et al., incorporated herein by this reference; these compounds include nitrobenzamide derivatives.

The use of Aurora protein kinase inhibitors is described in U.S. Pat. No. 8,268,811 to Mortimore et al., incorporated herein by this reference. The Aurora protein kinase inhibitors include, but are not limited to, thiazoles and pyrazoles. The use of Aurora protein kinase inhibitors is also described in U.S. Pat. No. 8,129,399 to Binch et al., incorporated herein by this reference; these Aurora protein kinase inhibitors include, but are not limited to, aminopyridines.

The use of peptides binding to prostate-specific membrane antigen (PSMA) is described in U.S. Pat. No. 8,258,256 to Denmeade et al., incorporated herein by this reference.

The use of CD19 binding agents is described in U.S. Pat. No. 8,242,252 to McDonagh et al., incorporated herein by this reference. These CD19 binding agents include, but are not limited to, anti-CD19 antibodies.

The use of benzodiazepines is described in U.S. Pat. No. 8,242,109 to Glick, incorporated herein by this reference.

The use of Toll-like receptor (TLR) agonists is described in U.S. Pat. No. 8,242,106 to Howbert et al., incorporated herein by this reference. Suitable TLR agonists include, but are not limited to, (1E,4E)-2-amino-N,N-dipropyl-8-(4-(pyrrolidine-1-carbonyl)phenyl)-3H-benzo[b]azepine-4-carboxamide.

The use of bridged bicyclic sulfamides is described in U.S. Pat. No. 8,242,103 to Lewis et al., incorporated herein by this reference.

The use of inhibitors of epidermal growth factor receptor (EGFR) kinase is described in U.S. Pat. No. 8,242,080 to Kuriyan et al., incorporated herein by this reference. Typically, these inhibitors of EGFR kinase target the asymmetric activating dimer interface.

The use of ribonucleases of the T2 family having actin-binding activity is described in U.S. Pat. No. 8,236,543 to Roiz et al., incorporated herein by this reference. Typically, the ribonuclease binds actin in either its active or inactive ribonucleolytic form.

The use of myrsinoic acid A or an analog thereof is described in U.S. Pat. No. 8,232,318 to Lee et al., incorporated herein by this reference.

The use of an inhibitor of a cyclin-dependent kinase is described in U.S. Pat. No. 8,227,605 to Shipps et al.; these inhibitors include, but are not limited to, 2-aminothiazole-4-carboxylic amides. Use of an inhibitor of a cyclin-dependent kinase is also described in U.S. Pat. No. 7,700,773 to Mallams et al., incorporated herein by this reference; these inhibitors include, but are not limited to, 4-cyano, 4-amino, and 4-aminomethyl derivatives of pyrazolo[1,5-a]pyridine, pyrazolo[1,5-c]pyrimidine, and 2H-indazole compounds and 5-cyano, 5-amino, and 5-aminomethyl derivatives of imidazo[1,2-a]pyridine and imidazo[1,5-a]pyrazine compounds.

The use of an inhibitor of the interaction between p53 and MDM2 is described in U.S. Pat. No. 8,222,288 to Wang et al., incorporated herein by this reference.

The use of inhibitors of the receptor tyrosine kinase MET is described in U.S. Pat. No. 8,222,269 to Dinsmore et al., incorporated herein by this reference. These inhibitors of the receptor tyrosine kinase MET include, but are not limited to, 5H-benzo[4,5]cyclohepta[1,2-b]pyridine derivatives. Inhibitors of the receptor tyrosine kinase MET are also described in U.S. Pat. No. 8,207,186 to Jewell et al., incorporated herein by this reference. These compounds include, but are not limited to, benzocycloheptapyridines, including 5H-benzo[4,5]cyclohepta[1,2-b]pyridine derivatives.

The use of largazole or largazole analogs is described in U.S. Pat. No. 8,217,076 to Williams et al., incorporated herein by this reference.

The use of inhibitors of the protein kinase AKT is described in U.S. Pat. No. 8,207,169 to Furuyama et al., incorporated herein by this reference; these inhibitors include, but are not limited to, triazolopyridopyridines, including substituted [1,2,4]triazolo[4',3':1,6]pyrido[2,3-b]pyrazines.

The use of 2'-fluoro-5-methyl-β-L-arabinofuranosyluridine or L-deoxythymidine is described in U.S. Pat. No. 8,207,143 to Cheng, incorporated herein by this reference.

The use of compounds that modulate HSP90 activity is described in U.S. Pat. No. 8,188,075 to Ying et al., incorporated herein by this reference. These compounds include, but are not limited to, substituted triazoles, including 3-(2-hydroxyphenyl)-4-(naphthalen-1-yl)-5-mercaptotriazole; 3-(2,4-dihydroxyphenyl)-4-[4-(2-methoxyethoxy)-naphthalen-1-yl]-5-mercaptotriazole; 3-(2,4-dihydroxyphenyl)-4-(2-methyl-4-bromophenyl)-5-mercaptotriazole; 3-(3,4-dihydroxyphenyl)-4-(6-methoxy-naphthalen-1-yl)-5-mercaptotriazole; 3-(3,4-dihydroxyphenyl)-4-(6-ethoxy-naphthalen-1-yl)-5-mercaptotriazole; 3-(3,4-dihydroxyphenyl)-4-(6-propoxy-naphthalen-1-yl)-5-mercaptotriazole; 3-(2,4-dihydroxy-5-ethyl-phenyl)-4-(5-methoxy-naphthalen-1-yl)-5-mercaptotriazole; 3-(3,4-dihydroxyphenyl)-4-(6-isopropoxy-naphthalen-1-yl)-5-mercaptotriazole; 3-(2,4-dihydroxyphenyl)-4-(2,6-diethylphenyl)-5-mercaptotriazole; 3-(2,4-dihydroxyphenyl)-4-(2-methyl-6-ethylphenyl)-5-mercaptotriazole; 3-(2,4-dihydroxyphenyl)-4-(2,6-diisopropylphenyl)-5-mercaptotriazole; 3-(2,4-dihydroxyphenyl)-4-(1-ethyl-indol-4-yl)-5-mercaptotriazole; and 3-(2,4-dihydroxyphenyl)-4-(2,3-dihydro-benzo[1,4]dioxin-5-yl)-5-mercaptotriazole.

The use of inhibitors of a JAK kinase or PDK kinase is described in U.S. Pat. No. 8,183,245 to Guerin et al., incorporated herein by this reference. JAK kinases include JAK1, JAK2, JAK3, and TYK2. Suitable inhibitors of these classes of kinases include, but are not limited to, 5-(1-methyl-1H-pyrazol-4-yl)-3-(6-piperazin-1-ylpyrazin-2-yl)-1H-pyrrolo[2,3-b]pyridine; 5-(1-methyl-1H-pyrazol-4-yl)-3-[6-(piperidin-4-yloxy)pyrazin-2-yl]-1H-pyrrolo[2,3-b]pyridine; 3-[6-(cyclohexyloxy)pyrazin-2-yl]-5-(1-methyl-1H-pyrazol-4-yl)-1H-pyrrolo[2,3-b]pyridine; N-methyl-6-[5-(1-methyl-1H-pyrazol-4-yl)-1H-pyrrolo[2,3-b]pyridin-3-yl]-N-piperidin-4-ylpyrazin-2-amine; 3-[6-(piperidin-4-yloxy)pyrazin-2-yl]-5-(1H-pyrazol-4-yl)-1H-pyrrolo[2,3-b]pyridine; 3-{6-[(3R)-piperidin-3-yloxy]pyrazin-2-yl}-5-(1H-pyrazol-4-yl)-1H-pyrrolo[2,3-b]pyridine; and 3-{6-[(3S)-piperidin-3-yloxy]pyrazin-2-yl}-5-(1H-pyrazol-4-yl)-1H-pyrrolo[2,3-b]pyridine.

The use of inhibitors of phosphodiesterase type IV (PDE4) is described in U.S. Pat. No. 8,158,672 to Muller et al., incorporated herein by this reference. The inhibitors of PDE4 include fluoroalkoxy-substituted 1,3-dihydroisoindolyl compounds.

The use of inhibitors of c-Met proto-oncogene receptor tyrosine kinase is described in U.S. Pat. No. 8,143,251 to Zhuo et al., incorporated by this reference. These inhibitors include, but are not limited to, triazolotriazines, including [1,2,4]triazolo[4,3-b][1,2,4]triazines. Inhibitors of c-Met proto-oncogene receptor tyrosine kinase are also described in U.S. Pat. No. 8,106,197 to Cui et al., incorporated herein by this reference; these inhibitors include aminoheteroaryl compounds.

The use of inhibitors of indoleamine 2,3-dioxygenase is described in U.S. Pat. No. 8,088,803 to Combs et al., incorporated herein by this reference; these inhibitors include, but are not limited to, 1,2,5-oxadiazole derivatives.

The use of agents that inhibit ATDC (TRIM29) expression is described in U.S. Pat. No. 8,088,749 to Simeone et al., incorporated herein by this reference. These agents include oligonucleotides that function via RNA interference.

The use of proteomimetic inhibitors of the interaction of nuclear receptor with coactivator peptides is described in U.S. Pat. No. 8,084,471 to Hamilton et al., incorporated herein by this reference. These inhibitors include, but are not limited to, 2,3',3''-trisubstituted terphenyls.

The use of antagonists of XIAP family proteins is described in U.S. Pat. No. 7,910,621 to Chen et al., incorporated herein by this reference. These antagonists include, but are not limited to, embelin.

The use of tumor-targeted superantigens is described in U.S. Pat. No. 7,763,253 to Hedlund et al., incorporated herein by this reference.

The use of inhibitors of Pim kinases is described in U.S. Pat. No. 7,750,007 to Bearss et al., incorporated herein by this reference. These inhibitors include, but are not limited to, imidazo[1,2-b]pyridazine and pyrazolo[1,5-a]pyrimidine compounds.

The use of inhibitors of CHK1 or CHK2 kinases is described in U.S. Pat. No. 7,732,436 to Tepe, incorporated herein by this reference. These inhibitors include, but are not limited to, indoloazepines and acid amine salts thereof.

The use of inhibitors of angiopoietin-like 4 protein is described in U.S. Pat. No. 7,740,846 to Gerber et al., incorporated herein by this reference. These inhibitors include, but are not limited to, antibodies, including monoclonal antibodies.

The use of inhibitors of Smo is described in U.S. Pat. No. 7,691,997 to Balkovec et al., incorporated by this reference. Smo, or Smoothened, is a mediator of signaling by hedgehog proteins. Suitable inhibitors include, but are not limited to, 5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 2-(1,1-difluoroethyl)-5-(4-{4-methyl-5-[2-(trifluoromethyl)phenyl]-4H-1,2,4-triazol-3-yl}bicyclo[2.2.2]oct-1-yl-)-1,3,4-oxadiazole; 2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and 2-(1-fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole.

The use of nicotinic acetylcholine receptor antagonists is disclosed in U.S. Pat. No. 7,652,038 to Cooke et al., incorporated herein by this reference. Nicotinic acetylcholine receptor antagonists include, but are not limited to, mecamylamine, hexamethonium, dihydro-β-erythroidine, d-tubocurarine, pempidine, chlorisondamine, erysodine, trimethaphan camsylate, pentolinium, bungarotoxin, succinylcholine, tetraethylammonium, trimethaphan, chlorisondamine, and trimethidinium.

The use of farnesyl protein transferase inhibitors is described in U.S. Pat. No. 7,557,107 to Zhu et al., incorporated herein by this reference. These farnesyl protein transferase inhibitors include tricyclic compounds.

The use of adenosine A3 receptor antagonists is described in U.S. Pat. No. 6,326,390 to Leung et al., incorporated herein by this reference. These adenosine A3 receptor antagonists include tricyclic non-xanthine antagonists and triazoloquinazolines.

Additional drug combinations can include an alkylating hexitol derivative as described above with at least one agent that suppresses growth or replication of glioma cancer stem cells. Such agents include, but are not limited to: an inhibitor of tailless gene expression or tailless gene activity, as described in U.S. Pat. No. 8,992,923 to Liu et al.; an inhibitor of HDAC1, HDAC7, or phosphorylated HDAC7, as described in U.S. Pat. No. 8,912,156 to Ince et al.; Stat3 inhibitors such as naphtho derivatives, as described in U.S. Pat. No. 8,877,803 to Jiang et al.; a combination of a farnesyl transferase inhibitor and a gamma secretase inhibitor, as described in U.S. Pat. No. 8,853,274 to Wang; inhibitors of electron transport chains or the mitochondrial Krebs cycle as described in U.S. Pat. No. 8,815,844 to Clement et al.; Jak2/STAT3 pathway inhibitors such as caffeic acid derivatives as described in United States Patent Application Publication No. 2015/0094343 by Priebe et al.; inhibitors of the glycine cleavage pathway as described in United States Patent Application Publication No. 2015/0011611 by Kim et al.; and glycosylated ether lipids as described in United States Patent Application Publication No. 2015/0011486 by Arthur et al.

United States Patent Application Publication No. 2010/0069458 by Atadja et al., incorporated herein by this reference discloses the use of the following additional therapeutic agents, which can be used together with an alkylating hexitol derivative as described above:

(1) ACE inhibitors, including, but not limited to, benazepril, enazepril, captopril, enalapril, fosinopril, lisinopril, moexipril, quinapril, ramipril, perindopril and trandolapril;

(2) adenosine kinase inhibitors, including, but not limited to, 5-iodotubericidin;

(3) adrenal cortex antagonists, including, but not limited to, mitotane;

(4) AKT pathway inhibitors (protein kinase B inhibitors) including, but not limited to, deguelin and 1,5-dihydro-5-methyl-1-β-D-ribofuranosyl-1,4,5,6,8-pentaazaacenaphthylen-3-amine;

(5) angiogenesis inhibitors, including, but not limited to, fumagillin, Shikonin, Tranilast, ursolic acid; suramin; thalidomide, lenalidomide; phthalazines, including, but not limited to, 1-(4-chloroanilino)-4-(4-pyridylmethyl)phthalazine, 1-(4-methylanilino)-4-(4-pyridylmethyl)phthalazine, 1-(3-chloroanilino)-4-(4-pyridylmethyl)phthalazine, 1-anilino-4-(4-pyridylmethyl)phthalazine, 1-benzylamino-4-(4-pyridylmethyl)phthalazine, 1-(4-methoxyanilino)-4-(4-pyridylmethyl)phthalazine, 1-(3-benzyloxyanilino)-4-(4-pyridylmethyl)phthalazine, 1-(3-methoxyanilino)-4-(4-pyridylmethyl)phthalazine, 1-(2-methoxyanilino}-4-(4-pyridylmethyl)phthalazine, 1-(4-trifluoromethylanilino)-4-(4-pyridylmethyl)phthalazine, 1-(4-fluoroanilino)-4-(4-pyridylmethyl)phthalazine, 1-(3-hydroxyanilino)-4-(4-pyridylmethyl)phthalazine, 1-(4-hydroxyanilino)-4-(4-pyridylmethyl)phthalazine, 1-(3-aminoanilino)-4-(4-pyridylmethyl)phthalazine, 1-(3,4-dichloroanilino)-4-(4-pyridylmethyl)phthalazine, 1-(4-bromoanilino)-4-(4-pyridylmethyl)phthalazine, 1-(3-chloro-4-methoxyanilino)-4-(4-pyridylmethyl)phthalazine, 1-(4-cyanoanilino)-4-(4-pyridylmethyl)phthalazine, 1-(3-chloro-4-fluoroanilino)-4-(4-pyridylmethyl)phthalazine, 1-(3-methylanilino)-4-(4-pyridylmethyl)phthalazine, and other phthalazines disclosed in PCT Patent Application Publication No. WO 98/035958 by Bold et al., incorporated herein in its entirety by this reference, isoquinolines disclosed in PCT Patent Application Publication No. WO 00/09495 by Altmann et al., incorporated herein in its entirety by this reference, including 1-(3,5-dimethylanilino)-4-(pyridin-4-ylmethyl)-isoquinoline; phthalazines disclosed in PCT Patent Application Publication No. WO 00/59509 by Bold et al., incorporated herein in its entirety by this reference, including E-1-(3-methylanilino)-4-[(2-(pyridin-3-yl)vinyl]phthalazine, Z-1-(3-methylanilino)-4-[(2-(pyridin-3-yl)vinyl]phthalazine, 1-(3-methylanilino)-4-[(2-(pyridin-3-yl)ethyl]phthalazine, 1-(3-methylanilino)-4-[{2-(pyridin-4-yl)vinyl]phthalazine, 1-(4-chloro-3-trifluoromethylanilino)-4-[(2-(pyridin-3-yl)ethyl]phthalazine, 1-(4-chloroanilino)-4-[(2-(pyridin-3-yl)ethyl]phthalazine, 1-(3-chlorobenzylamino)-4-[(2-(pyridin-3-yl)ethyl]phthalazine, 1-(4-chloro-3-trifluoromethylanilino)-4-[3-(pyridin-3-yl)propyl]phthalazine, 1-(4-chloroanilino)-4-[3-(pyridin-3-yl)propyl]phthalazine, 1-(3-chloro-5-trifluoromethylanilino)-4-[3-(pyridin-3-yl)propyl]phthalazine, and 1-(4-tert-butylanilino)-4-[3-(pyridin-3-yl)propyl]phthalazine; and monoclonal antibodies;

(6) angiostatic steroids, including, but not limited to, anecortave, triamcinolone, hydrocortisone, 11α-epihydrocotisol, cortexolone, 17α-hydroxyprogesterone, corticosterone, desoxycorticosterone, testosterone, estrone, and dexamethasone;

(7) anti-androgens, including, but not limited to, nilutamide and bicalutamide;

(8) anti-estrogens, including, but not limited to, toremifene, letrozole, testolactone, anastrozole, bicalutamide, flutamide, exemestane, tamoxifen, fulvestrant, and raloxifene;

(9) anti-hypercalcemia agents, including, but not limited to, gallium (Ill) nitrate hydrate and pamidronate disodium;

(10) apoptosis inducers, including, but not limited to, 2-[[3-(2,3-dichlorophenoxy)propyl]amino]-ethanol, gambogic acid, embellin, and arsenic trioxide;

(11) ATI receptor antagonists, including, but not limited to, valsartan;

(12) aurora kinase inhibitors, including, but not limited to, binucleine 2;

(13) aromatase inhibitors, including, but not limited to: (a) steroids, including, but not limited to, atamestane, exemestane, and formestane; and (b) non-steroids, including, but not limited to, aminoglutethimide, roglethimide, pyridoglutethimide, trilostane, testolactone, ketokonazole, vorozole, fadrozole, anastrozole, and letrozole;

(14) bisphosphonates, including, but not limited to, etidronic acid, clodronic acid, tiludronic acid, alendronic acid, ibandronic acid, risedronic acid, and zoledronic acid;

(15) Bruton's tyrosine kinase inhibitors, including, but not limited to, terreic acid;

(16) calcineurin inhibitors, including, but not limited to, cypermethrin, deltamethrin, fenvalerate, and tyrphostin 8;

(17) CaM kinase II inhibitors, including, but not limited to, the 5-isoquinolinesulfonic acid 4-[(2S)-2-[(5-isoquinolinylsulfonyl)methylamino]-3-oxo-3-(4-phenyl-1-piperazinyl)propyl]phenyl ester, and N-[2-[[[3-(4-chlorophenyl)-2- propenyl]methyl]amino]methyl]phenyl]-N-(2-hydroxyethyl)-4-methoxy-benzenesulfonamide;

(18) CD45 tyrosine phosphatase inhibitors, including, but not limited to, [[2-(4-bromophenoxy)-5-nitrophenyl]hydroxymethyl]-phosphonic acid;

(19) CDC25 phosphatase inhibitors, including, but not limited to, 2,3-bis[(2-hydroyethyl)thio]-1,4-naphthalenedione;

(20) CHK kinase inhibitors, including, but not limited to, debromohymenialdisine;

(21) compounds targeting/decreasing a protein or lipid kinase activity; or a protein or lipid phosphatase activity; or further anti-angiogenic compounds, including, but not limited to, protein tyrosine kinase and/or serine and/or threonine kinase inhibitors or lipid kinase inhibitors, including, but not limited to:
  (a) compounds targeting, decreasing or inhibiting the activity of the vascular endothelial growth factor receptors (VEGFR) or of vascular endothelial growth factor (VEGF), including, but not limited to, 7H-pyrrolo[2,3-d]pyrimidine derivatives, including: [6-[4-(4-ethyl-piperazine-1-ylmethyl)-phenyl]-7H-pyrrolo[2,3-d]pyrimidinpyrimidin-4-yl]-(R)-1-phenyl-ethyl)-amine (known as AEE788), BAY 43-9006; and isoquinoline compounds disclosed in PCT Patent Application Publication No. WO 00/09495, such as (4-tert-butyl-phenyl)-94-pyridin-4-ylmethyl-isoquinolin-1-yl)-amine;
  (b) compounds targeting, decreasing or inhibiting the activity of the platelet-derived growth factor-receptor (PDGFR), including, but not limited to: N-phenyl-2-pyrimidine-amine derivatives, e.g., imatinib, SU101, SU6668 and GFB-111;
  (c) compounds targeting, decreasing or inhibiting the activity of the fibroblast growth factor-receptor (FGFR);
  (d) compounds targeting, decreasing or inhibiting the activity of the insulin-like growth factor receptor 1 (IGF-1R), including, but not limited to: the compounds disclosed in WO 02/092599 and derivatives thereof of 4-amino-5-phenyl-7-cyclobutyl-pyrrolo[2,3-d]pyrimidine derivatives;
  (e) compounds targeting, decreasing or inhibiting the activity of the Trk receptor tyrosine kinase family;
  (f) compounds targeting, decreasing or inhibiting the activity of the Axl receptor tyrosine kinase family;
  (g) compounds targeting, decreasing or inhibiting the activity of the c-Met receptor;
  (h) compounds targeting, decreasing or inhibiting the activity of the Ret receptor tyrosine kinase;
  (i) compounds targeting, decreasing or inhibiting the activity of the Kit/SCFR receptor tyrosine kinase;
  (j) compounds targeting, decreasing or inhibiting the activity of the
  C-kit receptor tyrosine kinases, including, but not limited to, imatinib; (k) compounds targeting, decreasing or inhibiting the activity of members of the c-Abl family and their gene-fusion products, e.g., BCR-Abl kinase, such as N-phenyl-2-pyrimidine-amine derivatives, including, but not limited to: imatinib, 6-(2,6-dichlorophenyl)-2-[(4-fluoro-3-methyl phenyl)amino]-8-methyl-pyrido[2,3-d]pyrimidin-7(8H)-one (PD180970), methyl-4-[N-(2',5'-dihydroxybenzyl)amino]benzoate (Tyrphostin AG957), 4-[[(2,5-dihydroxyphenyl) methyl]amino]benzoic acid tricyclo[3.3.1.13,7]dec-1-yl ester (adaphostin or NSC 680410), 6-(2,6-dichlorophenyl)-8-methyl-2-(3-methylsulfanylanilino)pyrido[2,3-d]pyrimidin-7-one (PD173955), and desatinib;
  (l) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, such as, but not limited to, midostaurin; examples of further compounds include, e.g., UCN-01; safingol, sorafenib, Bryostatin 1; Perifosine; Ilmofosine; 3-[3-[2,5-Dihydro-4-(1-methyl-1H-indol-3-yl)-2,5-dioxo-1H-pyrrol-3-yl]-1H-indol-1-yl]propyl carbamimidothioic acid ester (RO 318220), 3-[(8S)-8-[(dimethylamino)methyl]-6,7,8,9-tetrahydropyrido[1,2-a]indol-10-yl]-4-(1-methyl-1H-indol-3-yl)-1H-pyrrole-2,5-dione (RO 320432), 12-(2-cyanoethyl)-6,7,12,13-tetrahydro-13-methyl-5-oxo-5H-indolo[2,3-a]pyrrolo[3,4-c]carbazole (GO 6976); Isis 3521; (S)-13-[(dimethylamino)methyl]-10,11,14,15-tetrahydro-4,9:16, 21-dimetheno-1H, 13H-dibenzo[e,k]pyrrolo[3,4-h][1,4,13]oxadiazacyclohexadecene-1,3(2H)-dione (LY333531), LY379196; isoquinoline compounds, such as those disclosed in PCT Patent Application Publication No. WO 00/09495; farnesyltransferase inhibitors, including, but not limited to, tipifarnib and lonafarnib; 2-(2-chloro-4-iodo-phenylamino)-N-cyclopropylmethoxy-3,4-difluoro-benzamide (PD184352); and QAN697, a PI3K inhibitor;
  (m) compounds targeting, decreasing or inhibiting the activity of protein-tyrosine kinase, such as, but not limited to, imatinib mesylate, a tyrphostin, pyrymidylaminobenzamide and derivatives thereof; a tyrphostin is preferably a low molecular weight ($M_r$<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, Tyrphostin AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; Tyrphostin AG957, and adaphostin (4-{[(2,5-dihydroxyphenyl)methyl]amino}-benzoic acid adamantyl ester or NSC 680410);
  (n) compounds targeting, decreasing or inhibiting the activity of the epidermal growth factor family of receptor tyrosine kinases (EGFR, ErbB2, ErbB3, ErbB4 as homodimers or heterodimers), such as, but not limited to, those compounds, proteins or monoclonal antibodies generically and specifically disclosed in PCT Patent Application Publication No. WO 97/02266 by Traxler et al. such as (R)-6-(4-hydroxyphenyl)-4-[(1-phenyl-ethyl)-amino]-7H-pyrrolo-[2,3-d]pyrimidine, or in European Patent Application Publication No. EP 0564409 by Zimmermann, PCT Patent Application Publication No. WO 99/03854 by Zimmermann et al., European Patent Application Publication No. EP 0520722 by Barker et al., European Patent Application Publication No. EP 0566226 by Barker et al., European Patent Application Publication EP 0787722 by Wissner et al., European Patent Application Publication EP 0837063 by Arnold et al., U.S. Pat. No. 5,747,498 by Schnur et al., PCT Patent Application Publication WO 98/10767 by McMahon et al., PCT Patent Application Publication WO 97/30034 by Barker, PCT Patent Application Publication WO 97/49688 by Schnur, PCT Patent Application Publication WO 97/38983 by Bridges et al., PCT Patent Application Publication WO 96/30347 by Schnur et al., including, but not limited to, N-(3-ethylnylphenyl)-6,7-bis(2-methoxyethoxy)-4-quinazolinamine (CP 358774 or erlotinib), PCT Patent Application Publication WO 96/33980 by Gibson et al., including, but not limited to, N-(3-chloro-4-fluorophenyl)-7-methoxy-6-(3-morpholin-4-ylpropoxy)quinazolin-4-amine (gefitinib); and PCT Patent Application Publication WO 95/03283 by Barker et al., including, but not limited to, compound 6-amino-4-(3-methylphenyl-amino)-quinazoline (ZM105180); monoclonal antibodies, including, but not limited to trastuzumab and cetuximab; and other small molecule inhibitors, including, but not limited to: canertinib, pelitinib, lapatinib, and 7H-pyrrolo-[2,3-d]pyrimidine derivatives which are disclosed in PCT Patent Application Publication WO 03/013541 by Bold et al.;

(22) compounds which target, decrease or inhibit the activity of a protein or lipid phosphatase, including, but not limited to, inhibitors of phosphatase 1, phosphatase 2A, PTEN or CDC25, such as, but not limited to okadaic acid or a derivative thereof;

(23) compounds which induce cell differentiation processes, including, but not limited to, retinoic acid, α-tocopherol, γ-tocopherol, δ-tocopherol, α-tocotrienol, γ-tocotrienol, and δ-tocotrienol;

(24) cRAF kinase inhibitors, including, but not limited to, 3-(3,5-dibromo-4-hydroxybenzylidene)-5-iodo-1,3-dihydroindol-2-one and 3-(dimethylamino)-N-[3-[(4-hydroxybenzoyl)amino]-4-methylphenyl]-benzamide;

(25) cyclin dependent kinase inhibitors, including, but not limited to, N9-isopropyl-olomoucine; olomoucine; purvalanol B, roascovitine, kenpaullone, and purvalanol A;

(26) cysteine protease inhibitors, including, but not limited to, N-[(1S)-3-fluoro-2-oxo-1-(2-phenyl]ethyl)propyl]amino]-2-oxo-1-(phenyl methyl)ethyl]-4-morpholinecarboxamide;

(27) DNA intercalators, including, but not limited to, plicamycin and dactinomycin;

(28) DNA strand breakers, including, but not limited to, bleomycin;

(29) E3 ligase inhibitors, including, but not limited to, N-((3,3,3-trifluoro-2-trifluoromethyl)propionyl)sulfanilamide;

(30) EDG binders, including, but not limited to, FTY720;

(31) endocrine hormones, including, but not limited to, leuprolide and megestrol acetate;

(32) farnesyltransferase inhibitors, including, but not limited to, α-hydroxyfarnesylphosphonic acid, 2-[[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-1-methylethyl butanoic acid ester (2S), and manumycin A;

(33) Flk-1 kinase inhibitors, including, but not limited to, 2-cyano-3-[4-hydroxy-3,5-bis(1-methylethyl)phenyl]-N-(3-phenylpropyl)-(2-E)-2-propenamide;

(34) Flt-3 inhibitors, including, but not limited to, N-benzoyl-staurosporine, midostaurin, and N-(2-diethylaminoethyl)-5-[(Z)-(5-fluoro-2-oxo-1H-indol-3-ylidene)methyl]-2,4-dimethyl-1H-pyrrole-3-carboxamide (sunitinib);

(35) gonadorelin agonists, including, but not limited to, abarelix, goserelin, and goserelin acetate;

(36) heparanase inhibitors, including, but not limited to, phosphomannopentaose sulfate (PI-88);

(37) histone deacetylase (HDAC) inhibitors, including, but not limited to, compounds disclosed in PCT Patent Application Publication No. WO 02/22577 by Bair et al., including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-aminophenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate;

(38) HSP90 inhibitors, including, but not limited to: 17-allylamino,17-demethoxygeldanamycin (17AAG); a geldanamycin derivative; other geldanamycin-related compounds; radicicol; and 5-(2,4-dihydroxy-5-isopropyl-phenyl)-4-(4-morpholin-4-ylmethyl-phenyl)-isoxazole-3-carboxylic acid ethylamide;

(39) IκBα inhibitors (IKKs), including, but not limited to, 3-[(4-methylphenyl)sulfonyl]-(2E)-2-propenenitrile;

(40) insulin receptor tyrosine kinase inhibitors, including, but not limited to, hydroxy-2-naphthalenylmethylphosphonic acid;

(41) c-Jun N-terminal kinase inhibitors, including, but not limited to, pyrazoleanthrone and epigallocatechin gallate;

(42) microtubule binding agents, including, but not limited to: vinblastine sulfate; vincristine sulfate; vindesine; vinorelbine; docetaxel; paclitaxel; discodermolides; colchicines; and epothilones and derivatives thereof, such as epothilone B or a derivative thereof;

(43) mitogen-activated protein (MAP) kinase inhibitors, including, but not limited to, N-[2-[[[3-(4-chlorophenyl)-2-propenyl]methyl]amino]methyl]phenyl]-N-(2-hydroxyethyl)-4-methoxy-benzenesulfonamide;

(44) MDM2 inhibitors, including, but not limited to, trans-4-iodo,4'-boranyl-chalcone;

(45) MEK inhibitors, including, but not limited to, bis[amino[2-aminophenyl)thio]methylene]-butanedinitrile;

(46) methionine aminopeptidase inhibitors, including, but not limited to, bengamide and derivatives thereof;

(47) MMP inhibitors, including, but not limited to: actinonin; epigallocatechin gallate; collagen peptidomimetic and non-peptidomimetic inhibitors; tetracycline derivatives such as hydroxamate, batimastat, marimastat, primomastat, TAA211, N-hydroxy-2(R)-[[(4-methoxyphenyl)sulfonyl](3-picolyl)amino]-3-methylbutanamide hydrochloride (MMI270B), and AAJ996;

(48) NGFR tyrosine kinase inhibitors, including, but not limited to, Tyrphostin AG 879;

(49) p38 MAP kinase inhibitors, including, but not limited to, 3-(dimethylamino)-N-[3-[(4-hydroxybenzoyl)amino]-4-methylphenyl]-benzamide;

(50) p56 tyrosine kinase inhibitors, including, but not limited to, 9,10-dihydro-3-hydroxy-1-methoxy-9,10-dioxo-2-anthracenecarboxaldehyde and Tyrphostin 46;

(51) PDGFR tyrosine kinase inhibitors, including, but not limited to, Tyrphostin AG 1296; Tyrphostin 9, 2-amino-4-(1H-indol-5-yl)-1,3-butadiene-1,1,3-tricarbonitrile, and imatinib;

(52) phosphatidylinositol 3-kinase inhibitors, including, but not limited to, wortmannin and quercetin dihydrate;

(53) phosphatase inhibitors, including, but not limited to, cantharidic acid, cantharidin, and (E)-N-[4-(2-carboxyethenyl)benzoyl]glycyl-L-α-glutamyl-L-leucinamide;

(54) platinum agents, including, but not limited to, carboplatin, cisplatin, oxaliplatin, satraplatin, and ZD0473;

(55) protein phosphatase inhibitors, including, but not limited to:
- (a) PP1 and PP2A inhibitors, including, but not limited to, cantharidic acid and cantharidin;
- (b) tyrosine phosphatase inhibitors, including, but not limited to, L-P-bromotetramisole oxalate, benzylphosphonic acid, and (5R)-4-hydroxy-5-(hydroxymethyl)-3-(1-oxohexadecyl)-2(5H)-furanone;

(56) PKC inhibitors, including, but not limited to, -[1-[3-(dimethylamino)propyl]-1H-indol-3-yl]-4-(1H-indol-3-yl)-1H-pyrrolo-2,5-dione, sphingosine, staurosporine, Tyrphostin 51, and hypericin;

(57) PKC delta kinase inhibitors, including, but not limited to, rottlerin;

(58) polyamine synthesis inhibitors, including, but not limited to, (RS)-2,5-diamino-2-(difluoromethyl)pentanoic acid (DMFO);

(59) proteasome inhibitors, including, but not limited to, aclacinomycin A, gliotoxin, and bortezomib;

(60) PTP1B inhibitors, including, but not limited to, (E)-N-[4-(2-carboxyethenyl)benzoyl]glycyl-L-α-glutamyl-L-leucinamide;

(61) protein tyrosine kinase inhibitors, including, but not limited to: Tyrphostin AG 126; Tyrphostin AG 1288; Tyrphostin AG 1295; geldanamycin; and genistein;

(62) SRC family tyrosine kinase inhibitors, including, but not limited to, 1-(1,1-dimethylethyl)-3-(1-naphthalenyl)-1H-pyrazolo[3,4-d]pyrimidin-4-amine, and 3-(4-chlorophenyl)-1-(1,1-dimethylethyl)-1H-pyrazolo[3,4-d]pyrimidin-4-amine;

(63) Syk tyrosine kinase inhibitors including, but not limited to, piceatannol;

(64) Janus (JAK-2 and/or JAK-3) tyrosine kinase inhibitors, including, but not limited to, Tyrphostin AG 490, and 2-naphthyl vinyl ketone;

(65) inhibitors of Ras oncogenic isoforms, including, but not limited to, (2S)-2-[[(2S)-2-[(2S,3S)-2-[(2R)-2-amino-3-mercaptopropyl]amino]-3-methylpentyl]oxy]-1-oxo-3-phenylpropyl]amino]-4-(methylsulfonyl)-butanoic acid 1-methylethyl ester (L-744832), DK8G557, and tipifarnib;

(66) retinoids, including, but not limited to, isotretinoin and tretinoin;

(67) ribonucleotide reductase inhibitors, including, but not limited to, hydroxyurea and 2-hydroxy-1H-isoindole-1,3-dione;

(68) RNA polymerase II elongation inhibitors, including, but not limited to, 5,6-dichloro-1-beta-D-ribofuranosylbenzimidazole;

(69) S-adenosylmethionine decarboxylase inhibitors, including, but not limited to, 5-amidino-1-tetralone-2'-amidinohydrazone and other compounds disclosed in U.S. Pat. No. 5,461,076 to Stanek et al., incorporated herein by this reference;

(70) serine/threonine kinase inhibitors, including, but not limited to, sorafenib and 2-aminopurine;

(71) compounds which target, decrease, or inhibit the activity or function of serine/threonine mTOR kinase, including, but not limited to, everolimus, temsirolimus, zotarolimus, rapamycin, derivatives and analogs of rapamycin, deforolimus, AP23841, sirolimus, and everolimus;

(72) somatostatin receptor antagonists, including, but not limited to, octreotide and pasireotide (SOM230);

(73) sterol biosynthesis inhibitors, including, but not limited to, terbinadine;

(74) telomerase inhibitors, including, but not limited to, telomestatin; and

(75) topoisomerase inhibitors, including, but not limited to:
- (a) topoisomerase I inhibitors, including, but not limited to, topotecan, gimatecan, irinotecan, camptothecin and its analogues, 9-nitrocamptothecin and the macromolecular camptothecin conjugate PNU-16614, macromolecular camptothecin conjugates described in PCT Patent Application Publication No. WO 99/17804 by Angelucci et al., 10-hydroxycamptothecin acetate salt, etoposide idarubicin hydrochloride, teniposide, doxorubicin; epirubicin hydrochloride, mitoxantrone hydrochloride, and daunorubicin hydrochloride; and
- (b) topoisomerase II inhibitors, including, but not limited to, anthracyclines, such as doxorubicin, including liposomal formulations thereof, daunorubicin, including liposomal formulations thereof, epirubicin, idarubicin, nemorubicin, mitoxantrone, losoxantrone, etoposide, and eniposide;

(76) VEGFR tyrosine kinase inhibitors, including, but not limited to, 3-(4-dimethylaminobenzylidenyl)-2-indolinone; and

(77) RANKL inhibitors, including, but not limited to, denosumab.

When the improvement is made by chemosensitization, the chemosensitization can comprise, but is not limited to, the use of an alkylating hexitol derivative as a chemosensitizer in combination with an agent selected from the group consisting of:
- (a) topoisomerase inhibitors;
- (b) fraudulent nucleosides;
- (c) fraudulent nucleotides;
- (d) thymidylate synthetase inhibitors;
- (e) signal transduction inhibitors;
- (f) cisplatin or platinum analogs;
- (g) alkylating agents;
- (h) anti-tubulin agents;
- (i) antimetabolites;
- (j) berberine;
- (k) apigenin;
- (l) colchicine or an analog of colchicine;
- (m) genistein;
- (n) etoposide;
- (o) cytarabine;
- (p) camptothecin;
- (q) vinca alkaloids;
- (r) 5-fluorouracil;
- (s) curcumin;
- (t) NF-κB inhibitors;
- (u) rosmarinic acid; and
- (v) mitoguazone.

When the improvement is made by chemopotentiation, the chemopotentiation can comprise, but is not limited to, the use of an alkylating hexitol derivative as a chemopotentiator in combination with an agent selected from the group consisting of:
- (a) fraudulent nucleosides;
- (b) fraudulent nucleotides;
- (c) thymidylate synthetase inhibitors;
- (d) signal transduction inhibitors;
- (e) cisplatin or platinum analogs;
- (f) alkylating agents;
- (g) anti-tubulin agents;
- (h) antimetabolites;
- (i) berberine;
- (j) apigenin;

(k) colchicine or analogs of colchicine;
(l) genistein;
(m) etoposide;
(n) cytarabine;
(o) camptothecins;
(p) vinca alkaloids;
(q) topoisomerase inhibitors;
(r) 5-fluorouracil;
(s) curcumin;
(t) NF-κB inhibitors;
(u) rosmarinic acid;
(v) mitoguazone; and
(w) a biotherapeutic.

In one alternative, when the chemopotentiation involves chemopotentiation of an alkylating agent by the activity of an alkylating hexitol derivative, the alkylating agent can be selected from the group consisting of BCNU, BCNU wafers (Gliadel), CCNU, bendamustine (Treanda), lomustine, ACNU, and temozolimide (Temodar).

When the agent subject to chemopotentiation is a biotherapeutic, the biotherapeutic can be, but is not limited to, a biotherapeutic selected from the group consisting of Avastin, Herceptin, Rituxan, and Erbitux.

When the improvement is made by post-treatment management, the post-treatment management can be, but is not limited to, a method selected from the group consisting of:
  (a) a therapy associated with pain management;
  (b) nutritional support;
  (c) administration of an anti-emetic;
  (d) an anti-nausea therapy;
  (e) administration of an anti-inflammatory agent;
  (f) administration of an anti-pyretic agent; and
  (g) administration of an immune stimulant.

When the improvement is made by alternative medicine/post-treatment support, the alternative medicine/post-treatment support can be, but is not limited to, a method selected from the group consisting of:
  (a) hypnosis;
  (b) acupuncture;
  (c) meditation;
  (d) a herbal medication created either synthetically or through extraction; and
  (e) applied kinesiology.

In one alternative, when the method is a herbal medication created either synthetically or through extraction, the herbal medication created either synthetically or through extraction can be selected from the group consisting of:
  (a) a NF-κB inhibitor;
  (b) a natural anti-inflammatory;
  (c) an immunostimulant;
  (d) an antimicrobial; and
  (e) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an anti-microbial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product improvement can be, but is not limited to, a bulk drug product improvement selected from the group consisting of:
  (a) salt formation;
  (b) preparation as a homogeneous crystal structure;
  (c) preparation as a pure isomer;
  (d) increased purity;
  (e) preparation with lower residual solvent content; and
  (f) preparation with lower residual heavy metal content.

When the improvement is made by use of a diluent, the diluent can be, but is not limited to, a diluent selected from the group consisting of:
  (a) an emulsion;
  (b) dimethylsulfoxide (DMSO);
  (c) N-methylformamide (NMF);
  (d) dimethylformamide (DMF)
  (e) dimethylacetamide (DMA);
  (f) ethanol;
  (g) benzyl alcohol;
  (h) dextrose-containing water for injection;
  (i) Cremophor;
  (j) cyclodextrin; and
  (k) PEG.

When the improvement is made by use of a solvent system, the solvent system can be, but is not limited to, a solvent system selected from the group consisting of:
  (a) an emulsion;
  (b) DMSO;
  (c) NMF;
  (d) DMF;
  (e) DMA;
  (f) ethanol;
  (g) benzyl alcohol;
  (h) dextrose-containing water for injection;
  (i) Cremophor;
  (j) PEG; and
  (k) salt systems.

When the improvement is made by use of an excipient, the excipient can be, but is not limited to, an excipient selected from the group consisting of:
  (a) mannitol;
  (b) albumin;
  (c) EDTA;
  (d) sodium bisulfite;
  (e) benzyl alcohol;
  (f) carbonate buffers;
  (g) phosphate buffers;
  (h) PEG;
  (i) vitamin A;
  (j) vitamin D;
  (k) vitamin E;
  (l) esterase inhibitors;
  (m) cytochrome P450 inhibitors;
  (n) multi-drug resistance (MDR) inhibitors;
  (o) organic resins;
  (p) detergents;
  (q) perillyl alcohol or an analog thereof; and
  (r) activators of channel-forming receptors.

Suitable esterase inhibitors include, but are not limited to, ebelactone A and ebelactone B.

Suitable cytochrome P450 inhibitors include, but are not limited to, 1-aminobenzotriazole, N-hydroxy-N'-(4-butyl-2-methylphenyl)formamidine, ketoconazole, methoxsalen, metyrapone, roquefortine C, proadifen, 2,3',4,5'-tetramethylstilbene, and troleandomycin.

Suitable MDR inhibitors include, but are not limited to, 5'-methoxyhydnocarpin, INF 240, INF 271, INF 277, INF 392, INF 55, reserpine, and GG918. MDR inhibitors are described in M. Zloh & S. Gibbons, "Molecular Similarity of MDR9 Inhibitors," *Int. J. Mol. Sci.* 5: 37-47 (2004), incorporated herein by this reference.

Suitable organic resins include, but are not limited to, a partially neutralized polyacrylic acid, as described in U.S. Pat. No. 8,158,616 to Rodgers et al., incorporated herein by this reference.

Suitable detergents include, but are not limited to, non-ionic detergents such as a polysorbate or a poloxamer, and are described in PCT Patent Application Publication No. WO/1997/039768 by Bjorn et al., incorporated herein by this reference.

The use of perillyl alcohol or an analog thereof to improve transport of anti-neoplastic agents is described in United States Patent Application 2012/0219541 by Chen et al., incorporated herein by this reference.

The use of activators of channel-forming receptors is described in United States Patent Application Publication No. 2010/0311678 by Bean et al., incorporated herein by this reference. Such activators of channel-forming receptors include, but are not limited to, capsaicin, lidocaine, eugenol, arvanil (N-arachidonoylvanillamine), anandamide, 2-aminoethoxydiphenyl borate, resiniferatoxin, phorbol 12-phenylacetate 13-acetate 20-homovanillate (PPAHV), olvanil, N-oleoyldopamine, N-arachidonyldopamine, 6'-iodoresiniferatoxin (6'-IRTX), $C_{18}$ N-acylethanolamines, lipoxygenase derivatives such as 12-hydroperoxyeicosatetraenoic acid, inhibitor cysteine knot (ICK) peptides (vanillotoxins), piperine, N-[2-(3,4-dimethylbenzyl)-3-(pivaloyloxy)propyl]-2-[4-(2-aminoethoxy)-3-methoxyphenyl]acetamide, N-[2-(3,4-dimethylbenzyl)-3-(pivaloyloxy)propyl]-N'-(4-hydroxy-3-methoxybenzyl)thiourea, SU200 N-(4-t-butylbenzyl)-N'-(4-hydroxy-3-methoxybenzyl)thiourea), transacin, cinnamaldehyde, allyl-isothiocyanate, diallyl disulfide, icilin, cinnamon oil, wintergreen oil, clove oil, acrolein, mustard oil, ATP, 2-methylthio-ATP, 2' and 3'-O-(4-benzoylbenzoyl)-ATP, ATP-5'-O-(3-thiotriphosphate), menthol, eucalyptol, linalool, geraniol, and hydroxycitronellal.

When the improvement is made by use of a dosage form, the dosage form can be, but is not limited to, a dosage form selected from the group consisting of:
(a) tablets;
(b) capsules;
(c) topical gels;
(d) topical creams;
(e) patches;
(f) suppositories;
(g) lyophilized dosage fills;
(h) immediate-release formulations;
(i) slow-release formulations;
(j) controlled-release formulations; and
(k) liquid in capsules.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dibromodulcitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

Immediate-release formulations are described in U.S. Pat. No. 8,148,393 to van Dalen et al., incorporated herein by this reference. Immediate-release formulations can include, for example, conventional film-coated tablets.

Slow-release formulations are described in U.S. Pat. No. 8,178,125 to Wen et al., incorporated herein by this reference. Slow-release formulations can include, for example, microemulsions or liquid crystals.

Controlled-release formulations are described in U.S. Pat. No. 8,231,898 to Oshlack et al., incorporated herein by this reference. Controlled-release formulations can include, for example, a matrix that includes a controlled-release material. Such a controlled-release material can include hydrophilic and/or hydrophobic materials, such as gums, cellulose ethers, acrylic resins, protein derived materials, waxes, shellac, and oils such as hydrogenated castor oil or hydrogenated vegetable oil. However, any pharmaceutically acceptable hydrophobic or hydrophilic controlled-release material which is capable of imparting controlled-release of the mustard-based alkylating agent may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polymethacrylate, polyacrylamide, poly (methacrylic acid anhydride), and glycidyl methacrylate copolymers.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:

(a) oral dosage forms;
(b) nanocrystals;
(c) nanoparticles;
(d) cosolvents;
(e) slurries;
(f) syrups;
(g) bioerodible polymers;
(h) liposomes;
(i) slow-release injectable gels;
(j) microspheres; and
(k) targeting compositions with epidermal growth factor receptor-binding peptides.

Nanocrystals are described in U.S. Pat. No. 7,101,576 to Hovey et al., incorporated herein by this reference.

Nanoparticles for drug delivery are described in U.S. Pat. No. 8,258,132 to Bosch et al., incorporated herein by this reference. Typically, such nanoparticles have an average particle size of the active ingredient of less than about 1000 nm, more preferably, less than about 400 nm, and most preferably, less than about 250 nm. The nanoparticles can be coated with a surface stabilizer, such as, but not limited to, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxes 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)), dioctyl sodium sulfosuccinate (DOSS), docusate sodium (Ashland Chem. Co., Columbus, Ohio); Duponol P®, which is a sodium lauryl sulfate (DuPont); Triton X-200®, which is an alkyl aryl polyether sulfonate (Rohm and Haas); Crodestas F-110®, which is a mixture of sucrose stearate and sucrose distearate (Croda Inc.); p-isononylphenoxy-poly-(glycidol), also known as Olin-IOG® or Surfactant 10-G® (Olin Chemicals, Stamford, Conn.); Crodestas SL-40® (Croda, Inc.); and SA9OHCO, which is $C_{18}H_{37}CH_2(CON(CH_3)-OCH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methyl-glucamide; n-heptyl-β-D-glucopyranoside; n-heptyl β-D-thioglucoside; n-hexyl β-D-glucopyranoside; nonanoyl-N-methylglucamide; n-nonanoyl β-D-glucopyranoside; octanoyl-N-methylglucamide; n-octyl β-D-glucopyranoside; and octyl β-D-thioglucopyranoside. Nanoparticles for drug delivery are also described in United States Patent Application Publication No. 2010/209479 by Carroll et al., incorporated herein by this reference. These nanoparticles include carbon nanoparticles such as carbon nanotubes.

Pharmaceutically acceptable cosolvents are described in U.S. Pat. No. 8,207,195 to Navratil et al., incorporated herein by this reference, and include, but are not limited to, water, methanol, ethanol, 1-propanol, isopropanol, 1-butanol, isobutanol, t-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether.

Slurries for use in pharmaceutical formulations are described in United States Patent Application Publication No. 2006/0229277 by Laxminarayan, incorporated herein by this reference.

Syrups for use in pharmaceutical formulations are described in U.S. Pat. No. 8,252,930 to Stoit et al., incorporated herein by this reference. Such syrups can include the active ingredient and a syrup-forming component such as sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutyrate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly (alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference. Liposomes can incorporate short oligopeptide sequences capable of targeting the EGFR receptor, as described in United States Patent Application Publication 2012/0213844 by Huang et al., incorporated herein by this reference. Alternatively, liposomes can include nuclear localization signal/fusogenic peptide conjugates and form targeted liposome complexes, as described in United States Patent Application Publication 2012/0183596 to Boulikas, incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000), incorporated herein by this reference.

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

The use of targeting compositions with epidermal growth factor receptor-binding peptides is described in United States Patent Application Publication No. 2010/0151003 by Trikha et al., incorporated herein by this reference.

When the improvement is made by use of a drug conjugate form, the drug conjugate form can be, but is not limited to, a drug conjugate form selected from the group consisting of:

(a) a polymer system;
(b) polylactides;
(c) polyglycolides;
(d) amino acids;
(e) peptides;
(f) multivalent linkers;
(g) immunoglobulins;
(h) cyclodextrin polymers;
(i) modified transferrin;
(j) hydrophobic or hydrophobic-hydrophilic polymers;
(k) conjugates with a phosphonoformic acid partial ester;
(l) conjugates with a cell-binding agent incorporating a charged cross-linker; and
(m) conjugates with β-glucuronides through a linker.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Conjugates with immunoglobulins are disclosed in U.S. Pat. No. 4,925,662 to Oguchi et al., incorporated herein by this reference. The conjugates are prepared by use of a cross-linking agent such as carbodiimide, glutaraldehyde, or diethyl malonimidate.

Cyclodextrin polymers, their conjugates with therapeutically active agents, and their administration together with particles are described in United States Patent Application Publication Serial No. 2012/0213854 by Fetzer, incorporated herein by this reference.

Conjugates with modified transferrin are described in United States Patent Application Publication Serial No. 2011/0288023 by Kamei et al., incorporated herein by this reference.

Conjugates with hydrophobic or hydrophobic-hydrophilic polymers are described in United States Patent Application Publication No. 2011/0268658 by Crawford et al., incorporated herein by this reference. These polymers can include mono-, di-, or tripeptides. These polymers can also include polylactic acid (PLA), polyglycolic acid (PGA), poly (lactic-co-glycolic) acid (PLGA), polycaprolactone (PCL), polydioxanone (PDO), polyanhydrides, polyorthoesters, or chitosan.

Conjugates with a phosphonoformic acid partial ester are described in United States Patent Application Publication No. 2010/227831 by Saha et al., incorporated herein by this reference.

Conjugates with a cell-binding agent incorporating a charged cross-linker are described in U.S. Pat. No. 8,236,319 to Chari et al., incorporated herein by this reference.

Conjugates with β-glucuronides through a linker are described in U.S. Pat. No. 8,039,273 to Jeffrey, incorporated herein by this reference.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonyldimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a compound analog, the compound analog can be, but is not limited to, a compound analog selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

When the improvement is made by use of a prodrug system, the prodrug system can be, but is not limited to, a prodrug system selected from the group consisting of:
(a) the use of enzyme sensitive esters;
(b) the use of dimers;
(c) the use of Schiff bases;
(d) the use of pyridoxal complexes;
(e) the use of caffeine complexes; and
(f) the use of nitric oxide-releasing prodrugs;
(g) the use of prodrugs with fibroblast activation protein α-cleavable oligopeptides;
(h) the use of prodrugs that are products of reaction with an acetylating or carbamylating agent;
(i) the use of prodrugs that are hexanoate conjugates;
(j) the use of prodrugs that are polymer-agent conjugates; and
(k) the use of prodrugs that are subject to redox activation.

As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound as described herein. Thus, the term "prodrug" refers to a precursor of a biologically active compound that is pharmaceutically acceptable. A prodrug can be inactive when administered to a subject, but is then converted in vivo to an active compound, for example, by hydrolysis (e.g., hydrolysis in blood or a tissue). In certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24), incorporated herein by this reference. A discussion of prodrugs is provided in T. Higuchi et al., "Pro-Drugs as Novel Delivery Systems," *ACS Symposium Series*, Vol. 14 and in E. B. Roche, ed., *Bioreversible Carriers in Drug Design* (American Pharmaceutical Association & Pergamon Press, 1987), both incorporated herein by this reference. Exemplary advantages of a prodrug can include, but are not limited to, its physical properties, such as enhanced water solubility for parenteral administration at physiological pH compared to the parent compound, enhanced absorption from the digestive tract, or enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N($C_1$-

$C_2$)alkylamino($C_2$-$C_3$)alkyl (such as (3-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy)ethyl, 1-methyl-1-(($C_1$-$C_6$)alkanoyloxy)ethyl ($C_1$-$C_6$) alkoxycarbonyloxymethyl, N($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy($C_1$-$C_6$) alkyl, amino($C_1$-$C_4$)alkyl or mono-N or di-N,N($C_1$-$C_6$)alkylaminoalkyl, C(Y$^4$)Y$^5$ wherein Y$^4$ is H or methyl and Y$^5$ is mono-N or di-N,N($C_1$-$C_6$)alkylamino, morpholino, piperidin-1-yl or pyrrolidin-1-yl.

The use of prodrug systems is described in T. Jarvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference. The use of nitric oxide-releasing prodrugs is described in N. Nath et al., "JS-K, a Nitric Oxide-Releasing Prodrug, Modulates β-Catenin/TCF Signaling in Leukemic Jurkat Cells: Evidence of an S-Nitrosylated Mechanism," *Biochem. Pharmacol.* 80: 1641-1649 (2010), incorporated herein by this reference. The use of prodrugs with fibroblast activation protein α-cleavable oligopeptides is described in United States Patent Application Publication No. 2002/0155565 by Garin-Chesa et al., incorporated herein by this reference. The use of prodrugs that are products of reaction with an acetylating or carbamylating agent is described in J. H. Lin & J. Y. H. Lu, "Role of Pharmacokinetics and Metabolism in Drug Discovery and Development," *Pharmacol. Rev.* 4: 403-449 (1997), incorporated herein by this reference. The use of hexanoate conjugates is described in U.S. Pat. No. 8,101,661 to Mickle, incorporated herein by this reference. The use of polymer-agent conjugates is described in R. Satchi et al., "PDEPT: Polymer-Directed Enzyme Prodrug Therapy," *Br. J. Cancer* 85: 1070-1076 (2001), incorporated herein by this reference. The use of prodrugs that are subject to redox activation is described in S. H. van Rijt & P. J. Sadler, "Current Applications and Future Potential for Bioinorganic Chemistry in the Development of Anticancer Drugs," *Drug Discov. Today* 14: 1089-1097 (2009), incorporated herein by this reference.

When the improvement is made by use of a multiple drug system, the multiple drug system can be, but is not limited to, a multiple drug system selected from the group consisting of:

(a) inhibitors of multi-drug resistance;
(b) specific drug resistance inhibitors;
(c) specific inhibitors of selective enzymes;
(d) signal transduction inhibitors;
(e) meisoindigo;
(f) imatinib;
(g) hydroxyurea;
(h) dasatinib;
(i) capecitabine;
(j) nilotinib;
(k) repair inhibition agents; and
(l) topoisomerase inhibitors with non-overlapping side effects.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Selective inhibitors of specific enzymes are described in D. Leung et al., "Discovering Potent and Selective Reversible Inhibitors of Enzymes in Complex Proteomes," *Nature Biotechnol.* 21: 687-691 (2003), incorporated herein by this reference.

Repair inhibition is described in N. M. Martin, "DNA Repair Inhibition and Cancer Therapy," *J. Photochem. Photobiol. B* 63: 162-170 (2001), incorporated herein by this reference.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:

(a) biological response modifiers;
(b) cytokines;
(c) lymphokines;
(d) therapeutic antibodies;
(e) antisense therapies;
(f) gene therapies;
(g) ribozymes; and
(h) RNA interference.

Biological response modifiers are described in T. E. G. K. Murthy et al., "Biological Response Modifiers," *Int. J. Pharmtech Res.* 2: 2152-2160 (2010), incorporated herein by this reference.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against a malignancy resistant to a therapeutic agent or technique selected from the group consisting of:
 (a) biological response modifiers;
 (b) cytokines;
 (c) lymphokines;
 (d) therapeutic antibodies;
 (e) antisense therapies;
 (f) gene therapies;
 (g) ribozymes; and
 (h) RNA interference.

In another alternative, when the improvement is made by use of biotherapeutic resistance modulation, the biotherapeutic resistance modulation can be, but is not limited to, use against a malignancy associated with a mutation in or dysregulation of the AHI1 gene also resistant to a therapeutic agent or technique selected from the group consisting of:
 (a) biological response modifiers;
 (b) cytokines;
 (c) lymphokines;
 (d) therapeutic antibodies;
 (e) antisense therapies;
 (f) gene therapies;
 (g) ribozymes; and
 (h) RNA interference.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:
 (a) use with hypoxic cell sensitizers;
 (b) use with radiation sensitizers/protectors;
 (c) use with photosensitizers;
 (d) use with radiation repair inhibitors;
 (e) use with thiol depleting agents;
 (f) use with vaso-targeted agents;
 (g) use with DNA repair inhibitors;
 (h) use with radioactive seeds;
 (i) use with radionuclides;
 (j) use with radiolabeled antibodies; and
 (k) use with brachytherapy.

An alkylating hexitol derivative can be used in combination with radiation for the treatment of a TKI-resistant malignancy.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiaqnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007).

When the improvement is by use of a novel mechanism of action, the novel mechanism of action can be, but is not limited to, a novel mechanism of action that is a therapeutic interaction with a target or mechanism selected from the group consisting of:
 (a) inhibitors of poly-ADP ribose polymerase;
 (b) agents that affect vasculature;
 (c) agents that promote vasodilation;
 (d) oncogenic targeted agents;
 (e) signal transduction inhibitors;
 (f) agents inducing EGFR inhibition;
 (g) agents inducing Protein Kinase C inhibition;
 (h) agents inducing Phospholipase C downregulation;
 (i) agents including jun downregulation;
 (j) agents modulating expression of histone genes;
 (k) agents modulating expression of VEGF;
 (l) agents modulating expression of ornithine decarboxylase;
 (m) agents modulating expression of jun D;
 (n) agents modulating expression of v-jun;
 (o) agents modulating expression of GPCRs;
 (p) agents modulating expression of protein kinase A;
 (q) agents modulating expression of protein kinases other than protein kinase A;
 (r) agents modulating expression of telomerase;
 (s) agents modulating expression of prostate specific genes; and
 (t) agents modulating expression of histone deacetylase.

Inhibitors of poly ADP-ribose polymerase include veliparib (ABT-888), AGO14699, iniparib (BSI-201), carboplatin, gemcitabine, INO-1001, MK4827, nicotinamide, olaparib, paclitaxel, temozolomide, and topotecan, and are described in E. A. Comen & M. Robson, "Inhibition of Poly(ADP)-Ribose Polymerase as a Therapeutic Strategy for Breast Cancer," *Oncology* 24: 55-62 (2010), incorporated herein by this reference. Agents promoting vasodilation include levosimendan, described in W. G. Toiler et al., "Levosimendan, a New Inotropic and Vasodilator Agent," *Anesthesioloqy* 104: 556-569 (2006), incorporated herein by this reference. EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in H. C. Swannie & S. B. Kaye, "Protein Kinase C Inhibitors,"

Curr. Oncol. Rep. 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," Cancer Res. 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," Oncogene 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," Proc. Natl. Acad. Sci. USA 83: 1495-1498 (1986), incorporated herein by this reference. The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," Surgery 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," Cancer Cell 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," Clin. Cancer Res. 8: 2505-2511 (2002), incorporated herein by this reference. The role of Jun D as a target for therapeutic intervention is described in M. M. Caffarel et al., "JunD Is Involved in the Antiproliferative Effect of Δ⁹-Tetrahydrocannibinol on Human Breast Cancer Cells," Oncogene 27: 5033-5044 (2008), incorporated herein by this reference. The role of v-Jun as a target for therapeutic intervention is described in M. Gao et al., "Differential and Antagonistic Effects of v-Jun and c-Jun," Cancer Res. 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," Eur. J. Cancer 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," Ann. Med. 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," Curr. Opin. Hematol. 9: 322-332 (2002), incorporated herein by this reference.

When the improvement is made by use of selective target cell population therapeutics, the use of selective target cell population therapeutics can be, but is not limited to, a use selected from the group consisting of:
    (a) use against radiation sensitive cells;
    (b) use against radiation resistant cells; and
    (c) use against energy depleted cells.

The improvement can also be made by use of an alkylating combination with ionizing radiation.

When the improvement is made by use with an agent to enhance the activity of an alkylating hexitol derivative, the agent to enhance the activity of the alkylating hexitol derivative can be, but is not limited to, an agent selected from the group consisting of:
    (a) nicotinamide;
    (b) caffeine;
    (c) tetandrine; and
    (d) berberine.

When the improvement is made by use with an agent to counteract myelosuppression, the agent to counteract myelosuppression can be, but is not limited to, a dithiocarbamate. U.S. Pat. No. 5,035,878 to Borch et al., incorporated herein by this reference, discloses dithiocarbamates for treatment of myelosuppression; the dithiocarbamates are compounds of the formula $R^1R^2NCS(S)M$ or $R^1R^2NCSS$—$SC(S)$ $NR^3R^4$, wherein $R^1$, $R^2$, $R^3$, and $R^4$ are the same or different, and $R^1$, $R^2$, $R^3$, and $R^4$ are aliphatic, cycloaliphatic, or heterocycloaliphatic groups that are unsubstituted or substituted by hydroxyl; or wherein one of $R^1$ and $R^2$ and one of $R^3$ and $R^4$ can be hydrogen; or wherein $R^1$, $R^2$, $R^3$, and $R^4$ taken together with the nitrogen atom upon which the pair of R groups is substituted, can be a 5-membered or 6-membered N-heterocyclic ring which is aliphatic or aliphatic interrupted by a ring oxygen or a second ring nitrogen, and M is hydrogen or one equivalent or a pharmaceutically acceptable cation, in which case the rest of the molecule is negatively charged. U.S. Pat. No. 5,294,430 to Borch et al., incorporated herein by this reference, discloses additional dithiocarbamates for treatment of myelosuppression. In general, these are compounds of Formula (D-I):

(D-I)

wherein:
    (i) $R^1$ and $R^2$ are the same or different $C_1$-$C_6$ alkyl groups, $C_3$-$C_6$ cycloalkyl groups, or $C_5$-$C_6$ heterocycloalkyl groups; or
    (ii) one of $R^1$ and $R^2$, but not both, can be H; or
    (iii) $R^1$ and $R^2$ taken together with the nitrogen atom can be a 5-membered or 6-membered N-heterocyclic ring which is aliphatic or aliphatic interrupted by a ring oxygen or a second ring nitrogen; and
    (iv) M is hydrogen or one equivalent of a pharmaceutically acceptable cation, in which case the rest of the molecule is negatively charged; or
    (v) M is a moiety of Formula (D-II):

(D-II)

wherein $R^3$ and $R^4$ are defined in the same manner as $R^1$ and $R^2$. Where the group defined by Formula (D-I) is an anion, the cation can be an ammonium cation or can be derived from a monovalent or divalent metal such as an alkali metal or an alkaline earth metal, such as Na⁺, K⁺, or Zn⁺². In the case of the dithiocarbamic acids, the group defined by Formula (D-I) is linked to an ionizable hydrogen atom; typically, the hydrogen atom will dissociate at a pH above about 5.0. Among dithiocarbamates that can be used are: N-methyl,N-ethyldithiocarbamates, hexamethylenedithiocarbamic acid, sodium di(β-hydroxyethyl)dithiocarbamate, various dipropyl, dibutyl and diamyl dithiocarbamates, sodium N-methyl,N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, α-furfuryl dithiocarbamates and imidazoline dithiocarbamates. Another alternative is a compound where $R^1$ of Formula (D-I) is a hydroxy-substituted or, preferably, a (bis to penta) polyhydroxy-substituted lower alkyl group having up to 6 carbon atoms. For example, $R^1$ can be HO—$CH_2$—CHOH—CHOH—CHOH—CHOH—$CH_2$—. In such compounds, $R^2$ can be H or lower alkyl (unsubstituted or substituted with one or more hydroxyl groups). Steric problems can be minimized when $R^2$ is H, methyl, or ethyl. Accordingly, a particularly preferred compound of this type is an N-methyl-glucamine dithiocarbamate salt, the most preferred cations of these salts being sodium or potassium. Other preferred dithiocarbamates include the alkali or alkaline earth metal salts wherein the anion is di-n-butyldithiocarbamate, di-n-propyldithiocarbamate, pentamethylenedithiocarbamate, or tetramethylene dithiocarbamate.

When the improvement is made by use with an agent that increases the ability of the substituted hexitol to pass through the blood-brain barrier, the agent that increases the ability of the substituted hexitol to pass through the blood-brain barrier can be, but is not limited to:

(a) a chimeric peptide of the structure of Formula (D-III):

$$A-NH\overset{O}{\overset{\|}{C}}(CH_2)S-S-(CH_2)_2\overset{O}{\overset{\|}{C}}HN-B \quad \text{(D-III)}$$

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

A-NH(CH$_2$)$_2$S—S—B (cleavable linkage) (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

A-NH—CH(CH$_2$)$_3$CH=NH—B (non-cleavable linkage) (D-III(b)), wherein the bridge is formed using glutaraldehyde as the bridge reagent;

(b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;

(c) a neutral liposome that is pegylated and incorporates the substituted hexitol derivative, wherein the polyethylene glycol strands are conjugated to at least one transportable peptide or targeting agent;

(d) a humanized murine antibody that binds to the human insulin receptor linked to the substituted hexitol derivative through an avidin-biotin linkage; and (e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

Agents that improve penetration of the blood-brain barrier are disclosed in W. M. Pardridge, "The Blood-Brain Barrier: Bottleneck in Brain Drug Development," *NeuroRx* 2: 3-14 (2005), incorporated herein by this reference.

One class of these agents is disclosed in U.S. Pat. No. 4,801,575 to Pardridge, incorporated herein by this reference, which discloses chimeric peptides for delivery of agents across the blood-brain barrier. These chimeric peptides include peptides of the general structure of Formula (D-IV):

$$A-NH\overset{O}{\overset{\|}{C}}(CH_2)S-S-(CH_2)_2\overset{O}{\overset{\|}{C}}HN-B \quad \text{(D-IV)}$$

wherein:

(i) A is somatostatin, thyrotropin releasing hormone (TRH), vasopressin, alpha interferon, endorphin, muramyl dipeptide or ACTH 4-9 analogue; and (ii) B is insulin, IGF-I, IGF-II, transferrin, cationized (basic) albumin or prolactin. In another alternative, the disulfide conjugating bridge between A and B is replaced with a bridge of Subformula (D-IV(a)):

A-NH(CH$_2$)$_2$S—S—B (cleavable linkage) (D-IV(a));

the bridge of Subformula (D-III(a)) is formed when cysteamine and EDAC are employed as the bridge reagents. In yet another alternative, the disulfide conjugating bridge between A and B is replaced with a bridge of Subformula (D-IV(b)):

A-NH—CH(CH$_2$)$_3$CH=NH—B (non-cleavable linkage) (D-IV(b));

the bridge of Subformula (D-III(b)) is formed when glutaraldehyde is employed as the bridge reagent.

U.S. Pat. No. 6,287,792 to Pardridge et al., incorporated herein by this reference, discloses methods and compositions for delivery of agents across the blood-brain barrier comprising either avidin or an avidin fusion protein bonded to a biotinylated agent to form an avidin-biotin-agent complex. The avidin fusion protein can include the amino acid sequences of proteins such as insulin or transferrin, an anti-receptor monoclonal antibody, a cationized protein, or a lectin.

U.S. Pat. No. 6,372,250 to Pardridge, incorporated herein by this reference, discloses methods and compositions for delivery of agents across the blood-brain barrier employing liposomes. The liposomes are neutral liposomes. The surface of the neutral liposomes is pegylated. The polyethylene glycol strands are conjugated to transportable peptides or other targeting agents. Suitable targeting agents include insulin, transferrin, insulin-like growth factor, or leptin. Alternatively, the surface of the liposome could be conjugated with 2 different transportable peptides, one peptide targeting an endogenous BBB receptor and the other targeting an endogenous BCM (brain cell plasma membrane) peptide. The latter could be specific for particular cells within the brain, such as neurons, glial cells, pericytes, smooth muscle cells, or microglia. Targeting peptides may be endogenous peptide ligands of the receptors, analogues of the endogenous ligand, or peptidomimetic MAbs that bind the same receptor of the endogenous ligand. Transferrin receptor-specific peptidomimetic monoclonal antibodies can be used as transportable peptides. Monoclonal antibodies to the human insulin receptor can be used as transportable peptides. The conjugation agents which are used to conjugate the blood-barrier targeting agents to the surface of the liposome can be any of the well-known polymeric conjugation agents such as sphingomyelin, polyethylene glycol (PEG) or other organic polymers, with PEG preferred. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol. The transportable peptide is linked to the liposome as follows: A transportable peptide such as insulin or an HIRMAb is thiolated and conjugated to a maleimide group on the tip of a small fraction of the PEG strands; or, surface carboxyl groups on a transportable peptide such as transferrin or a TfRMAb are conjugated to a hydrazide (Hz) moiety on the tip of the PEG strand with a carboxyl activator group such as N-methyl-N'-3(dimethylaminopropyl)carbodiimide hydrochloride (EDAC); a transportable peptide is thiolated and conjugated via a disulfide linker to the liposome that has been reacted with N-succinimidyl 3-(2-pyridylthio)propionate (SPDP); or a transportable peptide is conjugated to the surface of the liposome with avidin-biotin technology, e.g., the transportable peptide is mono-biotinylated and is bound to avidin or streptavidin (SA), which is attached to the surface of the PEG strand.

U.S. Pat. No. 7,388,079 to Pardridge et al., incorporated herein by this reference, discloses the use of a humanized murine antibody that binds to the human insulin receptor; the humanized murine antibody can be linked to the agent to be delivered through an avidin-biotin linkage.

U.S. Pat. No. 8,124,095 to Pardridge et al., incorporated herein by this reference, discloses monoclonal antibodies that are capable of binding to an endogenous blood-brain barrier receptor-mediated transport system and are thus capable of serving as a vector for transport of a therapeutic agent across the BBB. The monoclonal antibody can be, for example, an antibody specifically binding the human insulin receptor on the human BBB.

United States Patent Application Publication No. 2005/0085419 by Morrison et al., incorporated herein by this reference, discloses a fusion protein for delivery of a wide variety of agents to a cell via antibody-receptor-mediated endocytosis comprises a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative. Typically, the antigen is a protein. Typically, the protein antigen on the surface of the cell is a receptor such as a transferrin receptor- or an insulin receptor. The invention also includes an antibody construct incorporating the fusion protein that is either a heavy chain or a light chain together with a complementary light chain or heavy chain to form an intact antibody molecule. The therapeutic agent can be a non-protein molecule and can be linked covalently to biotin.

Another aspect of the present invention is a composition to improve the efficacy and/or reduce the side effects of suboptimally administered drug therapy employing a substituted hexitol as described above for the treatment of recurrent malignant glioma such as glioblastoma multiforme or the treatment of progressive secondary brain tumor such as that caused by metastases of breast adenocarcinoma, small-cell lung carcinoma, or melanoma comprising an alternative selected from the group consisting of:

(i) a therapeutically effective quantity of a modified hexitol derivative or a derivative, analog, or prodrug of a hexitol derivative or a modified hexitol derivative, wherein the modified hexitol derivative or the derivative, analog or prodrug of the modified hexitol derivative possesses increased therapeutic efficacy or reduced side effects for treatment of a malignancy selected from the group consisting of recurrent glioma and progressive secondary brain tumor as compared with an unmodified hexitol derivative;

(ii) a composition comprising:
  (a) a therapeutically effective quantity of a hexitol derivative, a modified hexitol derivative, or a derivative, analog, or prodrug of a hexitol derivative or a modified hexitol derivative; and
  (b) at least one additional therapeutic agent, therapeutic agent subject to chemosensitization, therapeutic agent subject to chemopotentiation, diluent, excipient, solvent system, drug delivery system, agent for counteracting myelosuppression, or agent for increasing the ability of the hexitol derivative, the modified hexitol derivative, or the derivative, analog, or prodrug of the hexitol derivative or the modified hexitol derivative to pass through the blood-brain barrier, wherein the composition possesses increased therapeutic efficacy or reduced side effects for treatment of a malignancy selected from the group consisting of recurrent glioma and progressive secondary brain tumor as compared with an unmodified hexitol derivative;

(iii) a therapeutically effective quantity of a hexitol derivative, a modified hexitol derivative, or a derivative, analog, or prodrug of a hexitol derivative or a modified hexitol derivative that is incorporated into a dosage form, wherein a hexitol derivative, a modified hexitol derivative, or a derivative, analog, or prodrug of a hexitol derivative or a modified hexitol derivative incorporated into the dosage form possesses increased therapeutic efficacy or reduced side effects for treatment of a malignancy selected from the group consisting of recurrent glioma and progressive secondary brain tumor as compared with an unmodified hexitol derivative;

(iv) a therapeutically effective quantity of a hexitol derivative, a modified hexitol derivative, or a derivative, analog, or prodrug of an hexitol derivative or a modified hexitol derivative that is incorporated into a dosage kit and packaging, wherein a hexitol derivative, a modified hexitol derivative, or a derivative, analog, or prodrug of a hexitol derivative or a modified hexitol derivative incorporated into the dosage kit and packaging possesses increased therapeutic efficacy or reduced side effects for treatment of a malignancy selected from the group consisting of recurrent glioma and progressive secondary brain tumor as compared with an unmodified hexitol derivative; and (v) a therapeutically effective quantity of a hexitol derivative, a modified hexitol derivative, or a derivative, analog, or prodrug of a hexitol derivative or a modified hexitol derivative that is subjected to a bulk drug product improvement, wherein the hexitol derivative, the modified hexitol derivative, or the derivative, analog, or prodrug of the hexitol derivative or the modified hexitol derivative subject to the bulk drug product improvement possesses increased therapeutic efficacy or reduced side effects for treatment of a malignancy selected from the group consisting of recurrent glioma and progressive secondary brain tumor as compared with an unmodified alkylating hexitol derivative.

As described above, the alkylating hexitol derivative can be, but is not limited to, dianhydrogalactitol, a derivative or analog of dianhydrogalactitol, diacetyldianhydrogalactitol, or a derivative or analog of diacetyldianhydrogalactitol.

In one alternative, the pharmaceutical composition is formulated to exert a cytotoxic effect against cancer stem cells.

In one alternative, the composition comprises a drug combination comprising:

(i) an alkylating hexitol derivative, a modified alkylating hexitol derivative, or a derivative, analog, or prodrug of an alkylating hexitol derivative or a modified alkylating hexitol derivative; and (ii) an additional therapeutic agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone; and
  (s) tetrandrine.

In these alternatives, when the additional therapeutic agent is an alkylating agent, the alkylating agent can be, but is not limited to, an alkylating agent selected from the group consisting of BCNU, BCNU wafers, CCNU, bendamustine (Treanda), and temozolimide (Temodar). In another alternative, the drug composition comprises one or more additional agents that are described above with respect to methods according to the present invention employing drug combinations. In drug combinations according to the present invention, both the alkylating hexitol derivative and the additional agent are present in a therapeutically effective quantity. More than one additional agent can be present in a drug combination according to the present invention, subject to the condition that the at least one additional agent does not interact deleteriously with either the alkylating hexitol derivative present in the composition or other additional agent or agents present in the composition.

In another alternative, the composition comprises:

(i) an alkylating hexitol derivative, a modified alkylating hexitol derivative, or a derivative, analog, or prodrug of an alkylating hexitol derivative or a modified alkylating hexitol derivative; and (ii) a therapeutic agent subject to chemosensitization selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) colchicine or an analog of colchicine;
  (m) genistein;
  (n) etoposide;
  (o) cytarabine;
  (p) camptothecin;
  (q) vinca alkaloids;
  (r) 5-fluorouracil;
  (s) curcumin;
  (t) NF-κB inhibitors;
  (u) rosmarinic acid; and
  (v) mitoguazone;

wherein the alkylating hexitol derivative, a modified alkylating hexitol derivative, or a derivative, analog, or prodrug of an alkylating hexitol derivative or a modified alkylating hexitol derivative acts as a chemosensitizer.

In still another alternative, the composition comprises:

(i) an alkylating hexitol derivative, a modified alkylating hexitol derivative, or a derivative, analog, or prodrug of an alkylating hexitol derivative or a modified alkylating hexitol derivative; and (ii) a therapeutic agent subject to chemopotentiation selected from the group consisting of:
  (a) fraudulent nucleosides;
  (b) fraudulent nucleotides;
  (c) thymidylate synthetase inhibitors;
  (d) signal transduction inhibitors;
  (e) cisplatin or platinum analogs;
  (f) alkylating agents;
  (g) anti-tubulin agents;
  (h) antimetabolites;
  (i) berberine;
  (j) apigenin;
  (k) colchicine or analogs of colchicine;
  (l) genistein;
  (m) etoposide;
  (n) cytarabine;
  (o) camptothecins;
  (p) vinca alkaloids;
  (q) topoisomerase inhibitors;
  (r) 5-fluorouracil;
  (s) curcumin;
  (t) NF-κB inhibitors;
  (u) rosmarinic acid;

(v) mitoguazone; and
(w) a biotherapeutic.
wherein the alkylating hexitol derivative, a modified alkylating hexitol derivative, or a derivative, analog, or prodrug of an alkylating hexitol derivative or a modified alkylating hexitol derivative acts as a chemopotentiator.

In these alternatives, wherein the additional therapeutic agent is a biotherapeutic, the biotherapeutic can be, but is not limited to, a biotherapeutic selected from the group consisting of Avastin, Herceptin, Rituxan, and Erbitux.

In yet another alternative, the alkylating hexitol derivative, a modified alkylating hexitol derivative, or a derivative, analog, or prodrug of an alkylating hexitol derivative or a modified alkylating hexitol derivative is subjected to a bulk drug product improvement, wherein the bulk drug product improvement is selected from the group consisting of:
(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

In still another alternative, the composition comprises an alkylating hexitol derivative, a modified alkylating hexitol derivative, or a derivative, analog, or prodrug of an alkylating hexitol derivative or a modified alkylating hexitol derivative and a diluent, wherein the diluent is selected from the group consisting of:
(a) an emulsion;
(b) dimethylsulfoxide (DMSO);
(c) N-methylformamide (NMF)
(d) dimethylformamide (DMF)
(e) dimethylacetamide (DMA);
(f) ethanol;
(g) benzyl alcohol;
(h) dextrose-containing water for injection;
(i) Cremophor;
(j) cyclodextrins; and
(k) PEG.

In still another alternative, the composition comprises an alkylating hexitol derivative, a modified alkylating hexitol derivative, or a derivative, analog, or prodrug of an alkylating hexitol derivative or a modified alkylating hexitol derivative and a solvent system, wherein the solvent system is selected from the group consisting of:
(a) an emulsion;
(b) DMSO;
(c) NMF;
(d) DMF;
(e) DMA;
(f) ethanol;
(g) benzyl alcohol;
(h) dextrose-containing water for injection;
(i) Cremophor;
(j) PEG; and
(k) salt systems.

In yet another alternative, the composition comprises an alkylating hexitol derivative, a modified alkylating hexitol derivative, or a derivative, analog, or prodrug of an alkylating hexitol derivative or a modified alkylating hexitol derivative and an excipient, wherein the excipient is selected from the group consisting of:
(a) mannitol;
(b) albumin;
(c) EDTA;
(d) sodium bisulfite;
(e) benzyl alcohol;
(f) carbonate buffers;
(g) phosphate buffers;
(h) PEG;
(i) vitamin A;
(j) vitamin D;
(k) vitamin E;
(l) esterase inhibitors;
(m) cytochrome P450 inhibitors;
(n) multi-drug resistance (MDR) inhibitors;
(o) organic resins;
(p) detergents;
(q) perillyl alcohol or an analog thereof; and
(r) activators of channel-forming receptors.

In still another alternative, the alkylating hexitol derivative, modified alkylating hexitol derivative, or derivative, analog, or prodrug of an alkylating hexitol derivative or modified alkylating hexitol derivative is incorporated into a dosage form selected from the group consisting of:
(a) tablets;
(b) capsules;
(c) topical gels;
(d) topical creams;
(e) patches;
(f) suppositories;
(g) lyophilized dosage fills;
(h) immediate-release formulations;
(i) slow-release formulations;
(j) controlled-release formulations; and
(k) liquid in capsules.

In still another alternative, the alkylating hexitol derivative, modified alkylating hexitol derivative, or derivative, analog, or prodrug of an alkylating hexitol derivative or modified alkylating hexitol derivative is incorporated into a dosage kit and packaging selected from the group consisting of amber vials to protect from light and stoppers with specialized coatings to improve shelf-life stability.

In still another alternative, the composition comprises: (i) an alkylating hexitol derivative, modified alkylating hexitol derivative, or derivative, analog, or prodrug of an alkylating hexitol derivative or modified alkylating hexitol derivative; and (ii) a drug delivery system, wherein the drug delivery system is selected from the group consisting of:
(a) oral dosage forms;
(b) nanocrystals;
(c) nanoparticles;
(d) cosolvents;
(e) slurries;
(f) syrups;
(g) bioerodible polymers;
(h) liposomes;
(i) slow-release injectable gels;
(j) microspheres; and
(k) targeting compositions with epidermal growth factor receptor-binding peptides.

In still another alternative of a composition according to the present invention, the therapeutic agent is a modified alkylating hexitol derivative, and the modification is selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

In still another alternative of a composition according to the present invention, the therapeutic agent is an alkylating hexitol derivative, modified alkylating hexitol derivative, or derivative or analog of an alkylating hexitol derivative or modified alkylating hexitol derivative and the therapeutic agent is present in the composition in a drug conjugate form, wherein the drug conjugate form is a drug conjugate form selected from the group consisting of:
(a) a polymer system;
(b) polylactides;
(c) polyglycolides;
(d) amino acids;
(e) peptides;
(f) multivalent linkers;
(g) immunoglobulins;
(h) cyclodextrin polymers;
(i) modified transferrin;
(j) hydrophobic or hydrophobic-hydrophilic polymers;
(k) conjugates with a phosphonoformic acid partial ester;
(l) conjugates with a cell-binding agent incorporating a charged cross-linker; and
(m) conjugates with β-glucuronides through a linker.

In still another alternative of a composition according to the present invention, the therapeutic agent is an alkylating hexitol derivative, modified alkylating hexitol derivative, or derivative or analog of an alkylating hexitol derivative or modified alkylating hexitol derivative and the therapeutic agent is in the form of a prodrug system, wherein the prodrug system is selected from the group consisting of:
(a) enzyme sensitive esters;
(b) dimers;
(c) Schiff bases;
(d) pyridoxal complexes;
(e) caffeine complexes;
(f) nitric oxide-releasing prodrugs;
(g) prodrugs with fibroblast activation protein α-cleavable oligopeptides;
(h) products of reaction with an acylating or carbamylating agent;
(i) hexanoate conjugates;
(j) polymer-agent conjugates; and
(k) prodrugs that are subject to redox activation.

In still another alternative of a composition according to the present invention, the therapeutic agent is an alkylating hexitol derivative, modified alkylating hexitol derivative, or derivative, analog, or prodrug of an alkylating hexitol derivative or modified alkylating hexitol derivative and the composition further comprises at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

In still another alternative of a composition according to the present invention, the therapeutic agent is an alkylating hexitol derivative, modified alkylating hexitol derivative, or derivative, analog, or prodrug of an alkylating hexitol derivative or modified alkylating hexitol derivative and the composition further comprises an agent for counteracting myelosuppression. Typically, the agent that counteracts myelosuppression is a dithiocarbamate.

In still another alternative of a composition according to the present invention, the therapeutic agent is an alkylating hexitol derivative, modified alkylating hexitol derivative, or derivative, analog, or prodrug of an alkylating hexitol derivative or modified alkylating hexitol derivative and the composition further comprises an agent that increases the ability of the substituted hexitol to pass through the blood-brain barrier, wherein the agent that increases the ability of the substituted hexitol to pass through the blood-brain barrier is selected from the group consisting of:
(a) a chimeric peptide of the structure of Formula (D-III):

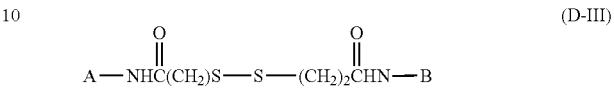

(D-III)

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

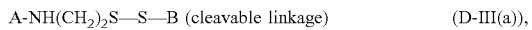

A-NH(CH₂)₂S—S—B (cleavable linkage)          (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

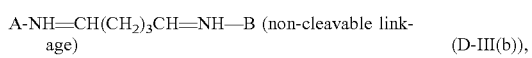

A-NH=CH(CH₂)₃CH=NH—B (non-cleavable linkage)          (D-III(b)), wherein the bridge is formed using glutaraldehyde as the bridge reagent;
(b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;
(c) a neutral liposome that is pegylated and incorporates the substituted hexitol derivative, wherein the polyethylene glycol strands are conjugated to at least one transportable peptide or targeting agent;
(d) a humanized murine antibody that binds to the human insulin receptor linked to the substituted hexitol derivative through an avidin-biotin linkage; and
(e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

In one alternative, when the alkylating hexitol derivative is dianhydrogalactitol, the composition is formulated for administration of dianhydrogalactitol by dosing once daily for three consecutive days every 21 days.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent, such as dianhydrogalactitol or an analog or derivative of dianhydrogalactitol as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg.

In other embodiments, the dose is between about 2000 to about 3000 mg.

Plasma concentrations in the subjects may be between about 100 µM to about 1000 µM. In some embodiments, the plasma concentration may be between about 200 µM to about 800 µM. In other embodiments, the concentration is about 300 µM to about 600 µM. In still other embodiments the plasma concentration may be between about 400 to about 800 µM. Administration of prodrugs is typically dosed at weight levels, which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-a-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

Typically, the therapeutically effective quantity of dianhydrogalactitol is about 40 mg/m$^2$. The therapeutically effective quantity of diacetyldianhydrogalactitol is similar taking into account differences in molecular weight. Other dosages can be employed, including up to 50 mg/m$^2$ for dianhydrogalactitol. Higher dosages may also be used, particularly when steps are taken to prevent myelosuppression.

Typically, the dianhydrogalactitol is administered by a route selected from the group consisting of intravenous and oral. Preferably, the dianhydrogalactitol is administered intravenously. Similar routes can be used for diacetyldianhydrogalactitol.

The method can further comprise the step of administering a therapeutically effective dose of ionizing radiation.

Another aspect of the present invention is a kit comprising, separately packaged, two or more different doses of a hexitol derivative as described above for treatment of a malignancy. Typically, the hexitol derivative is dianhydrogalactitol or diacetyldianhydrogalactitol. When the alkylating hexitol derivative is dianhydrogalactitol, the kit can comprise, but is not limited to, the following combinations of doses: (i) 1.5 mg/m$^2$ and 3.0 mg/m$^2$; (ii) 1.5 mg/m$^2$, 3.0 mg/m$^2$, and 5.0 mg/m$^2$; (iii) 1.5 mg/m$^2$, 3.0 mg/m$^2$, 5.0 mg/m$^2$, and 10 mg/m$^2$; (iv) 1.5 mg/m$^2$, 3.0 mg/m$^2$, 5.0 mg/m$^2$, 10 mg/m$^2$, and 15 mg/m$^2$; (v) 10 mg/m$^2$; (iv) 1.5 mg/m$^2$, 3.0 mg/m$^2$, 5.0 mg/m$^2$, 10 mg/m$^2$, 15 mg/m$^2$, and 20 mg/m²; (vi) 1.5 mg/m², 3.0 mg/m², 5.0 mg/m², 10 mg/m², 15 mg/m², 20 mg/m², and 25 mg/m²; (vii) 1.5 mg/m², 3.0 mg/m², 5.0 mg/m², 10 mg/m², 15 mg/m², 20 mg/m², 25 mg/m², and 30 mg/m²; (viii) 1.5 mg/m², 3.0 mg/m², 5.0 mg/m², 10 mg/m², 15 mg/m², 20 mg/m², 25 mg/m², 30 mg/m², and 40 mg/m²; and (ix) 1.5 mg/m², 3.0 mg/m², 5.0 mg/m², 10 mg/m², 15 mg/m², 20 mg/m², 25 mg/m², 30 mg/m², 40 mg/m², and 50 mg/m². Other combinations of doses including two or more of these alternative doses are also possible. The hexitol derivative can be in the form of a pharmaceutical composition. The doses can be assembled into a blister pack as is conventionally used for packaging of pharmaceutical doses. The kit can further comprise instructions for use.

The invention is illustrated by the following Examples. These Examples are included for illustrative purposes only, and are not intended to limit the invention.

Example 1

Use of Dianhydrogalactitol to Treat Patients with Recurrent Malignant Glioma or Progressive Secondary Brain Tumor Tumors of the brain are among the most challenging malignancies to treat. Median survival for patients with recurrent disease is <6 months for glioblastoma multiforme (GBM). Central Nervous System (CNS) metastases have evolved as a major contributor to cancer mortality based on improvements in systemic therapies that cannot reach tumors spreading to the brain.

Front-line systemic therapy is temozolomide but resistance due to $O^6$-methylguanine-DNA-methyltransferase (MGMT) activity is implicated in poor outcomes. Such resistance vastly reduces survival.

Dianhydrogalactitol is a first-in-class bifunctional $N^7$ DNA-alkylating agent that readily crosses the blood-brain barrier and accumulates in brain tissue. Dianhydrogalactitol causes interstrand DNA crosslinks at the $N^7$-guanine (E. Institóris et al., "Absence of Cross-Resistance Between Two Alkylating Agents: BCNU vs. Bifunctional Galactitol," *Cancer Chemother. Pharmacol.* 24: 311-313 (1989), incorporated herein by this reference), which is distinct from the mechanisms of other alkylating agents used in GBM. The use of dianhydrogalactitol as an antineoplastic agent has been described in L. Nemeth et al., "Pharmacologic and Antitumor Effects of 1,2:5,6-Dianhydrogalactitol (NSC-132313)," *Cancer Chemother. Rep.* 56: 593-602 (1972), incorporated herein by this reference. Historical clinical data further suggest comparable or enhanced survival and improved safety compared to TMZ and BCNU and reported absence of cross-resistance between dianhydrogalactitol and both TMZ and BCNU, supports the potential efficacy of dianhydrogalactitol in the treatment of GBM patients failing other agents. Dianhydrogalactitol has been granted orphan drug status by FDA and EMA for the treatment of gliomas. Previous clinical studies suggest that dianhydrogalactitol has anti-tumor activity against a range of cancers including GBM.

In in vitro studies, dianhydrogalactitol demonstrated activity in pediatric and adult GBM cell lines, as well as GBM cancer stem cells. In particular, dianhydrogalactitol can overcome resistance attributable to MGMT activity in vitro.

In light of extensive safety data from clinical trials and promising efficacy in central nervous system (CNS) tumors, we have initiated a new clinical study to establish the maximum tolerated dose (MTD) and identify a dose and dosing regimen for future efficacy trials in GBM.

Dose limiting toxicity is expected to be myelosuppression, the management of which has improved in recent years.

Early in the development of dianhydrogalactitol, a cumulative IV dose of 125 mg/m² delivered in a 35 day cycle in combination with radiation was shown superior to radiation alone in brain cancer (R. T. Eagan et al., "Dianhydrogalactitol and Radiation Therapy. Treatment of Supratentorial Glioma," *JAMA* 241: 2046-2050 (1979), incorporated herein by this reference).

As indicated above, expression of $O^6$-methylguanine methyltransferase (MGMT) has been linked to poor patient outcome in GBM patients treated with temozolomide (TMZ). The cytotoxic activity of dianhydrogalactitol is independent of the MGMT associated chemotherapeutic resistance in vitro (FIG. 1) and thus has potential to be effective in TMZ-resistant GBM.

In the present study, the cumulative dose in a 33 day cycle ranges from 9 mg/m² (cohort 1) to 240 mg/m² (cohort 7). Five dose cohorts, with the highest 33 day cycle cumulative dose of 120 mg/m², have completed the trial with no drug-related serious adverse events: MTD was not yet reached. Enrollment for cohort 6 (33 day cumulative dose: 180 mg/m²) has been initiated. The final cohort of this study, cohort 7 (33 day cumulative dose: 240 mg/m²), will be initiated subject to no dose-limiting toxicity (DLT) in cohort 6; the results will determine the design of the safety and efficacy registration trial.

The methodology of the study reported in this Example is as follows: An open-label, single arm Phase I/I dose-escalation study designed to evaluate the safety, tolerability, pharmacokinetics and anti-tumor activity of dianhydrogalactitol in patients with: (i) histologically confirmed initial diagnosis of primary WHO Grade IV malignant GBM, now recurrent, or (ii) progressive secondary brain tumor, having failed standard brain radiotherapy, and with brain tumor progression after at least one line of systemic therapy. The study utilizes a 3+3 dose escalation design, until the MTD or the maximum specified dose is reached. Patients receive dianhydrogalactitol intravenously at the assigned dose on days 1, 2, and 3 of each 21-day treatment cycle. In Phase II, additional patients will be treated at the MTD (or other selected optimum Phase II dose) to measure tumor responses. All patients enrolled have previously been treated with surgery and/or radiation, if appropriate, and must have failed both bevacizumab and TMZ, unless contraindicated. For these studies, the following is a summary of the inclusion criteria: (1) Patients must be greater than or equal to 18 years old. (2) There is a histologically confirmed initial diagnosis of primary WHO Grade IV malignant glioma (glioblastoma), now recurrent, or progressive secondary brain tumor, the patient has failed standard brain radiotherapy, and the patient has brain tumor progression after at least one line of systemic therapy. (3) If GBM, the patient has been previously treated for GBM with surgery and/or radiation, if appropriate, and the patient must have failed both bevacizumab (Avastin®) and temozolomide (Temodar®), unless either or both are contraindicated. (4) The patient must have a predicted life expectancy of at least 12 weeks. The following is a summary of the exclusion criteria: (1) There is a current history of neoplasm other than the entry diagnosis. Patients with previous cancers treated and cured with local therapy alone may be considered. (2) There is evidence of leptomeningeal spread of disease. (3) The patient had undergone prior treatment with prolifeprospan 20 with carmustine wafer (Gliadel® wafer) within 60 days prior to first treatment (Day 0). (4) The patient had undergone prior treatment with intracerebral agents. (5) The patient shows evidence of recent hemorrhage on baseline MRI of the brain. (6) The patient is being administered concomitant medications that are strong inhibitors of cytochrome P450 and CYP3A up to 14 days before Cycle 1, Day 1 (pimozide, diltiazem, erythromycin, clarithromycin, and quinidine, and amiodarone up to 90 days before.

The results are as follows: No drug-related serious adverse events have been detected, and maximum tolerated dose (MTD) has not been reached at doses up to 30 mg/m$^2$. Enrollment and evaluation of Cohort 7 (40 mg/m$^2$) is ongoing. Higher doses may be enrolled subject to completion of mandated safety observation period with Cohort 6 (30 mg/m$^2$). Patients enrolled present with refractory progressive GBM and a dire prognosis. All GBM patients enrolled to date have failed front-line temozolomide and all except one had failed second-line bevacizumab therapy. The primary endpoint of this portion of the study is to determine a modernized dosing regimen for advancement to registration-directed clinical trials. Tumor volume is measured after every second cycle and patients exhibiting any evidence of continued progression at any time during the study are discontinued, but cycle 1 toxicity is captured for MTD determination. In this design, it is not possible to perform a rigorous assessment of patient benefit due to slowed tumor growth. Tumor volume is assessed during the study based on RANO criteria. Two patients exhibiting a response (stable disease or partial response) reported in early cohorts improved clinical signs with a maximum response of 28 cycles (84 weeks) prior to discontinuing due to adverse events unrelated to study. To date, one of two patients in cohort 6 (30 mg/m$^2$) exhibited stable disease after 1 cycle of treatment. Outcomes analysis of cohort 6 is ongoing.

These preliminary data support continued exploration of higher dose cohorts.

TABLE 1

Prior Therapy, Serious Adverse Events (SAE), Dose-Limiting Toxicities (DLT) and Tumor Response of the Patients Evaluated

| Tumor Type | n | Prior Therapy | DLT | SAE | Tumor Response |
|---|---|---|---|---|---|
| GBM | 8 | Surgery/XRT/ TMZ/BEV | None | None (n = 6) Not related to study drug (n = 2)* | Overall = 25% PR (1); SD (1) |
| | 6** | Standard of care*** | None | None (n = 5) | Overall = 17% SD (1) |

*Three events in two patients;
**Breast adenocarcinoma (2); small-cell lung carcinoma (3); melanoma (1);
***Whole-brain radiotherapy and stereotactic radiosurgery when appropriate, plus at least one line of systemic therapy.

Table 2 shows a comparison of historical clinical data for dianhydrogalactitol in comparison with other therapies.

TABLE 2

Historical Clinical Data with Dianhydrogalactitol Support the Potential for Comparable or Enhanced Survival Similar to Standard Chemotherapy with an Improved Safety Profile in the Treatment of GBM

| GBM Chemotherapy | Dianhydrogalactitol (Eagan (1979)) | Temozolomide (Stupp (2005)) | Carmustine (BCNU) |
|---|---|---|---|
| Median O.S. (XRT + Chemo) | 67 weeks | 58 weeks | 40-50 weeks |

TABLE 2-continued

Historical Clinical Data with Dianhydrogalactitol Support the Potential for Comparable or Enhanced Survival Similar to Standard Chemotherapy with an Improved Safety Profile in the Treatment of GBM

| GBM Chemotherapy | Dianhydrogalactitol (Eagan (1979)) | Temozolomide (Stupp (2005)) | Carmustine (BCNU) |
|---|---|---|---|
| DLT | Hematologic | Hematologic | Hematologic |
| Nadir | 18-21 days | 21-28 days | 21-35 days |
| Recovery | Within 7-8 days | Within 14 days | 42-56 days |
| Other Severe Toxicities Reported (>2%) | None | Nausea, vomiting, fatigue, asthenia, neuropathy | Pulmonary, nausea, vomiting, encephalopathy, renal |

The references for Table 2 are as follows: "Eagan (1979)" is R. T. Eagan et al., "Dianhydrogalactitol and Radiation Therapy. Treatment of Supratentorial Glioma," *JAMA* 241: 2046-2050 (1979); "Stupp (2005)" is R. Stupp et al., "Radiotherapy Plus Concomitant and Adjuvant Temozolomide for Glioblastoma," *New. Engl. J. Med.* 352: 987-996 (2005), both of which are incorporated herein by this reference.

Table 3 is a table summarizing the dosing schedule for the trial reported in this Example.

TABLE 3

| Dose Escalation Scheme (mg/m$^2$) | | Patients Treated | Status | Cumulative dose in 33-day cycle (comparison to NCI historical regimen of 125 mg/m$^2$ per cycle) |
|---|---|---|---|---|
| Original | Revised | | | |
| 1.5 | 1.5 | 3 | Completed - No DLT | 9 mg/m$^2$ |
| 3.0 | 3.0 | 4 | Completed - No DLT | 18 mg/m$^2$ |
| 5.0 | 5.0 | 10* | Completed - No DLT | 30 mg/m$^2$ |
| 10.0 | 10.0 | 3 | Completed - NO DLT | 60 mg/m$^2$ |
| 15.0 20.0 | 20.0 | 4 | Completed - NO DLT | 120 mg/m$^2$ |
| 25.0 30.0 | 30.0 | 3 | Completed - No DLT | 180 mg/m$^2$ |
| n/a | 40.0 | 3 (planned) | Analysis ongoing Enrolling | 240 mg/m$^2$ |

*Cohorts 2 and 3 were expanded to allow for patient demand and to gather additional data on CNS metastases patients.

Figure 3:
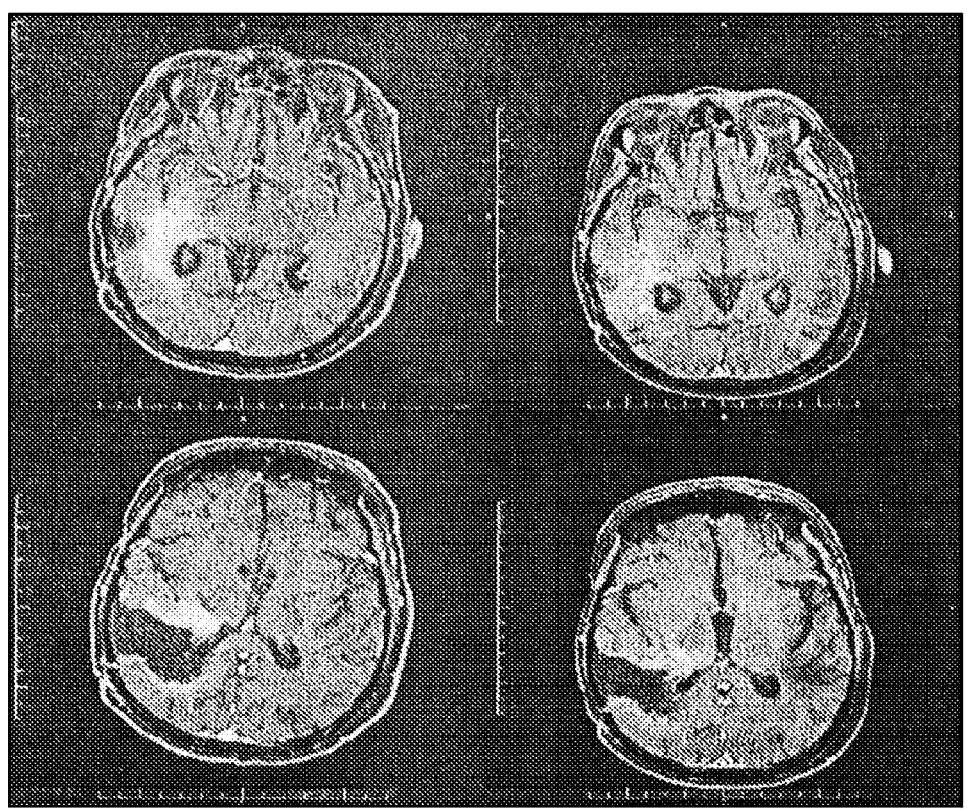
FIG. 3 shows the results from MRI scans from a human subject after two cycles dianhydrogalactitol treatment. Thick confluent regions of abnormal enhancement have diminished, now appearing more heterogeneous (left two scans, T=0; right two scans, T=64 days).

FIG. 3 shows MRI scans of a patient (Patient #26) before (at T=0 days) on the left and after (at T=64 days) on the right after two cycles of dianhydrogalactitol treatment. Thick confluent regions of abnormal enhancement have diminished, now appearing more heterogeneous.

In summary, dianhydrogalactitol shows activity against recurrent glioblastoma multiforme that has proven resistant to previous treatment with temozolomide or bevacizumab. Dianhydrogalactitol also shows activity against progressive secondary brain tumors, including tumors that arise from metastases of breast adenocarcinoma, small-cell lung carcinoma, or melanoma. Dianhydrogalactitol therefore provides a new treatment modality for treatment of these malignancies of the central nervous system, especially in circumstances where the malignancies have proven resistant to therapeutic agents such as temozolomide or bevacizumab.

In particular, dianhydrogalactitol had previously demonstrated promising clinical activity against newly-diagnosed and recurrent GBM in historical NCI-sponsored clinical trials. Dianhydrogalactitol has potent MGMT-independent cytotoxic activity against GBM cell lines in vitro. Pharmacokinetic analyses show dose-dependent increase in exposure with a short plasma 1-2 h half-life and a $C_{max}$ of <265 ng/mL (1.8 µM) at 20 mg/m$^2$ (see FIG. 2). The pharmacokinetic data is consistent with literature from previous trials, suggesting activity of dianhydrogalactitol in brain tumors; plasma concentration achieved in the 20 mg/m$^2$ cohort is sufficient to inhibit glioma cell growth in vitro. Dianhydrogalactitol therapy is well tolerated to date; no drug-related serious adverse events have been detected. The maximum tolerate dose (MTD) has not been reached after completion of cohort 6 (30 mg/m$^2$); enrollment and analysis of cohort 7 (40 mg/m$^2$) is ongoing.

Due to prior chemotherapy and radiation therapy, patients with secondary brain tumors are likely more prone to myelosuppression and may have a different MTD (maximum tolerated dose) than patients with GBM. This can be determined by assessing function of the immune system and monitoring possible myelosuppression.

Figure 1:
FIG. 1 shows the activity of dianhydrogalactitol (VAL-083) and temozolomide (TMZ) in MGMT negative pediatric human GBM cell line SF188 (first panel), MGMT negative human GBM cell line U251 (second panel) and MGMT positive human GBM cell lineT98G (third panel); immunoblots showing detection of MGMT and actin (as a control) in the individual cell lines are shown under the table providing the properties of the cell lines.
Figure 1:
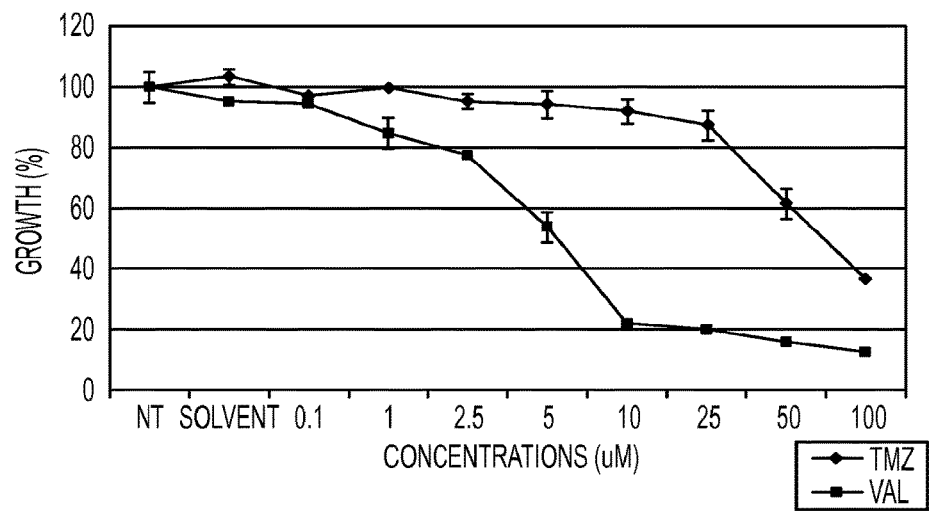
Figure 1:
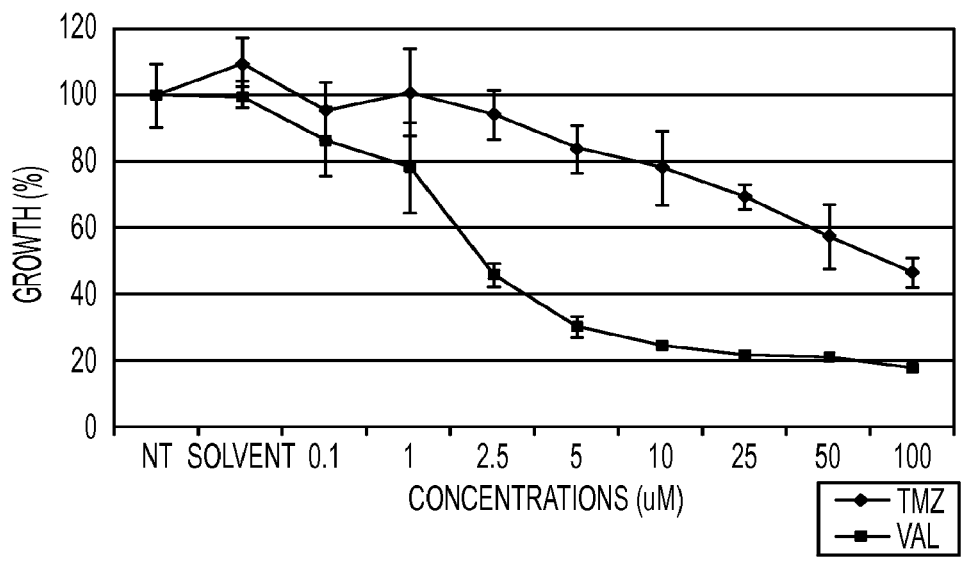
Figure 1:
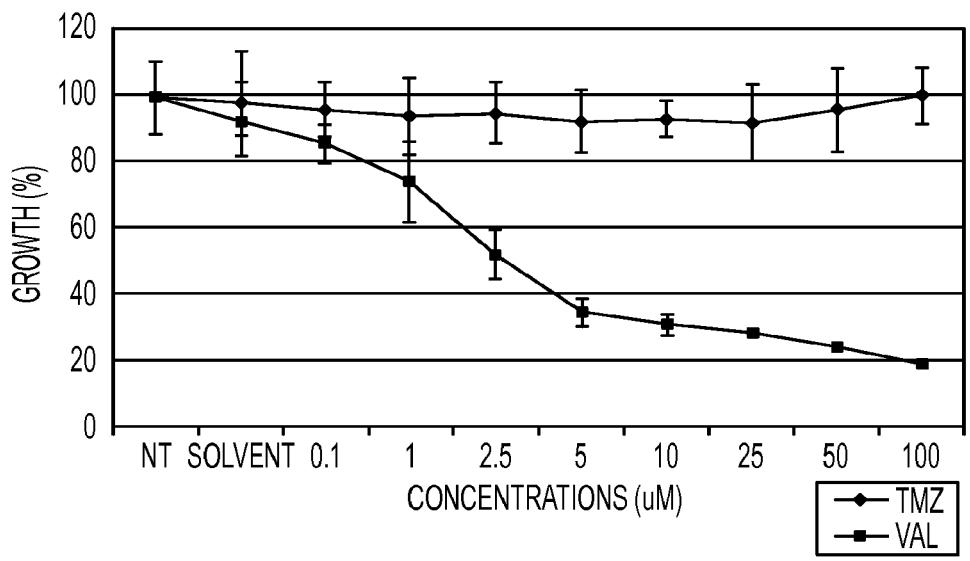

FIG. 1 shows the activity of dianhydrogalactitol (VAL-083) and temozolomide (TMZ) in MGMT negative pediatric human GBM cell line SF188 (first panel), MGMT negative human GBM cell line U251 (second panel) and MGMT positive human GBM cell lineT98G (third panel); immunoblots showing detection of MGMT and actin (as a control) in the individual cell lines are shown under the table providing the properties of the cell lines.

Dianhydrogalactitol was better than TMZ for inhibiting tumor growth in GBM cell lines SF188, U251, and T98G, activity independent of MGMT (FIG. 1). Dianhydrogalactitol furthermore inhibited the growth of cancer stem cells (BT74, GBM4 and GBM8) by 80-100% in neurosphere growth assays, with minimal effect on normal human neural stem cells (K. Hu et al., "VAL083, a Novel N7 Alkylating Agent, Surpasses Temozolomide Activity and Inhibits Cancer Stem Cells Providing a New Potential Treatment Option for Glioblastoma Multiforme," Cancer Res. 72(8) Suppl. 1: 1538 (2012), incorporated herein by this reference).

Pharmacokinetic analyses show dose-dependent systemic exposure with a short plasma 1-2 h half-life; average $C_{max}$ at 20 mg/m$^2$ is 266 ng/mL (0.18 µg/mL or ~1.8 µM). Pharmacokinetic analyses of cohort 6 (30 mg/m$^2$) are ongoing. In previous clinical trials using less sensitive bioanalytical methods than today's LC-MS-MS method (R. T. Eagan et al., "Clinical and Pharmacologic Evaluation of Split-Dose Intermittent Therapy with Dianhydrogalactitol," Cancer Treat. Rep. 66: 283-287 (1982), incorporated herein by this reference), iv infusion of approximately 3-4 times higher doses (60-72 mg/m$^2$) led to $C_{max}$ ranging from 1.9 to 5.6 µg/mL, and the concentration-time curve was bi-exponential, similar to the finding in the current trial. Pharmacokinetics are linear and consistent with previous published data suggesting higher levels can be achieved at higher doses in the current trial. In vitro studies indicate that µM concentrations of dianhydrogalactitol), as obtained in cohorts 4, 5 and 6, are effective against various glioma cell lines (as shown in FIG. 1). FIG. 2 shows the plasma concentration-time profiles of dianhydrogalactitol showing dose-dependent systemic exposure (mean of 3 subjects per cohort). FIG. 3 shows the results from MRI scans from a human subject after two cycles dianhydrogalactitol treatment. Thick confluent regions of abnormal enhancement have diminished, now appearing more heterogeneous (left two scans, T=0; right two scans, T=64 days).

Example 2

Dianhydrogalactitol Inhibits the Growth of Glioma Stem and Non-Stem Cultures, Including Temozolomide-Resistant Cell Lines, In Vitro and In Vivo Dianhydrogalactitol inhibits the growth of glioma stem and non-stem cultures, including temozolomide-resistant cell lines, in vitro and in vivo.

The standard of care for glioblastoma multiforme (GBM) patients is surgical resection followed by temozolomide (TMZ) and irradiation (XRT). However, TMZ-resistance has emerged as a significant unmet medical need, as DNA repair enzyme O$^6$-methylguanine DNA methyltransferase (MGMT) removes the methyl-group adducts caused by TMZ. Dianhydrogalactitol (VAL-083) is a structurally unique alkylating agent causing DNA crosslinks at N7 position of guanine. Because VAL-083's N7 adducts are not subject to MGMT mediated repair, it may be an effective chemotherapeutic in the treatment of TMZ-resistant GBM. VAL-083 crosses the blood brain barrier and accumulates in brain tumor tissue. We have recently shown that TMZ activity is similar in cancer stem cells (CSC) and their paired non-CSC from primary GBM tissues, and that the activity is MGMT-dependent. We thus sought to investigate how our CSC and non-CSC panel would respond to VAL-083 alone or in combination with XRT. We further investigated the activity of VAL-083 in in vivo models of drug-resistant GBM in comparison to TMZ. Rag2 mice bearing intracranial human GBM xenograft tumors of either MGMT-positive and TMZ-resistant origin (BT74), or MGMT-negative and TMZ-sensitive origin (U251) were treated. VAL-083 was given i.p. 3 times/week×3 weeks, and the efficacy of VAL-083 in controlling tumor growth compared to TMZ (30 mg/kg). Disease progression was evaluated by overall survival, clinical observations and body weight measurements. Our in vitro results show that VAL-083 is a potent inhibitor of all tested primary GBM cultures, irrespective of MGMT status. VAL-083 causes cell cycle arrest and loss of cell viability in TMZ-resistant cells, and at lower concentrations than TMZ in TMZ-sensitive cells.

Furthermore, VAL-083 is not affected by cell culture condition (Stem vs. Non-Stem). Low dose VAL-083 combined with XRT exhibited an additive effect in all cultures tested, suggesting that VAL-083 might act as a radiosensitizer. In the in vivo U251 model, the median survival time for mice treated with 4 mg/kg VAL-083 was significantly increased to 72 days compared to 48 days for controls (p<0.0001). Median survival time for 3 mg/kg VAL-083 was 54 days. Body weight loss was observed in mice treated with 5 mg/kg and treatment was stopped after 4 doses after which the animals recovered and their median survival was 57 days. Animals treated with TMZ were terminated at day 102 at the end of the study. In conclusion, VAL-083 is highly efficacious against both stem and non-stem GBM cell cultures in vitro, the activity is independent of MGMT and VAL-083 appears to act as a radiosensitizer in GBM. In vivo xenograft GBM models further validate the benefits of VAL-083 in the treatment of GBM and support ongoing clinical research with VAL-083, which is currently in a clinical trial for GBM patients with recurrent disease.

A summary of the cultures tested is shown in Table 4. "VAL" refers to dianhydrogalactitol and "XRT" refers to radiation. "CSC" refers to cancer stem cells, while "non-CSC" refers to non-cancer-stem cell cultures.

TABLE 4

| Cell Line | FACS Val#1 | FACS Val#2 | FACS VAL/XRT#1 | FACS VAL/XRT#2 | Cell Viability VAL/XRT#1 | Cell Viability VAL/XRT#2 |
|---|---|---|---|---|---|---|
| 7996 CSC | X | X | X | | X | |
| 7996 Non-CSC | X | X | X | | X | |
| 8161 CSC | X | X | X | | X | |
| 8161 Non-CSC | X | X | | | | |
| 8279 CSC | X | | | | | |
| 8565 CSC | X | | X | | X | |
| 8565 Non-CSC | X | X | | | | |
| 9030 CSC | X | | X | | X | |
| U251 | X | X | X | | X | |

Figure 4:
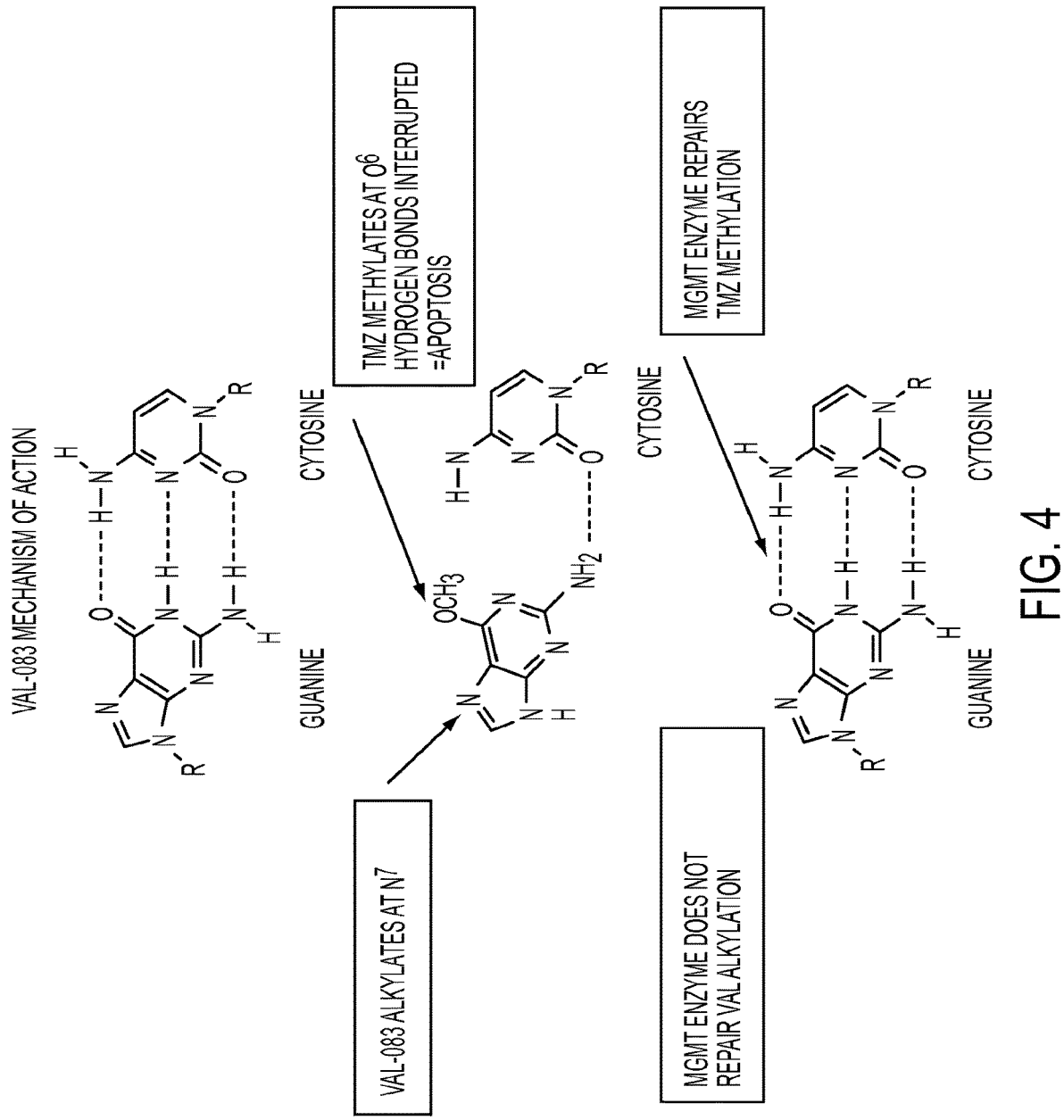
FIG. 4 shows the mechanism of action for dianhydrogalactitol ("VAL-083").

The mechanism of action for dianhydrogalactitol ("VAL-083") is shown in FIG. 4.

Figure 5C:
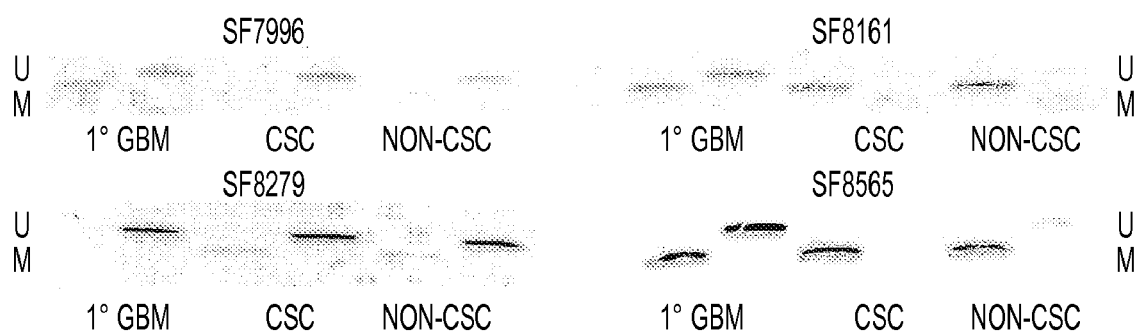
FIG. 5C shows the methylation status of MGMT for cell lines SF7996, SF8161, SF8279, and SF8565; "U" refers to unmethylated and "M" refers to methylated.
Figure 5D:
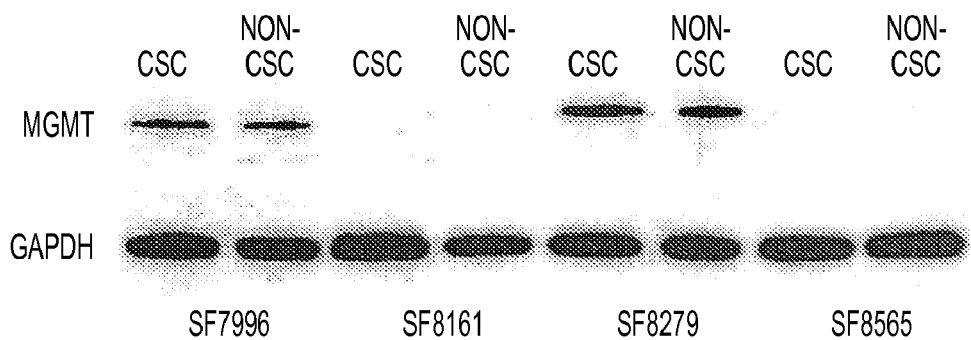
FIG. 5D shows MGMT western blot analysis of protein extracts from 4 pairs of CSC and non-CSC cultures derived from primary GBM tissue.

FIG. 5, shown as FIGS. 5C and 5D, shows the MGMT status of the cultures. "GAPDH" refers to glyceraldehyde-3-phosphate dehydrogenase as a control. For the cell cultures, CSCs were cultured in NSA media supplemented with B27, EGF and bFGF. Non-CSCs were grown in DMEM:F12 with 10% FBS. MGMT methylation and protein expression analysis of each culture was characterized. TMZ or VAL-083 was added to the cultures in the indicated concentrations. Depending on the experiment, cells were also irradiated with 2 Gy in a Cesium irradiator. For assays, cell cycle analysis was performed with Propidium Iodide staining and FACs analysis. Cell viability was analyzed with CellTiter-Glo and read on a Promega GloMax. FIG. 5C shows the methylation status of MGMT for cell lines SF7996, SF8161, SF8279, and SF8565; "U" refers to unmethylated and "M" refers to methylated. In FIG. 5, "1° GBM" refers to primary glioblastoma multiforme cell cultures. FIG. 5D shows MGMT western blot analysis of protein extracts from 4 pairs of CSC and non-CSC cultures derived from primary GBM tissue.

Figure 6:
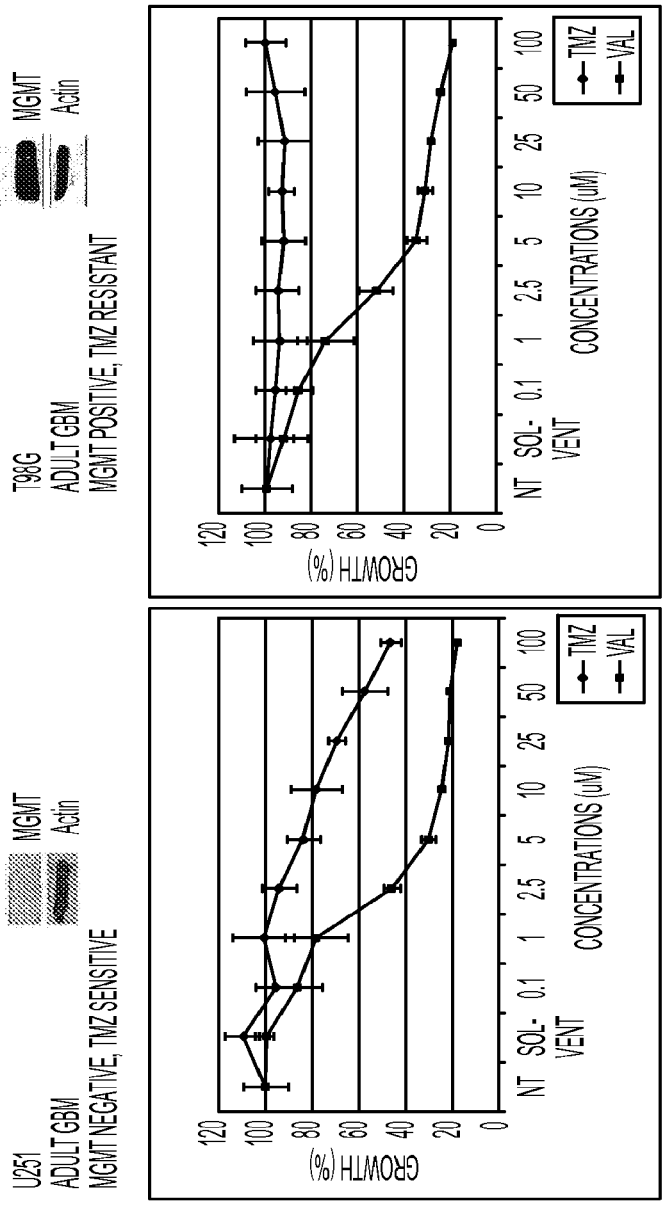
FIG. 6 shows that dianhydrogalactitol ("VAL-083") was better than TMZ for inhibiting tumor cell growth and that this occurred in an MGMT-independent manner.

FIG. 6 shows that dianhydrogalactitol ("VAL-083") was better than TMZ for inhibiting tumor cell growth and that this occurred in an MGMT-independent manner.

Figure 7:
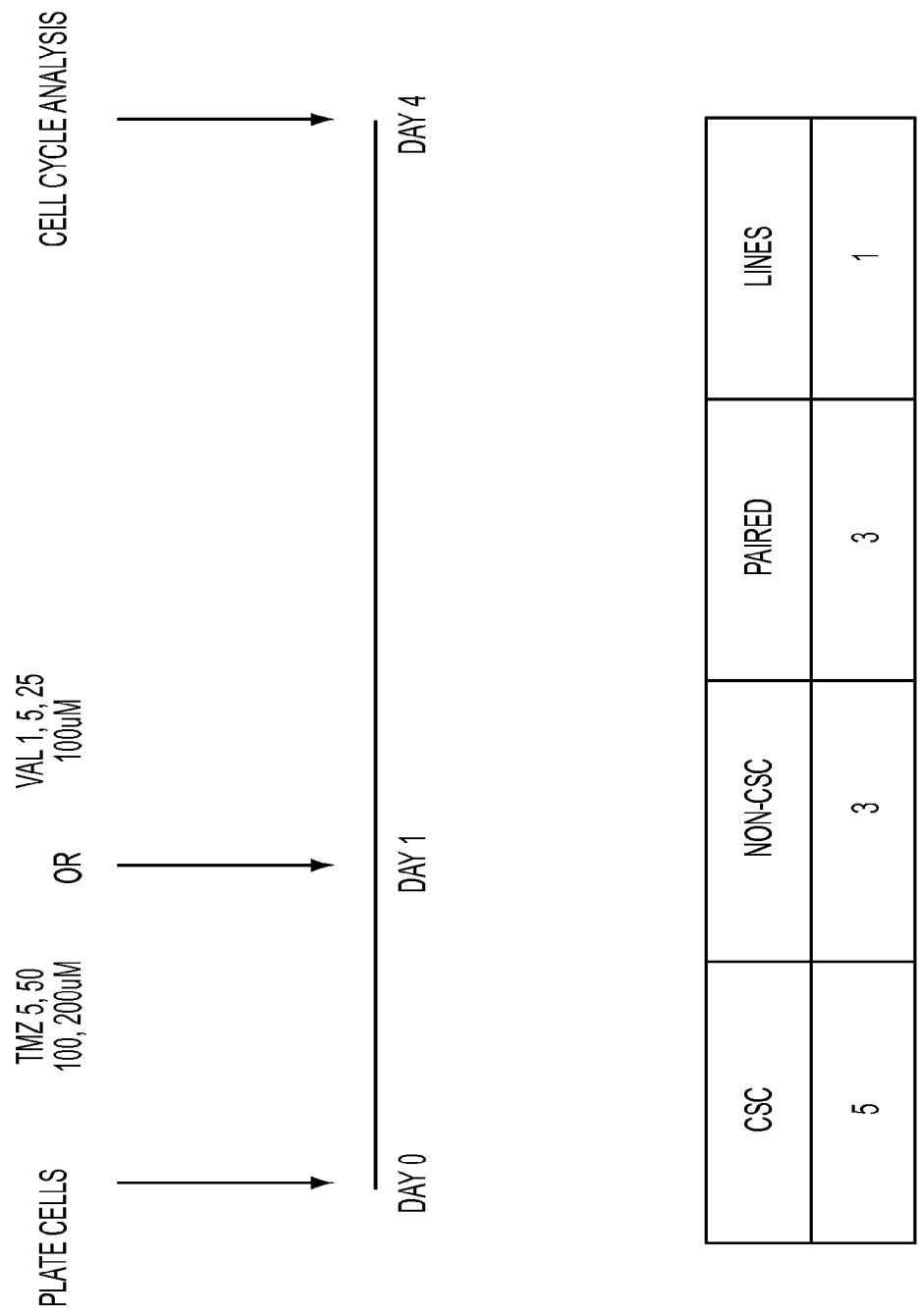
FIG. 7 shows schematics of various in vitro treatment regimens for temozolomide ("TMZ") or dianhydrogalactitol ("VAL"), with or without radiation ("XRT").

FIG. 7 shows schematics of various in vitro treatment regimens for temozolomide ("TMZ") or dianhydrogalactitol ("VAL"), with or without radiation ("XRT").

Figure 8:
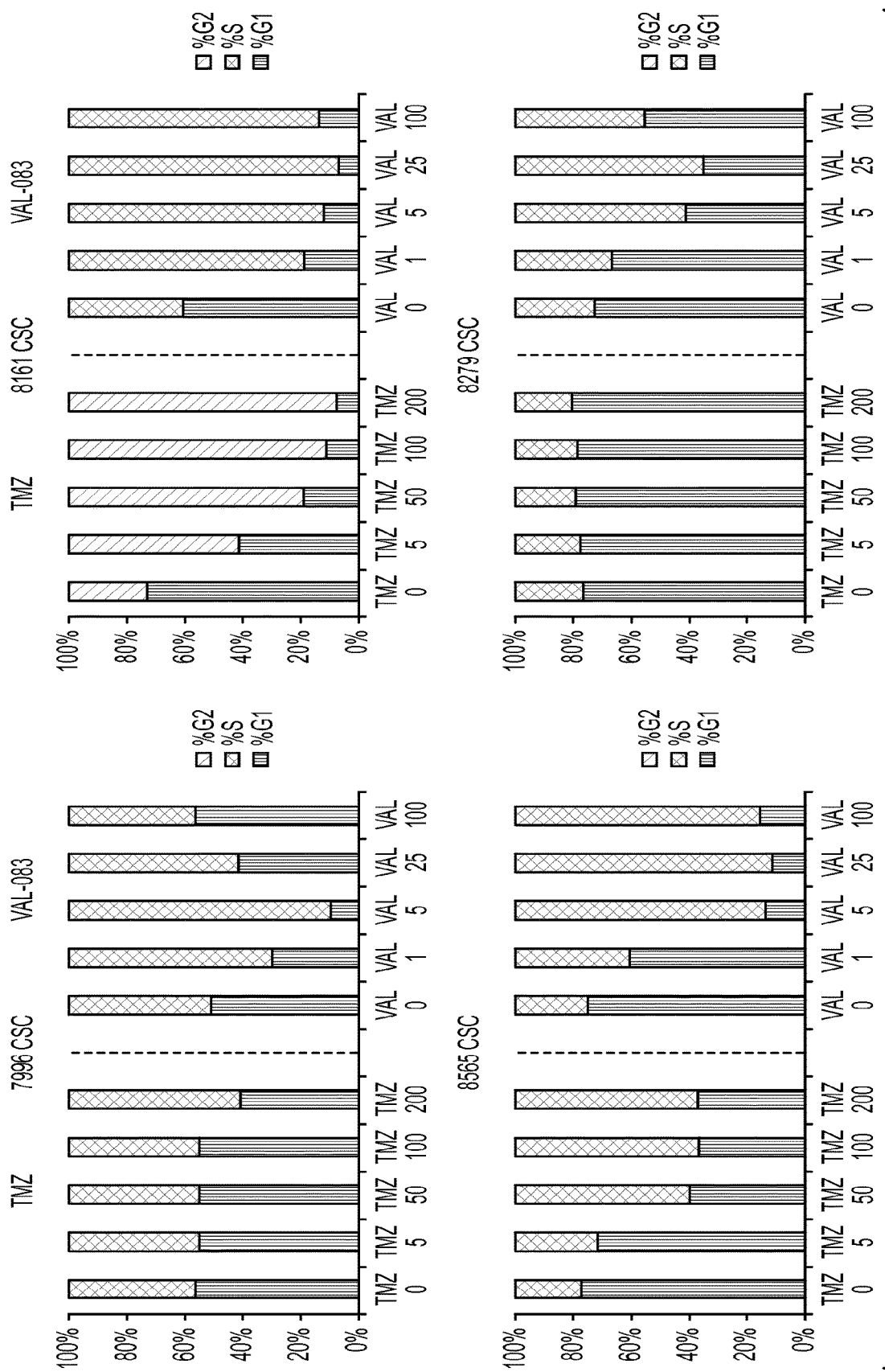
FIG. 8 shows cell cycle analyses for cancer stem cells (CSC) treated with TMZ or dianhydrogalactitol ("VAL-083") in vitro, for 7996 CSC, 8161 CSC, 8565 CSC, and 8279 CSC. In these cell cycle analyses, G2 is shown at the top, S in the middle, and G1 at the bottom.

FIG. 8 shows cell cycle analyses for cancer stem cells (CSC) treated with TMZ or dianhydrogalactitol ("VAL-083") in vitro, for 7996 CSC, 8161 CSC, 8565 CSC, and 8279 CSC. In these cell cycle analyses, G2 is shown at the top, S in the middle, and G1 at the bottom.

Figure 9:
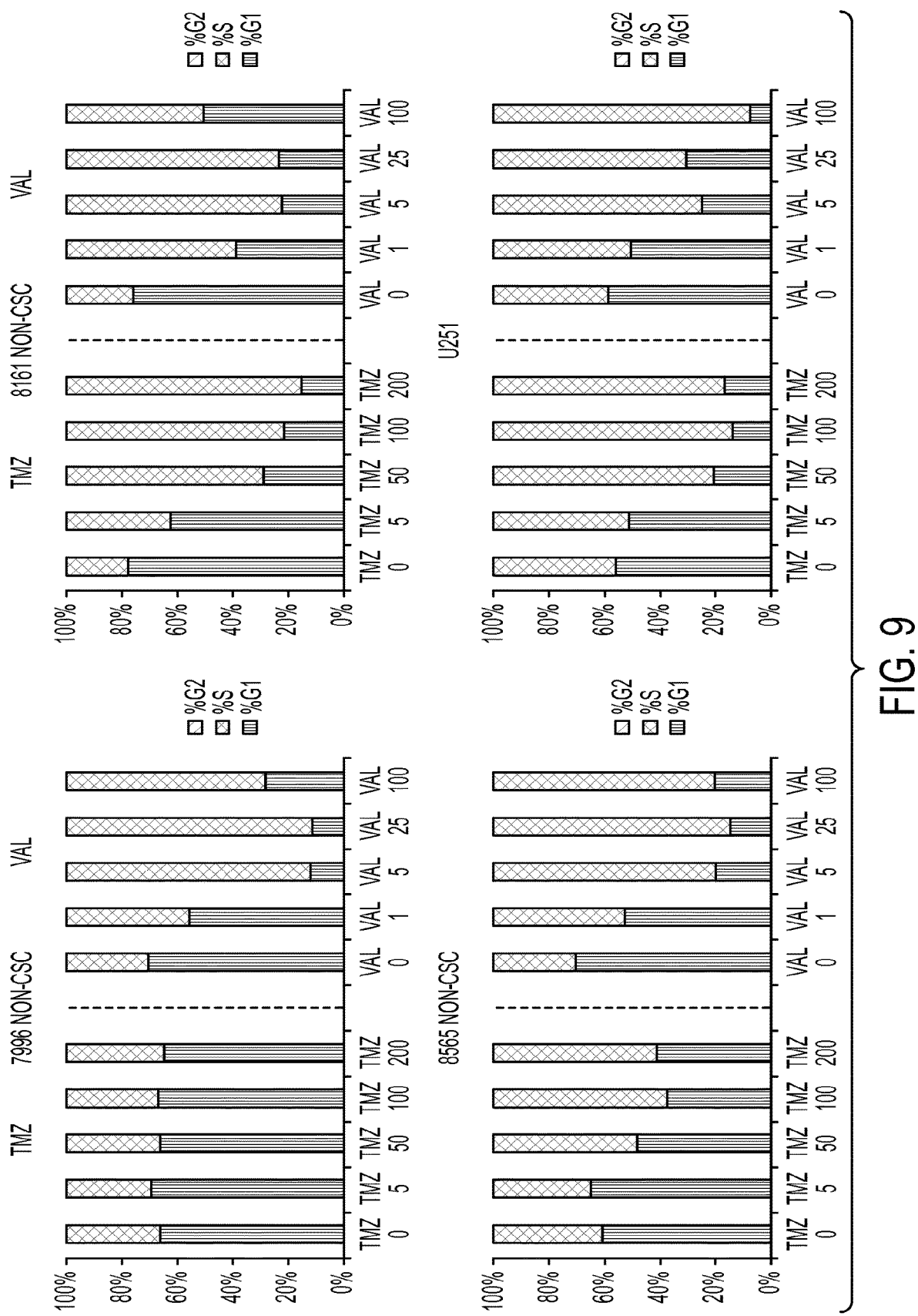
FIG. 9 shows cell cycle analyses for non-stem-cell cultures treated with TMZ or dianhydrogalactitol ("VAL-083") in vitro, for 7996 non-CSC, 8161 non-CSC, 8565 non-CSC, and U251. In these cell cycle analyses, G2 is shown at the top, S in the middle, and G1 at the bottom.

FIG. 9 shows cell cycle analyses for non-stem-cell cultures treated with TMZ or dianhydrogalactitol ("VAL-083") in vitro, for 7996 non-CSC, 8161 non-CSC, 8565 non-CSC, and U251. In these cell cycle analyses, G2 is shown at the top, S in the middle, and G1 at the bottom.

Figure 10:
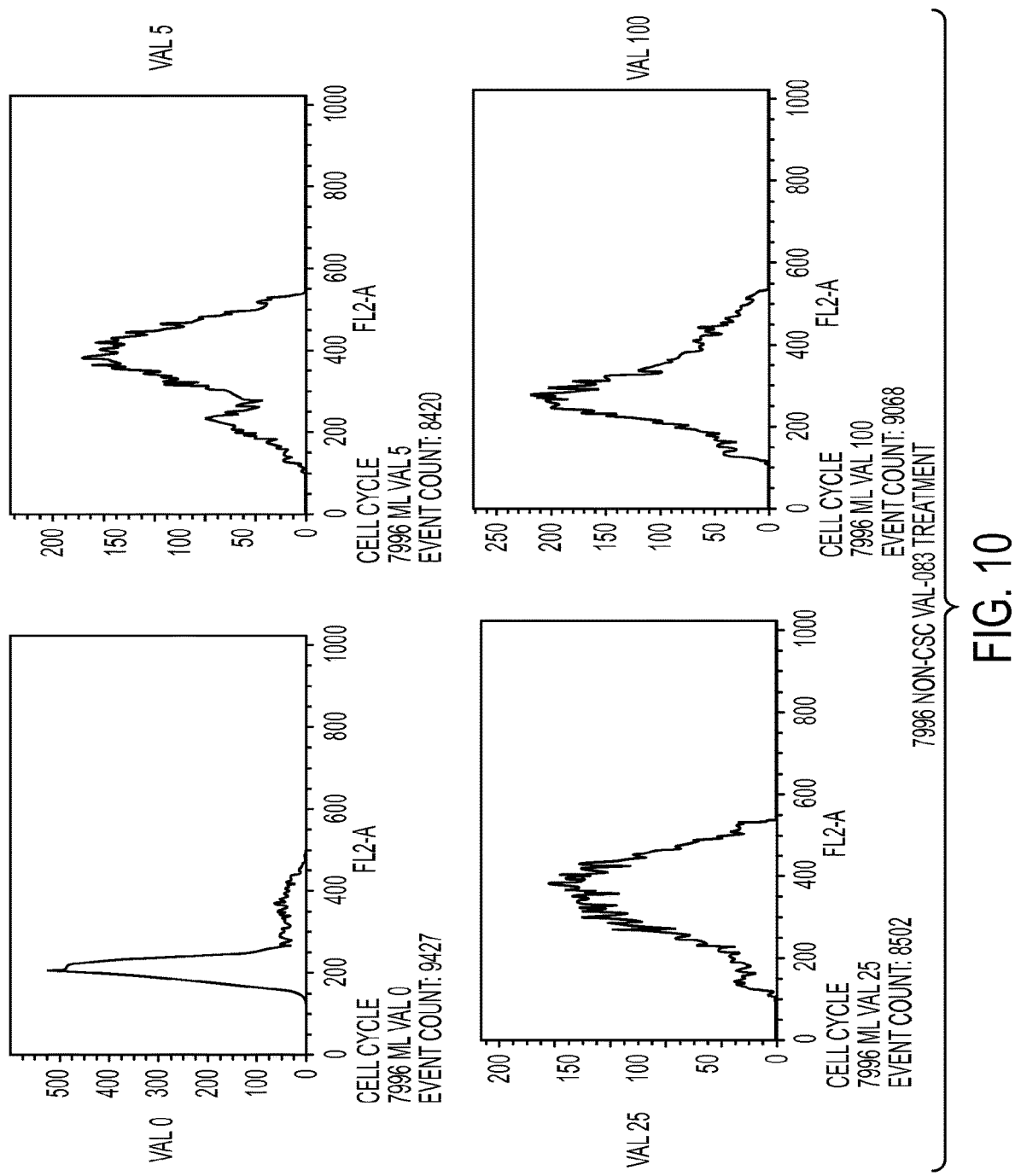
FIG. 10 shows examples of FACS profiles for 7996 non-CSC cells after dianhydrogalactitol ("VAL") treatment in varying dosages.

FIG. 10 shows examples of FACS profiles for 7996 non-CSC cells after dianhydrogalactitol ("VAL") treatment in varying dosages.

Regarding these results, dianhydrogalactitol appears to cause cell death at lower concentrations than temozolomide. Odd cell cycle profiles appear in some cultures; in some cases, there is a dip in G1 at a small dianhydrogalactitol dose (1-5 µM) and then G1 appears to recover at a larger dose (100 µM). The activity of dianhydrogalactitol is not affected by MGMT status or the stem-cell or non-stem-cell status of the culture.

Figure 11:
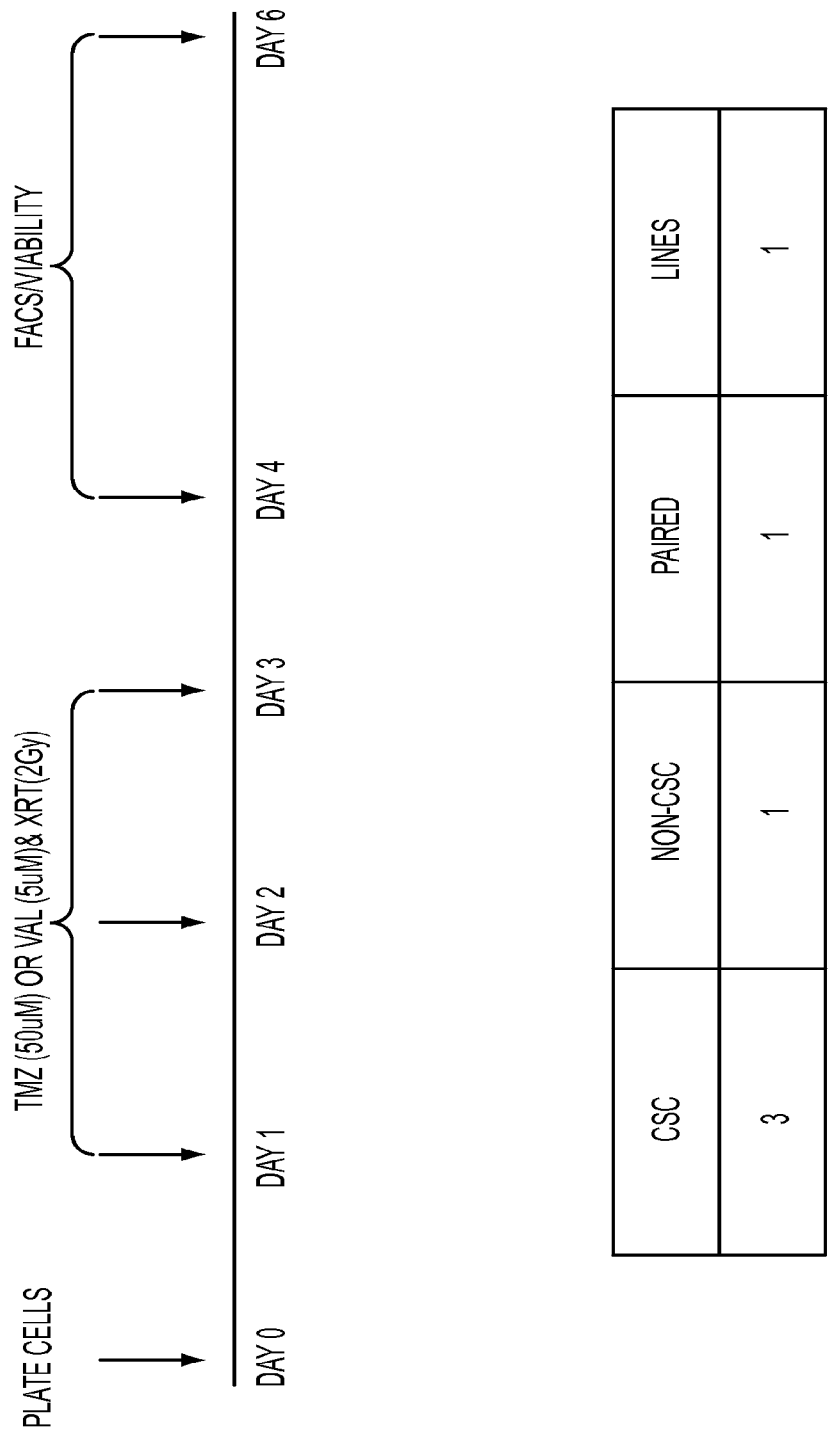
FIG. 11 shows a schematic of the in vitro treatment regimen using either temozolomide ("TMZ") or dianhydrogalactitol ("VAL") and radiation ("XRT").

FIG. 11 shows a schematic of the in vitro treatment regimen using either temozolomide ("TMZ") or dianhydrogalactitol ("VAL") and radiation ("XRT").

Figure 12:
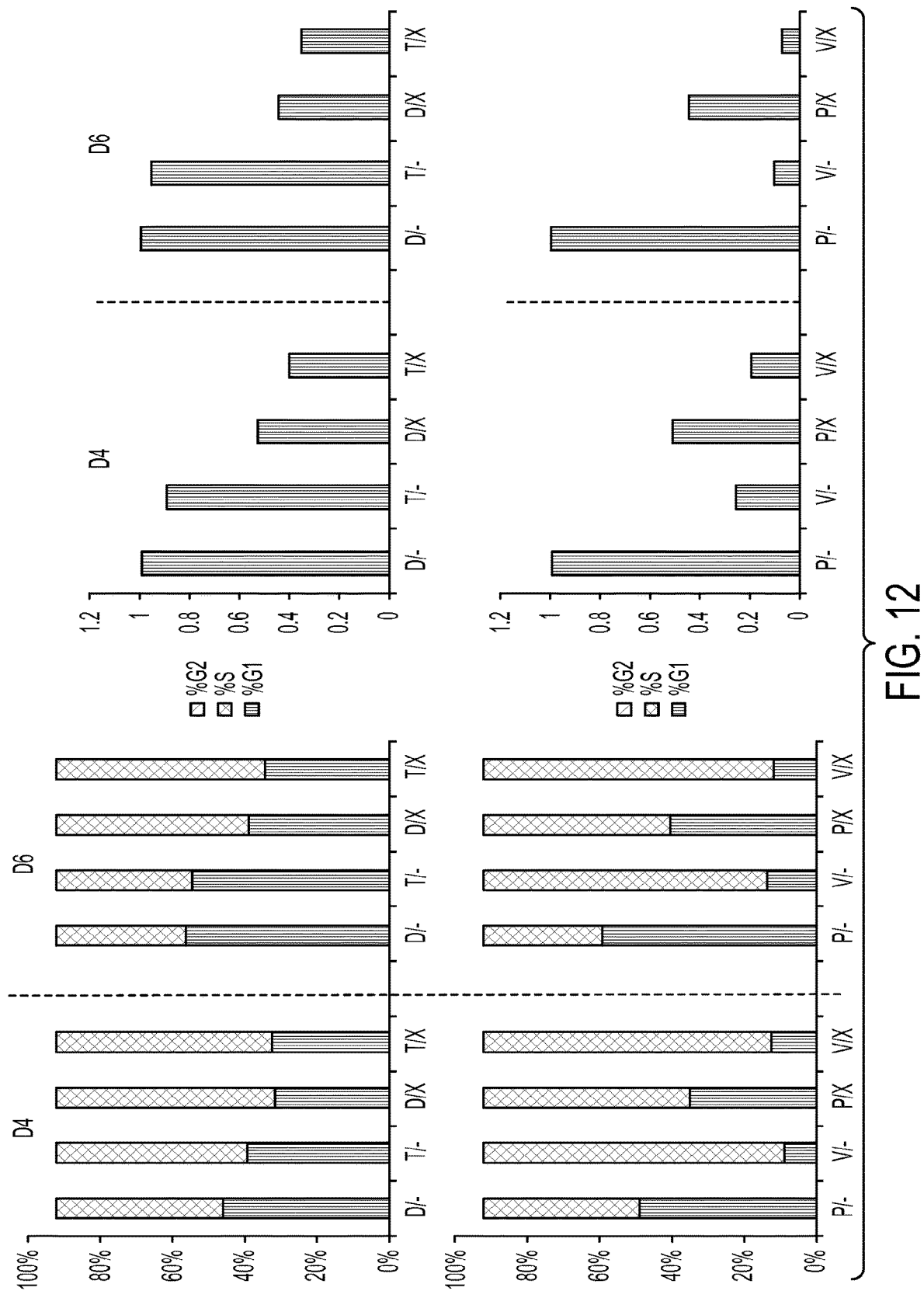
FIG. 12 shows in vitro results for 7996 CSCs after treatment with TMZ only, VAL only, and TMZ or VAL with XRT.

FIG. 12 shows in vitro results for 7996 CSC for TMZ only, VAL only, and TMZ or VAL with XRT. In FIG. 12, for TMZ "-D/-" indicates DMSO only (vehicle), "-T/-" indicates TMZ only, and "-D/X" or "-T/X" indicate DMSO or TMZ with XRT. Similarly, for VAL, "-P/-" indicates phosphate buffered saline (PBS) only (vehicle), "-V/-" indicates VAL only, and "-P/X" or "-V/X" indicate PBS or VAL with XRT. The left side of FIG. 12 shows cell cycle analysis where G2 is shown at the top, S in the middle, and G1 at the bottom; both 4- and 6-day results are shown, with the 4-day results ("D4") presented to the left of the 6-day results ("D6"). The right side of FIG. 12 shows the results for cell viability as a percentage of control for D4 and D6.

Figure 13:
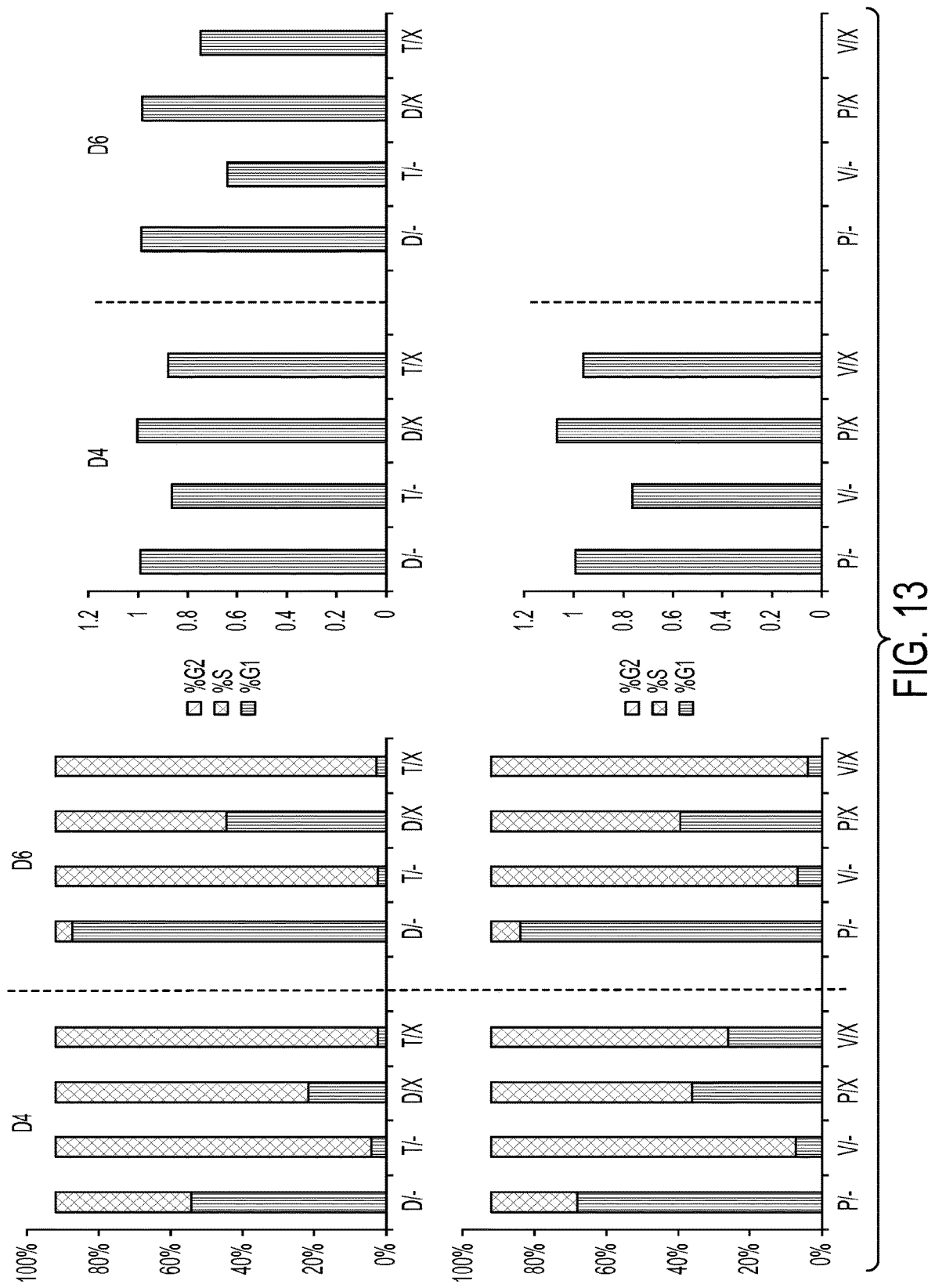
FIG. 13 shows results for 8161 CSCs depicted as in FIG. 12.

FIG. 13 shows results for 8161 CSCs depicted as in FIG. 12.

Figure 14:
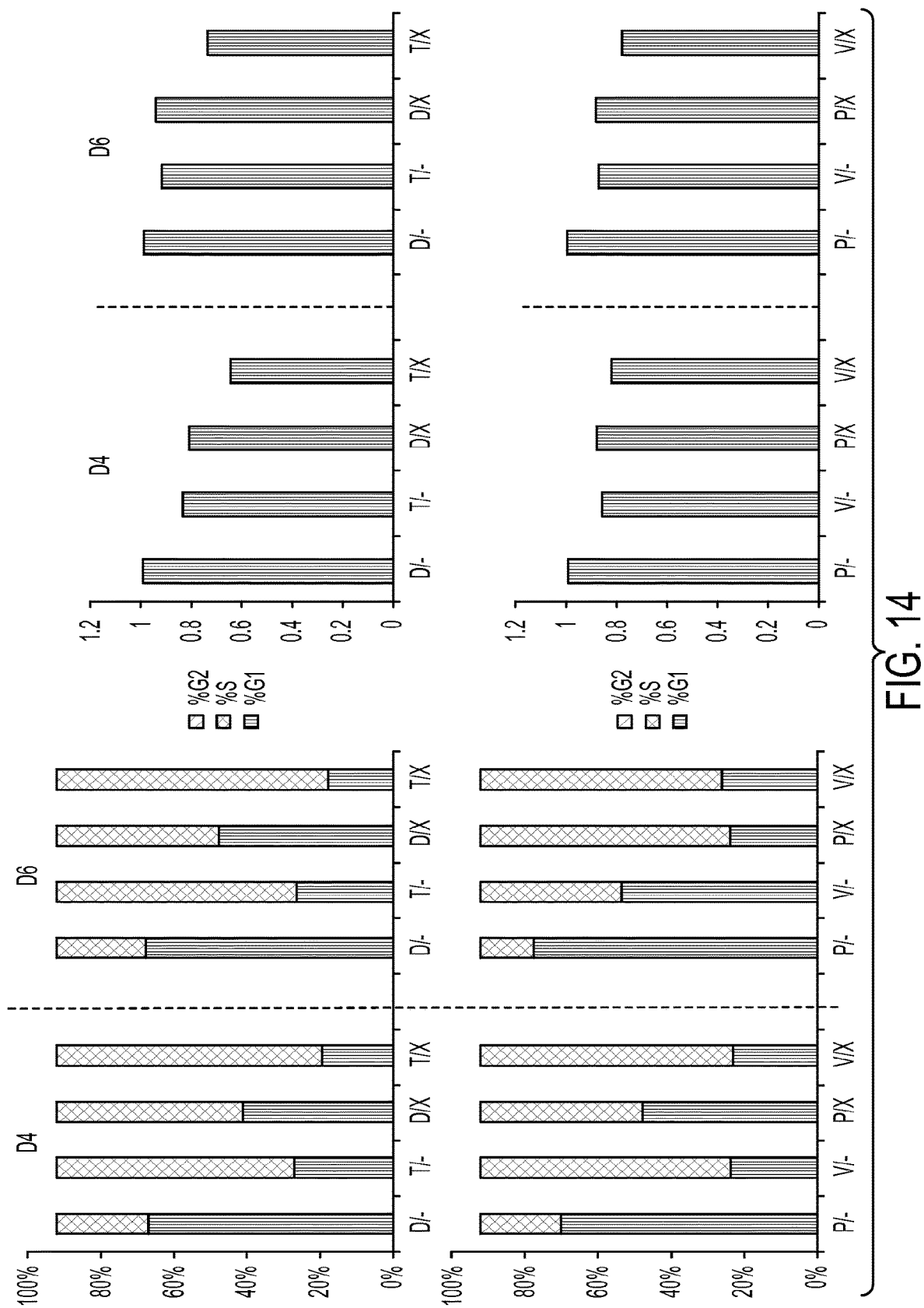
FIG. 14 shows results for 8565 CSCs depicted as in FIG. 12.

FIG. 14 shows results for 8565 CSCs depicted as in FIG. 12.

Figure 15:
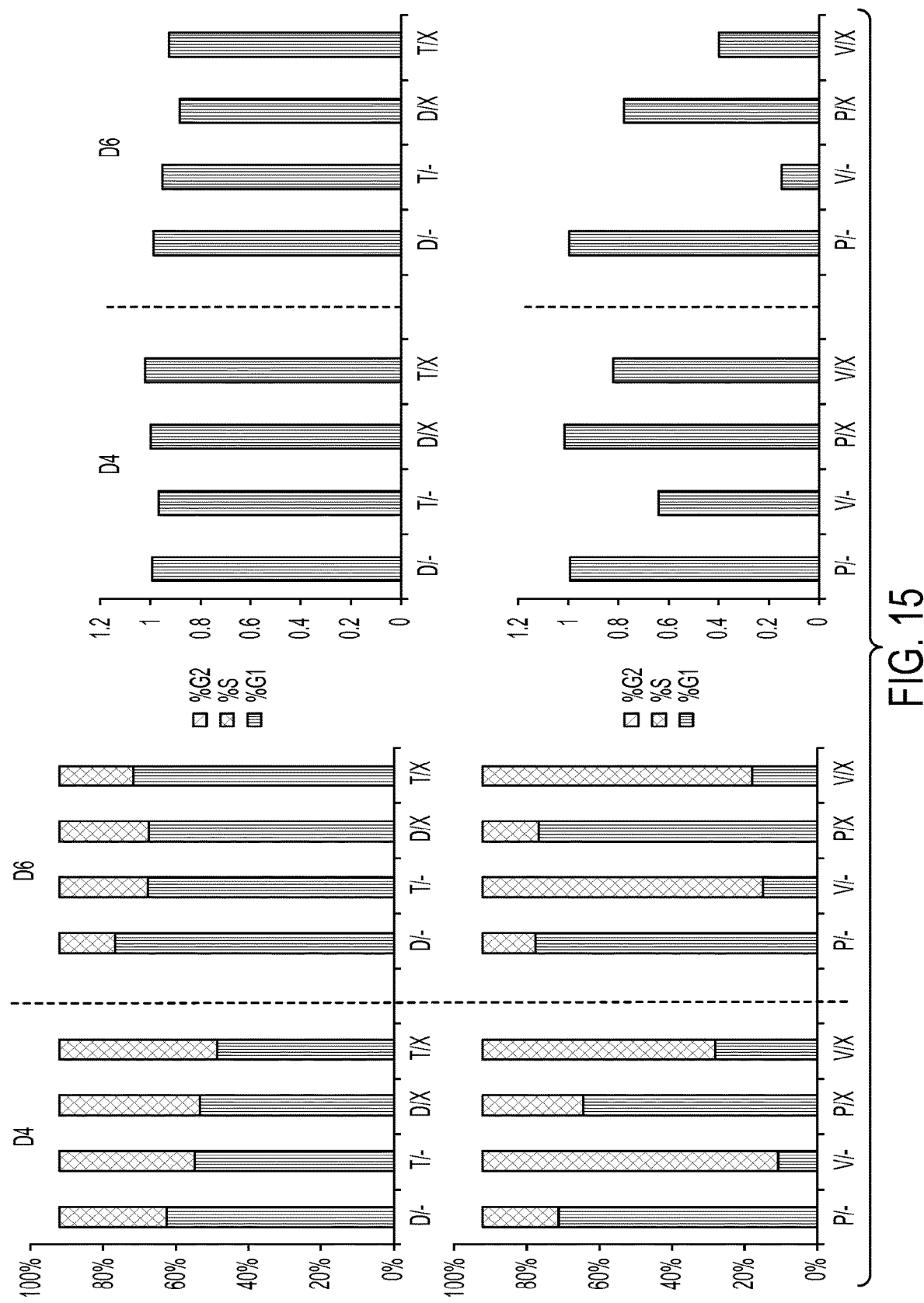
FIG. 15 shows results for 7996 non-CSCs depicted as in FIG. 12.

FIG. 15 shows results for 7996 non-CSCs depicted as in FIG. 12.

Figure 16:
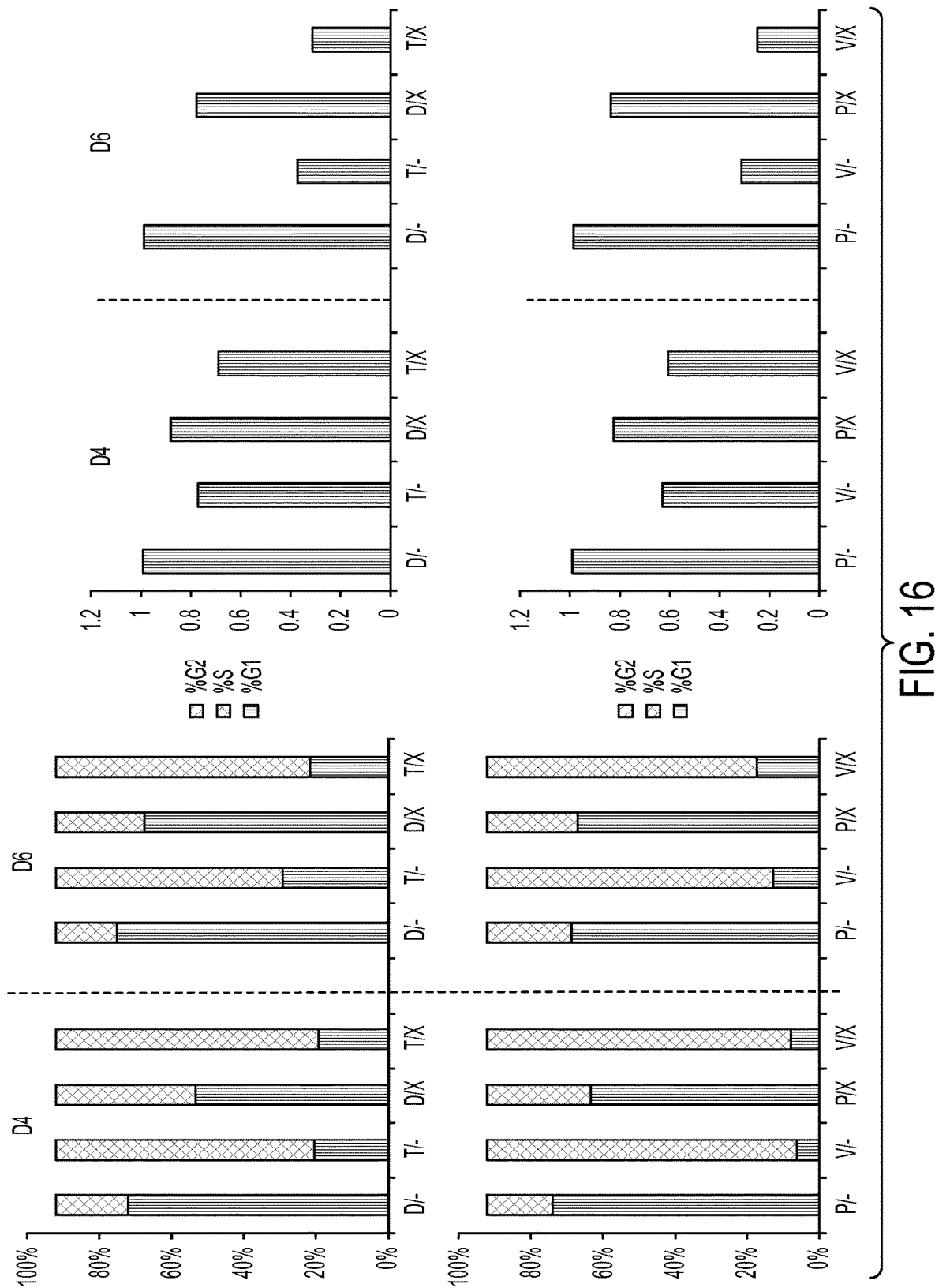
FIG. 16 shows results for GBM cell line U251 depicted as in FIG. 12.
Figure 18A:
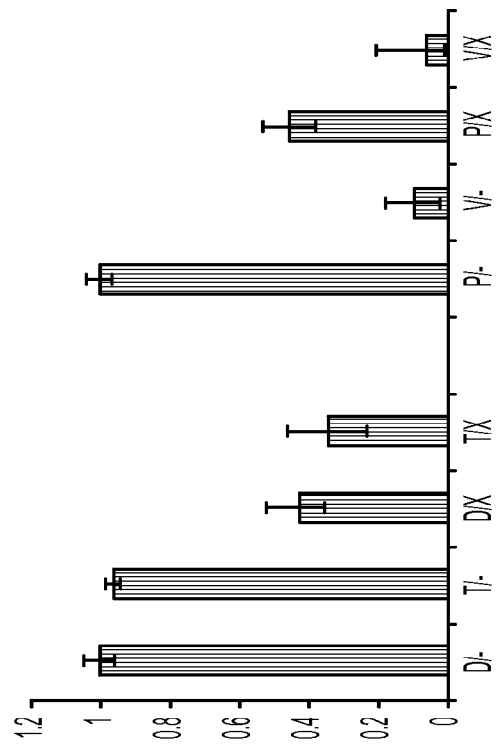
Figure 18B:
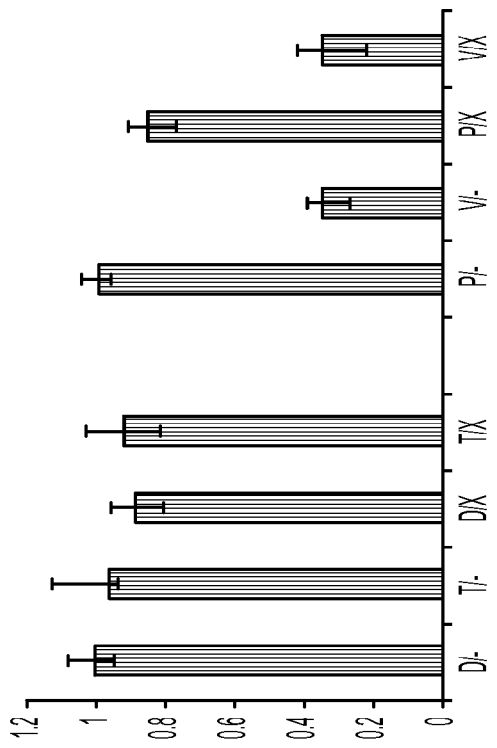
Figure 18C:
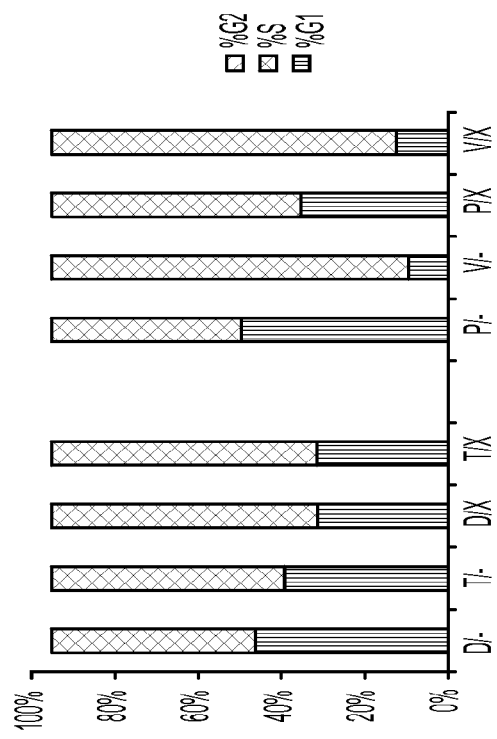
Figure 18D:
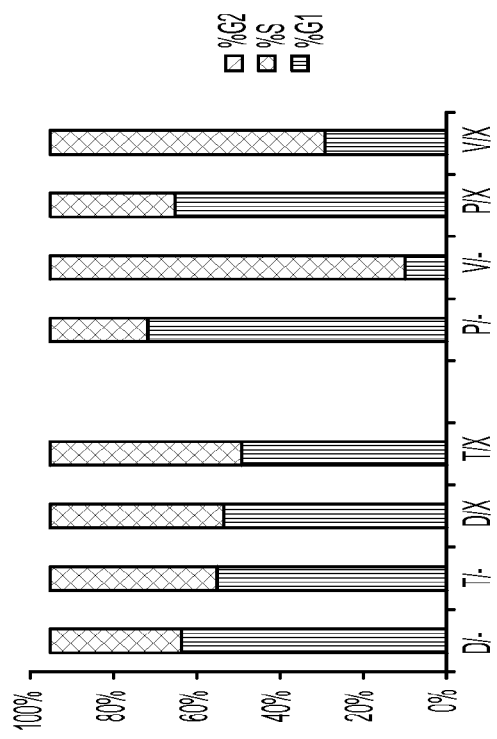

FIG. 16 shows results for GBM cell line U251 depicted as in FIG. 12.

FIG. 17, shown as FIGS. 17A, 17B, 17C, and 17D, shows that dianhydrogalactitol causes cell cycle arrest in TMZ-resistant cultures in vitro. In FIG. 17, cells were treated with either increasing doses of TMZ (5, 50 100 and 200 µM) or dianhydrogalactitol ("VAL-083") (1, 5, 25 and 100 µM) and cell cycle analysis was performed 4 days post treatment. TMZ resistant cultures (FIG. 17A, FIG. 17B, FIG. 17D) exhibited sensitivity to VAL-083, even at single-micromolar doses. Furthermore, this response was not dependent on culture type as paired CSC (FIG. 17A) and non-CSC (FIG. 17B) both exhibit sensitivity to VAL-083.

FIG. 18, shown as FIGS. 18A, 18B, 18C, and 18D, shows that dianhydrogalactitol decreases cell viability in TMZ-resistant cultures in vitro. In FIG. 18, TMZ (50 µM) or dianhydrogalactitol ("VAL-083") (5 µM) were added to primary CSC cultures at various doses with or without irradiation (2 Gy). Shown are cell cycle profile analysis at day 4 post treatment (FIG. 18A, FIG. 18C) and cell viability analysis at day 6 post treatment (FIG. 18B, FIG. 18D) for the paired CSC (FIG. 18A, FIG. 18B) and non-CSC (FIG. 18C, FIG. 18D) 7996 culture. Whereas these cultures are not very sensitive to TMZ, they are to VAL-083. However, the addition of radiation (XRT) in both cases does not result in increased sensitivity (D=DMSO, T=TMZ, X=XRT, P=PBS).

FIG. 19, shown as FIGS. 19A, 19B, 19C, and 19D, shows that dianhydrogalactitol at low dosages acts as a radiosensitizer in primary CSC cultures. In FIG. 19, dianhydrogalactitol ("VAL-083") was added to primary CSC cultures at various doses (1, 2.5 and 5 µM) with or without irradiation (2 Gy). Shown are cell cycle profile analysis at day 4 post treatment (FIG. 19A, FIG. 19C) and cell viability analysis at day 6 post treatment (FIG. 19B, FIG. 19D) for two different patient-derived CSC cultures, 7996 (FIG. 19A, FIG. 19B) and 8565 (FIG. 19C, FIG. 19D).

Additional experiments were performed to test the effect of the duration of drug administration. Temozolomide was added for 3 hours and then washed out. Dianhydrogalactitol was left on for the duration of the treatment. These experiments were performed to determine the results if temozolomide was left on indefinitely or if dianhydrogalactitol was washed out after 3 hours.

FIG. 20 shows the treatment regimens with a wash or no wash for both dianhydrogalactitol and temozolomide.

FIG. 21 shows the results for 7996 GNS, showing cell cycle analysis where G2 is shown at the top, S in the middle, and G1 at the bottom. Results for TMZ are shown on the top and results for dianhydrogalactitol on the bottom. Results with a wash are shown on the left and results without a wash are shown on the right.

FIG. 22 shows the results for 8279 GNS, depicted as in FIG. 21.

FIG. 23 shows the results for 7996 ML, depicted as in FIG. 21.

FIG. 24 shows the results for 8565 ML, depicted as in FIG. 21.

In these experiments, temozolomide did not appear to have any more effect if left on for longer than 3 hours. Dianhydrogalactitol had less effect when washed out after 3 hours.

FIG. 25 shows the treatment regimens for combining dianhydrogalactitol ("VAL") and radiation ("XRT").

FIG. 26 shows the results for 7996 GNS (CSC) when dianhydrogalactitol is combined with radiation. Results are shown at day 4 ("D4") on the top and day 6 ("D6") on the bottom. The left side shows cell cycle analysis where G2 is shown at the top, S in the middle, and G1 at the bottom. The right side shows cell viability at D4 and D6.

FIG. 27 shows the results for 8565 GNS (CSC) as depicted in FIG. 26.

FIG. 28 shows the results for 7996 ML (non-CSC) as depicted in FIG. 26.

FIG. 29 shows the results for 8565 ML (non-CSC) as depicted in FIG. 26.

In summary, dianhydrogalactitol results in cell cycle arrest and loss of cell viability in nearly all cultures tested. Dianhydrogalactitol appears to cause cell cycle arrest and loss of cell viability at lower concentrations than temozolomide. Furthermore, the efficacy of dianhydrogalactitol is not affected by MGMT status or cell culture condition (stem versus non-stem) as all primary cultures tested were sensitive to dianhydrogalactitol exposure. For all cultures tested, a potential additive effect of dianhydrogalactitol with radiation was seen, particularly at low concentrations of dianhydrogalactitol, such as 1 µL. This was most pronounced in 7996 GNS (CSC) with 20% reduction in cell viability. These results suggest that dianhydrogalactitol may provide a greater clinical benefit to glioma patients compared to the standard of care chemotherapy, temozolomide.

In vivo, dianhydrogalactitol (VAL-083) was administered in comparison to temozolomide (TMZ) in mice inoculated intracranially with human U251 glioblastoma cell lines.

On study day 0 for each set of mice, 44 female Rag2 mice were inoculated intracranially in the right caudate-putamen nucleus (coordinates: ML-1.5 mm; AP 1 mm; DV −3.5 mm) with $7.5 \times 10^4$ U251 human glioma cells. The inoculation timings and protocols are shown in Tables 5-7.

TABLE 5

| Gp# | Group Name | No. mice | TA/CA* Dose (mg/kg) | Admin. Route | Volume (µL/ 20 g) | Timepoint/ Schedule |
|---|---|---|---|---|---|---|
| 1 | Saline control | 3 | — | i.p. | 200 | M, W, F X3 |
| 2 | TMZ control | 0 | 30 | i.p. | 200 | M, W, F (Q2Dx3) |
| 3 | VAL-083 3 | 4 | 3 | i.p. | 200 | M, W, F X3 |
| 4 | VAL-083 4 | 4 | 4 | i.p. | 200 | M, W, F X3 |
| 5 | VAL-083 5 | 4 | 5 | i.p. | 200 | M, W, F x3 |

TABLE 6

| Gp# | Group Name | No. mice | TA/CA* Dose (mg/kg) | Admin. Route | Volume (µL/ 20 g) | Timepoint/ Schedule |
|---|---|---|---|---|---|---|
| 1 | Saline control | 3 | — | i.p. | 200 | M, W, F X3 |
| 2 | TMZ control | 0 | 30 | i.p. | 200 | M, W, F (Q2Dx3) |
| 3 | VAL-083 3 | 4 | 3 | i.p. | 200 | M, W, F X3 |
| 4 | VAL-083 4 | 4 | 4 | i.p. | 200 | M, W, F X3 |
| 5 | VAL-083 5 | 4 | 5 | i.p. | 200 | M, W, F X3 |

TABLE 7

| Gp# | Group Name | No. mice | TA/CA* Dose (mg/kg) | Admin. Route | Volume (µL/ 20 g) | Timepoint/ Schedule |
|---|---|---|---|---|---|---|
| 1 | Saline control | 4 | — | i.p. | 200 | M, W, F X3 |
| 2 | TMZ control | 8 | 30 | i.p. | 200 | M, W, F (Q2Dx3) |
| 3 | VAL-083 3 | 0 | 3 | i.p. | 200 | M, W, F X3 |
| 4 | VAL-083 4 | 0 | 4 | i.p. | 200 | M, W, F X3 |
| 5 | VAL-083 5 | 0 | 5 | i.p. | 200 | M, W, F X3 |

All animals received their doses as indicated unless terminated (i.e. there were no missed injections). Group 5 mice treated with 5 mg/kg VAL-083 received 4 doses; however, subsequent doses were discontinued due to treatment-related body weight loss and loose stools. Mice administered 4 mg/kg VAL-083 tolerated all doses of the test article; however, loose stools were observed during the last week of dosing.

For the first day of dosing, temozolomide (TMZ) was administered at 30 mg/kg as two injections.

The results for body weights are shown in FIG. 30. FIG. 30 shows results for body weight as a function of time for female Rag2 mice post-inoculation with U251 GBM cells. Mice were treated with varying concentrations of dianhydrogalactitol ("VAL-083") and with temozolomide (TMZ) Following the intracranial surgery (exposure to anesthesia), the mice lost weight and recovered within 3 days. Mice treated with 5 mg/kg VAL-083 (group 5) received only 4 doses as stated above. As with the vehicle control, significant weight loss is observed as tumor burden in the brain increases and thus it is hard to determine whether mice treated with 4 mg/kg VAL-083 (group 4) was attributed to tumor burden or treatment.

The results for survival (Kaplan-Meier plot) are shown in FIG. 31. The median survival time for mice treated with 4 mg/kg VAL-083 was significantly increased at 72 days compared to 48 days for saline controls (p<0.0001). Median survival time for 3 mg/kg VAL-083 was 54 days. A dose-dependent increase in median survival time was observed for mice treated with VAL-083 compared to vehicle control. Mice treated with 4 doses of 5 mg/kg VAL-083 had a median survival time of 57 days.

There were no significant observations noted on necropsy. Many of the observations noted whether a subcutaneous tumor was growing through the inoculation site through the skull cap.

In summary, VAL-083 treatment increased survival time in mice bearing intracranial U251 tumors in a dose-dependent manner. Mice administered 4 mg/kg VAL-083 received the full treatment course; however, loose stools were observed near the end of the dosing schedule. In mice receiving 5 mg/kg VAL-083, the drug was tolerable for 4 doses with the 3× weekly (for 4 weeks) dose schedule.

Example 3

Phase I/II Study of Dianhydrogalactitol in Patients with Recurrent Malignant Glioma Glioblastoma multiforme (GBM) is the most common and deadly form of human brain cancer. Median survival for patients with recurrent GBM is <6 months. Front-line systemic therapy is temozolomide, but resistance due to $O^6$-methylguanine-DNA-methyltransferase (MGMT) activity is implicated in poor prognoses. Dianhydrogalactitol (VAL-083) is a structurally unique bi-functional DNA alkylating agent that crosses the blood-brain barrier and accumulates in brain tumor tissue. In recent in vitro studies, VAL-083 overcame resistance to MGMT and demonstrated cytotoxic activity against GBM cell lines, as well as GBM cancer stem cells, and was shown to act as a radiosensitizer. Previous clinical trials suggest that VAL-083 has activity against a range of tumors, including GBM. In light of extensive safety data and previous studies, NCI-sponsored studies in GBM achieved promising results with limited toxicity using a dosing regimen of 25 mg/m²/day for five days every five weeks. The present dosing regimen utilizes a daily dose for three days every three weeks. Seven cohorts have completed the current trial with no drug-related serious adverse events: MTD was not yet reached at 40 mg/m²/day; 50 mg/m²/day is being studied and higher doses may be explored. Compared to historical trials, the present regimen delivers substantively more drug as measured by $C_{max}$ and dose density. A dose density of 25 mg/m²/week in combination with radiation was previously shown superior to radiation alone against GBM; a dose density of 50 mg/m²/week is being enrolled in the current trial. Pharmacokinetic analyses show dose-dependent linear systemic exposure with a short plasma 1-2 h terminal half-life; $C_{max}$ at 40 mg/m² in the current trial ranged from 1130-739 ng/mL (7.7-5.1 μM). Calculated CNS tissue concentrations, based on the plasma concentrations, exceed concentrations known to be effective against glioma cell lines in vitro.ing efficacy in CNS tumors, we initiated a new Phase I/II clinical study to establish the maximum tolerated dose (MTD) using an optimized dosing scheme. The goal of the current clinical trial is to determine an appropriate dose for advancement into registration trials as a potential new therapy for the treatment of refractory GBM.

Methods:

Open-label, single-arm Phase I/II dose-escalation study in patients with histologically-confirmed initial diagnosis of primary WHO Grade IV malignant glioma (glioblastoma). Patients enrolled have previously been treated with surgery and/or radiation, if appropriate, and must have failed both bevacizumab and temozolomide, unless contraindicated. The study utilizes a 3+3 dose-escalation design. Patients receive dianhydrogalactitol IV on days 1, 2, and 3 of a 21-day cycle. Tumor response is assessed according to RANO criteria prior to every other 21-day treatment cycle, and patients exhibiting stable disease or tumor regression are allowed to remain on study drug. The RANO (Response Assessment in Neuro-Oncology) criteria divide responses into four general categories: complete response, partial response, stable disease, and regression.

The results of the study were as follows: 25 patients have been enrolled across 8 dose cohorts ranging from 1.5 to 50 mg/m²/d. A dose limiting toxicity consisting of grade 4 thrombocytopenia was observed at dose level 8 (50 mg/m²/d). The DLT-related symptoms resolved rapidly and spontaneously without concomitant treatment. Prior to this, other treatment related toxicities have been mild to moderate and included two grade 1 lymphopenias and one grade 1 thrombocytopenia. Maximum tolerated dose (MTD) will be determined based on 3+3 design. Three patients had a response (stable disease or partial response) reporting improved clinical signs (maximum response of 84 wks). Pharmacokinetic analyses show dose-dependent linear systemic exposure with a short plasma 1-2 h terminal half-life; $C_{max}$ ranged from 1130-739 ng/mL (7.7-5.11 μM) at 40 mg/m²/d. Compared to historical trials, the present regimen delivers substantively more drug by Cmax and dose intensity. A dose intensity of 25 mg/m²/wk in combination with radiation was previously shown superior to radiation alone against GBM; a dose intensity of 50 mg/m²/wk is achieved in the current trial. The dosing of dianhydrogalactitol may be limited by myelosuppression; however, if myelosuppression occurs, it can be reversed relatively easily.

Example 4

Pharmacokinetic Results

Plasma drug concentration analysis data were analyzed using WinNonlin®, version 2.1A software (Pharsight Inc., Mountain View, Calif.) and Microsoft Office Excel 2007. Pharmacokinetic analysis was conducted by Dr. Sarath Kanekal, Ph.D. Use of MS Excel was limited to receipt of raw data, transfer into WinNonlin and generation of tables (Mean and SD) and graphs for the report.

Dianhydrogalactitol (DAG) for injection was reconstituted with 5 mL of 0.9% Sodium Chloride, USP, then diluted to 500 mL with 0.9% Sodium Chloride, USP or 5% Dextrose Injection, USP and was administered as an IV infusion over 30-60 minutes. The starting dose for Cohort #1 was 1.5 mg/m² IV daily×3 every 21 days. Cohorts 2 and 3 received DAG at doses of 3.0 and 5.0 mg/m² IV daily×3 every 21 days, respectively; cohort 4 received 10 mg/m². Dose escalation beyond 10 mg/m², up to 40 mg/m² IV daily×3 every 21 days is planned in the ongoing trial. Sample collection was on Day 1 at each dose level at the following time points: pre-dose, and 0.25, 0.5, 1, 2, 4, 6 h 15±5 minutes, 30±5 minutes, 60±10 minutes, 120±10 minutes, 240±15 minutes, and 360±15 minutes after the end of the IV study drug administration and immediately prior to Cycle 1, Day 2 of dosing. Drug concentration data was received from at least 3 patients for cohorts 1, 2 and 3, but only from 2 patients in cohort 4.

For the purposes of this interim analysis a fixed constant infusion time of 30 minutes and nominal collection time intervals were used for all patients. No separation was made between male and female patients because historical data did not reveal a sex difference in pharmacokinetics. For the final PK analysis individual patient infusion time and exact collection time are used.

Pharmacokinetic analyses were performed on the plasma concentration versus time data using WinNonlin (Ver 2.1A) via non-compartmental analysis (NCA). A model for constant infusion (WinNonlin Model #202) was used for the analyses. Uniform weighting was used for all data. $AUC_{all}$ was calculated by the linear trapezoid rule and $t_{1/2}$ of lambda z was used for estimating the terminal half-life. The last 2 or 3 concentrations above LLOQ were used for calculating lambda z. For clearance (CL) and Volume of Distribution (Vz), observed CL and observed $V_z$ values outputted by WinNonlin are reported here. All plasma concentrations measurements reported as below the limit of quantitation (BLQ) was set equal to zero, and those reported as NS (no sample), if any, were left blank and treated as missing. Mean concentration and WinNonlin derived parameters are presented with standard deviation.

The WinNonlin-derived parameters ($T_{max}$, $C_{max}$, AUC, and Terminal $t_{1/2}$ of DAG are presented in Table 8. Mean values of each cohort's time-concentration profiles from four cohorts is presented in FIG. 32. FIG. 32 shows the plasma concentration-time profile of dianhydrogalactitol in glioblastoma multiforme patients (data is shown for an additional cohort as compared with FIG. 2). Four cohorts are shown: ■ is cohort 1; ♦ is cohort 2; ▼ is cohort 3; and ▲ is cohort 4. Concentration (ng/mL) is shown on the y axis; time after administration is shown in the x axis. DAG was rapidly distributed at all dose levels, achieving peak concentration at 0.25 after initiation of the intravenous infusion. The drug is rapidly cleared and plasma concentrations returned to near baseline by 8 hours after dosing, often sooner at lower doses. Dose escalation showed more than dose proportional increase in exposure with every incremental dose escalation. The mean terminal half-life was variable and ranged from 0.83 to 2.02 hours.

TABLE 8

Summary of Pharmacokinetic Data

| Cohort | Dose mg/m² | $T_{max}$ h | $C_{max}$ ng/mL | AUC ng * h/mL | t-½ * h |
|---|---|---|---|---|---|
| 1 | 1.5 | 0.25 | 16.5 | 18.9 | 2.02 |
| 2 | 3 | 0.25 | 46.4 | 48.5 | 0.83 |
| 3 | 5 | 0.25 | 80.5 | 108.0 | 1.27 |
| 4 | 10 | 0.25 | 172.0 | 191.7 | 1.19 |

Pharmacokinetic analyses show dose-dependent systemic exposure with a short plasma 1-2 h half-life; average $C_{max}$ at the highest dose tested (10 mg/m²) is <200 ng/mL.

FIG. 32 shows the plasma concentration-time profile of dianhydrogalactitol in brain tumor patients. Four cohorts are shown: ■ is cohort 1; ♦ is cohort 2; ▼ is cohort 3; and ▲ is cohort 4. Concentration (ng/mL) is shown on the y axis; time after administration is shown in the x axis.

In conclusion, pharmacokinetics parameters of dianhydrogalactitol in the study reported in this example are consistent with previously reported values in the literature. The concentrations even at the highest dose tested (10 mg/m²) are lower than concentrations where anticancer efficacy has been reported. As dose escalation proceeds in the current study it is expected that higher therapeutic levels will be achieved.

ADVANTAGES OF THE INVENTION

The present invention provides effective methods and compositions for treating recurrent malignant glioma, especially glioblastoma multiforme, and for treating progressive secondary brain tumors, especially those arising from metastases of breast adenocarcinoma, small-cell lung carcinoma, or melanoma. These methods and compositions are well tolerated and do not cause significant side effects. They can be used together with radiation, surgery, or other chemotherapeutic agents.

Methods according to the present invention possess industrial applicability for the preparation of a medicament for the treatment of a number of diseases and conditions in subjects, including the malignancies of the central nervous system. Compositions according to the present invention possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patents and patent publications, are incorporated herein by reference.

What is claimed is:

1. A method for the treatment of recurrent glioma or progressive secondary brain tumor comprising the administration of a therapeutically effective quantity of a hexitol derivative selected from the group consisting of dianhydrogalactitol and diacetyldianhydrogalactitol, wherein the recurrent glioma is resistant to temozolomide and bevacizumab, and wherein the hexitol derivative is administered at a therapeutically effective dose of up to 40 mg/m$^2$ for 3 days followed by a nadir/recovery period of 18 to 21 days.

2. A method to improve the efficacy and/or reduce the side effects of the administration of a hexitol derivative for treatment of recurrent glioma or progressive secondary brain tumor comprising the steps of:
  (a) identifying at least one factor or parameter associated with the efficacy and/or occurrence of side effects of the administration of the hexitol derivative for treatment of the malignancy; and
  (b) modifying the factor or parameter to improve the efficacy and/or reduce the side effects of the administration of the hexitol derivative for treatment of the malignancy, wherein the hexitol derivative is dianhydrogalactitol, and wherein the recurrent glioma is resistant to temozolomide and bevacizumab and the factor or parameter is one or more of dose modification, route of administration, and/or schedule of administration; and
  wherein the hexitol derivative is administered at a therapeutically effective dose of up to 40 mg/m$^2$ for 3 days followed by a nadir/recovery period of 18 to 21 days.

3. The method of claim 1, wherein the dosing is up to a cumulative effective quantity of 240 mg/m$^2$ in a 33-day treatment cycle.

4. The method of claim 3, wherein the dosing is up to a cumulative effective quantity of 240 mg/m$^2$ in a 33-day treatment cycle.

5. The method of claim 1, wherein the hexitol derivative is administered on days 1, 2 and 3.

6. A method for the treatment of recurrent glioma or progressive secondary brain tumor comprising the administration of a therapeutically effective quantity of a hexitol derivative selected from the group consisting of dianhydrogalactitol and diacetyldianhydrogalactitol, wherein the recurrent glioma is resistant to temozolomide and bevacizumab, and wherein the hexitol derivative is administered at a therapeutically effective dose of up to 40 mg/m$^2$ for 3 days followed by a nadir/recovery period of 18 to 21 days, and wherein the dosing is up to a cumulative effective quantity of 240 mg/m$^2$ in a 33-day treatment cycle.

7. The method of claim 6, wherein the hexitol derivative is administered on days 1, 2, and 3.

8. A method to improve the efficacy and/or reduce the side effects of the administration of a hexitol derivative for treatment of recurrent glioma or progressive secondary brain tumor comprising the steps of:
  (a) identifying at least one factor or parameter associated with the efficacy and/or occurrence of side effects of the administration of the hexitol derivative for treatment of the malignancy; and
  (b) modifying the factor or parameter to improve the efficacy and/or reduce the side effects of the administration of the hexitol derivative for treatment of the malignancy, wherein the hexitol derivative is dianhydrogalactitol, and wherein the recurrent glioma is resistant to temozolomide and bevacizumab and the factor or parameter is one or more of dose modification, route of administration, and/or schedule of administration; and
  wherein the hexitol derivative is administered at a therapeutically effective dose of up to 40 mg/m$^2$ for 3 days followed by a nadir/recovery period of 18 to 21 days, and wherein the dosing is up to a cumulative effective quantity of 240 mg/m$^2$ in a 33-day treatment cycle.

\* \* \* \* \*